United States Patent
Christopher et al.

(10) Patent No.: US 12,156,866 B2
(45) Date of Patent: *Dec. 3, 2024

(54) METHODS OF TREATING CONDITIONS RELATED TO THE S1P₁ RECEPTOR

(71) Applicant: Arena Pharmaceuticals, Inc., San Diego, CA (US)

(72) Inventors: Ronald J. Christopher, Carlsbad, CA (US); Abu J. M. Sadeque, San Diego, CA (US)

(73) Assignee: Arena Pharmaceuticals, Inc., New York, NY (US)

( * ) Notice: Subject to any disclaimer, the term of this patent is extended or adjusted under 35 U.S.C. 154(b) by 917 days.

This patent is subject to a terminal disclaimer.

(21) Appl. No.: 15/734,920

(22) PCT Filed: Jun. 5, 2019

(86) PCT No.: PCT/US2019/035662
§ 371 (c)(1),
(2) Date: Dec. 3, 2020

(87) PCT Pub. No.: WO2019/236757
PCT Pub. Date: Dec. 12, 2019

(65) Prior Publication Data
US 2021/0228545 A1    Jul. 29, 2021

Related U.S. Application Data

(60) Provisional application No. 62/681,426, filed on Jun. 6, 2018, provisional application No. 62/746,946, filed on (Continued)

(51) Int. Cl.
*A61K 31/403*    (2006.01)
*A61K 45/06*    (2006.01)

(52) U.S. Cl.
CPC ........... *A61K 31/403* (2013.01); *A61K 45/06* (2013.01)

(58) Field of Classification Search
CPC .......... A61P 1/04; A61P 29/00; A61K 31/192; A61K 31/195; A61K 31/403;
(Continued)

(56) References Cited

U.S. PATENT DOCUMENTS

| 3,206,470 A | 9/1965 | William et al. |
| 3,503,963 A | 3/1970 | Schweizer et al. |

(Continued)

FOREIGN PATENT DOCUMENTS

| AT | 327605 | 6/2006 |
| AU | 492126 | 11/1975 |

(Continued)

OTHER PUBLICATIONS

Tran et. al., Clin. Pharm. in Drug Develop., vol. 7(6), pp. 634-640, publ. Nov. 10, 2017 (Year: 2017).*

(Continued)

*Primary Examiner* — Sarah Pihonak
(74) *Attorney, Agent, or Firm* — Zhigang Rao

(57) ABSTRACT

Provided are methods of treatment of a sphingosine 1-phosphate subtype 1 (S1P₁) receptor-associated disorder comprising prescribing and/or administering to an individual in need thereof a standard dose of (R)-2-(7-(4-cyclopentyl-3-(trifluoromethyl) benzyloxy)-1,2,3,4-tetrahydrocyclopenta[b]indol-3-yl)acetic acid (Compound 1), or a pharmaceutically acceptable salt, hydrate, or solvate thereof.

18 Claims, 1 Drawing Sheet

Compound 1 Mean Plasma Concentration-Time Profiles

Related U.S. Application Data on Oct. 17, 2018, provisional application No. 62/850,470, filed on May 20, 2019.

(58) Field of Classification Search
CPC .. A61K 31/4196; A61K 31/49; A61K 31/496; A61K 31/565; A61K 31/566; A61K 31/7048; A61K 31/437; A61K 31/439; A61K 31/4545; A61K 31/4706; A61K 31/5377; A61K 45/06; A61K 9/2018; A61K 9/2054; A61K 9/48; C07D 519/00
See application file for complete search history.

(56) References Cited

U.S. PATENT DOCUMENTS

| | | |
|---|---|---|
| 3,592,932 A | 7/1971 | Duerr et al. |
| 3,598,801 A | 8/1971 | Beffa et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,948,914 A | 4/1976 | Fischer |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,057,559 A | 11/1977 | Asselin et al. |
| 4,101,541 A | 7/1978 | Petitpierre et al. |
| 4,139,705 A | 2/1979 | Dunbar et al. |
| 4,189,427 A | 2/1980 | Komorowski |
| 4,189,579 A | 2/1980 | Dunbar et al. |
| 4,242,507 A | 12/1980 | Itoh et al. |
| 4,267,174 A | 5/1981 | Berger et al. |
| 4,273,870 A | 6/1981 | Endo et al. |
| 4,275,148 A | 6/1981 | Endo et al. |
| 4,343,804 A | 8/1982 | Munison et al. |
| 4,397,848 A | 8/1983 | Bosies et al. |
| 4,476,248 A | 10/1984 | Gordon et al. |
| 4,493,726 A | 1/1985 | Burdeska et al. |
| 4,517,183 A | 5/1985 | Bosies et al. |
| 4,612,376 A | 9/1986 | Takaya et al. |
| 4,643,995 A | 2/1987 | Engel et al. |
| 4,766,213 A | 8/1988 | Juraszyk et al. |
| 4,782,076 A | 11/1988 | Mobilio et al. |
| 4,810,699 A | 3/1989 | Sabatucci et al. |
| 4,880,932 A | 11/1989 | Moriya et al. |
| 5,221,678 A | 6/1993 | Atkinson et al. |
| 5,571,815 A | 11/1996 | Schaper et al. |
| 5,624,941 A | 4/1997 | Barth et al. |
| 5,691,364 A | 11/1997 | Buckman et al. |
| 5,776,967 A | 7/1998 | Kreft et al. |
| 5,830,911 A | 11/1998 | Failli et al. |
| 5,849,759 A | 12/1998 | Amaiz et al. |
| 5,948,786 A | 9/1999 | Fujiwara et al. |
| 5,952,504 A | 9/1999 | Yoo et al. |
| 5,962,479 A | 10/1999 | Chen |
| 6,008,234 A | 12/1999 | Kochanny et al. |
| 6,060,478 A | 5/2000 | Gilligan |
| 6,107,301 A | 8/2000 | Aldrich et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,267,985 B1 | 7/2001 | Chen et al. |
| 6,294,671 B1 | 9/2001 | Frietze |
| 6,350,750 B1 | 2/2002 | Den Hartog et al. |
| 6,410,583 B1 | 6/2002 | Labelle et al. |
| 6,414,002 B1 | 7/2002 | Cheng et al. |
| 6,506,762 B1 | 1/2003 | Horvath et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,552,192 B1 | 4/2003 | Hanus et al. |
| 6,569,879 B2 | 5/2003 | Liu et al. |
| 6,583,154 B1 | 6/2003 | Norman et al. |
| 6,620,821 B2 | 9/2003 | Robl et al. |
| 6,660,744 B1 | 12/2003 | Hirst et al. |
| 6,713,508 B2 | 3/2004 | Sahoo et al. |
| 6,787,542 B2 | 9/2004 | Wang et al. |
| 6,844,351 B1 | 1/2005 | Chen et al. |
| 6,849,636 B2 | 2/2005 | Waddell et al. |
| 6,956,047 B1 | 10/2005 | Chen et al. |
| 6,960,692 B2 | 11/2005 | Kohno et al. |
| 7,056,942 B2 | 6/2006 | Hildesheim et al. |
| 7,057,046 B2 | 6/2006 | Sher et al. |
| 7,083,933 B1 | 8/2006 | Griffin |
| 7,098,235 B2 | 8/2006 | Sher et al. |
| 7,132,426 B2 | 11/2006 | Jones et al. |
| 7,250,441 B2 | 7/2007 | Gopalsamy et al. |
| 7,276,249 B2 | 10/2007 | Ryde et al. |
| 7,417,039 B2 | 8/2008 | Davis |
| 7,425,630 B2 | 9/2008 | Gharbaoui et al. |
| 7,470,699 B2 | 12/2008 | Jones et al. |
| 7,625,906 B2 | 12/2009 | Jones et al. |
| 7,763,278 B2 | 7/2010 | Cooper et al. |
| 7,812,159 B2 | 10/2010 | Gharbaoui et al. |
| 7,838,525 B2 | 11/2010 | Jones et al. |
| 8,293,751 B2 | 10/2012 | Jones et al. |
| 8,362,248 B2 | 1/2013 | Jones et al. |
| 8,410,119 B2 | 4/2013 | Jones et al. |
| 8,415,484 B2 | 4/2013 | Jones et al. |
| 8,580,841 B2 | 11/2013 | Jones et al. |
| 8,853,419 B2 | 10/2014 | Montalban et al. |
| 9,085,581 B2 | 7/2015 | Jones et al. |
| 9,108,969 B2 | 8/2015 | Jones et al. |
| 9,126,932 B2 | 9/2015 | Jones et al. |
| 9,175,320 B2 | 11/2015 | Montalban et al. |
| 9,447,041 B2 | 9/2016 | Montalban et al. |
| 9,522,133 B2 | 12/2016 | Jones et al. |
| 10,301,262 B2 | 5/2019 | Blackburn et al. |
| 10,676,435 B2 | 6/2020 | Blackburn |
| 11,007,175 B2 | 5/2021 | Glicklich et al. |
| 11,091,435 B2 | 8/2021 | Blackburn et al. |
| 11,149,292 B2 | 10/2021 | Montalban et al. |
| 2002/0058026 A1 | 5/2002 | Hammerly |
| 2002/0137755 A1 | 9/2002 | Bilodeau et al. |
| 2002/0156081 A1 | 10/2002 | Hirst et al. |
| 2003/0083269 A1 | 5/2003 | Brouillette et al. |
| 2003/0211421 A1 | 11/2003 | Hanabata et al. |
| 2003/0224058 A1 | 12/2003 | Ryde et al. |
| 2004/0110241 A1 | 6/2004 | Segal |
| 2004/0224941 A1 | 11/2004 | Seko et al. |
| 2004/0254222 A1 | 12/2004 | Kohno et al. |
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi et al. |
| 2005/0014728 A1 | 1/2005 | Pan et al. |
| 2005/0033055 A1 | 2/2005 | Bugianesi et al. |
| 2005/0070562 A1 | 3/2005 | Jones et al. |
| 2005/0182067 A1 | 8/2005 | Balan et al. |
| 2005/0197353 A1 | 9/2005 | Ritzeler et al. |
| 2005/0209251 A1 | 9/2005 | Linker et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0154866 A1 | 7/2006 | Chu et al. |
| 2006/0155128 A1 | 7/2006 | Jones et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0066590 A1 | 3/2007 | Jones et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0149595 A1 | 6/2007 | Tanaka et al. |

(56) References Cited

U.S. PATENT DOCUMENTS

| | | |
|---|---|---|
| 2007/0149597 A1 | 6/2007 | Nishi et al. |
| 2007/0167413 A1 | 7/2007 | Srinivas et al. |
| 2007/0167425 A1 | 7/2007 | Nakade et al. |
| 2007/0167473 A1 | 7/2007 | Tones et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0225351 A1 | 9/2007 | Lippa et al. |
| 2007/0244155 A1 | 10/2007 | Sharma et al. |
| 2007/0254886 A1 | 11/2007 | Habashita et al. |
| 2007/0259928 A1 | 11/2007 | Yoshida et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0004265 A1 | 1/2009 | Misselwitz et al. |
| 2009/0012093 A1 | 1/2009 | Fukatsu et al. |
| 2009/0036434 A1 | 2/2009 | Jones et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0203676 A1 | 8/2009 | Barba et al. |
| 2009/0253802 A1 | 10/2009 | Kaneko |
| 2009/0270409 A1 | 10/2009 | Alper et al. |
| 2009/0286816 A1 | 11/2009 | Jones et al. |
| 2009/0325907 A1 | 12/2009 | Kohno et al. |
| 2010/0004272 A1 | 1/2010 | Jones et al. |
| 2010/0029650 A1 | 2/2010 | Fang et al. |
| 2010/0160359 A1 | 6/2010 | Jones et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0000153 A1 | 1/2011 | Albert |
| 2011/0039933 A1 | 2/2011 | Evindar et al. |
| 2011/0082134 A1 | 4/2011 | Jones et al. |
| 2011/0105471 A1 | 5/2011 | Burcham |
| 2011/0112060 A1 | 5/2011 | Jones et al. |
| 2011/0130409 A1 | 6/2011 | Jones |
| 2011/0159096 A1 | 6/2011 | Duran Lopez et al. |
| 2011/0160243 A1 | 6/2011 | Jones et al. |
| 2011/0230457 A1 | 9/2011 | Berghausen et al. |
| 2012/0064060 A1 | 3/2012 | Habashita et al. |
| 2012/0295947 A1 | 11/2012 | Montalban et al. |
| 2012/0329848 A1 | 12/2012 | Jones et al. |
| 2013/0023494 A1 | 1/2013 | Jones et al. |
| 2013/0023527 A1 | 1/2013 | Jones et al. |
| 2013/0184307 A1 | 7/2013 | Jones et al. |
| 2013/0203807 A1 | 8/2013 | Tarcic et al. |
| 2014/0038889 A1 | 2/2014 | Jones |
| 2014/0038987 A1 | 2/2014 | Jones et al. |
| 2014/0051629 A1 | 2/2014 | Jones et al. |
| 2014/0155654 A1 | 6/2014 | Preda et al. |
| 2014/0350115 A1 | 11/2014 | Kostik et al. |
| 2014/0357690 A1 | 12/2014 | Montalban et al. |
| 2015/0336966 A1 | 8/2015 | Jones et al. |
| 2015/0284399 A1 | 10/2015 | Jones et al. |
| 2015/0335618 A1 | 11/2015 | Jones et al. |
| 2016/0016904 A1 | 1/2016 | Montalban et al. |
| 2016/0038506 A1 | 2/2016 | Podolski et al. |
| 2017/0159088 A1 | 6/2017 | Montalban et al. |
| 2017/0217885 A1 | 8/2017 | Jones et al. |
| 2017/0320820 A1 | 11/2017 | Borell et al. |
| 2018/0186738 A1 | 7/2018 | Blackburn et al. |
| 2018/0263958 A1 | 9/2018 | Glicklich et al. |
| 2019/0135752 A1 | 5/2019 | Jones et al. |
| 2019/0330153 A1 | 10/2019 | Blackburn et al. |
| 2020/0000770 A1 | 1/2020 | Lassen et al. |
| 2020/0016121 A1 | 1/2020 | Lassen et al. |
| 2020/0361869 A1 | 11/2020 | Blackburn et al. |
| 2020/0407316 A1 | 12/2020 | Jones et al. |
| 2021/0338636 A1 | 11/2021 | Glicklich et al. |
| 2021/0386706 A1 | 12/2021 | Adams |
| 2022/0002244 A1 | 1/2022 | Blackburn et al. |
| 2022/0023258 A1 | 1/2022 | Naik |
| 2022/0142977 A1 | 5/2022 | Naik |

FOREIGN PATENT DOCUMENTS

| | | |
|---|---|---|
| BE | 829845 | 12/1975 |
| BE | 868796 | 1/1979 |
| CA | 2499497 | 4/2004 |
| CH | 560197 | 3/1975 |
| CN | 1212117 C | 7/2005 |
| CN | 101980704 | 2/2011 |
| CN | 101981030 | 2/2011 |
| CN | 102197038 | 9/2011 |
| CN | 105816453 | 8/2016 |
| CN | 106278999 | 1/2017 |
| DE | 2048375 | 4/1971 |
| DE | 2223644 | 11/1972 |
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| DE | 19602095 | 7/1997 |
| DE | 19737723 | 2/1999 |
| DE | 19962936 | 6/2001 |
| EP | 0014976 | 9/1980 |
| EP | 0053678 | 10/1981 |
| EP | 0050671 | 5/1982 |
| EP | 0055693 | 7/1982 |
| EP | 0123402 | 10/1984 |
| EP | 0149088 | 12/1984 |
| EP | 0154190 | 9/1985 |
| EP | 0191603 | 8/1986 |
| EP | 0193249 | 9/1986 |
| EP | 0283261 | 9/1988 |
| EP | 0324426 | 7/1989 |
| EP | 0468785 | 1/1992 |
| EP | 0518675 | 12/1992 |
| EP | 0526004 | 2/1993 |
| EP | 0556889 | 8/1993 |
| EP | 0565488 | 10/1993 |
| EP | 0604800 | 7/1994 |
| EP | 0667343 | 8/1995 |
| EP | 0801059 | 10/1997 |
| EP | 0857483 | 8/1998 |
| EP | 0940 387 | 9/1999 |
| EP | 1074549 | 2/2001 |
| EP | 1097709 | 5/2001 |
| EP | 1195165 | 4/2002 |
| EP | 1287133 | 3/2003 |
| EP | 1040831 | 5/2003 |
| EP | 1338651 | 8/2003 |
| EP | 1340749 | 9/2003 |
| EP | 1475094 | 11/2004 |
| EP | 1650186 | 4/2006 |
| EP | 1826197 | 8/2007 |
| EP | 1902730 | 3/2008 |
| EP | 2003132 | 12/2008 |
| EP | 1772145 | 3/2011 |
| EP | 2017263 | 11/2011 |
| FR | 1551400 | 12/1968 |
| GB | 935595 | 8/1963 |
| GB | 1250624 | 10/1971 |
| GB | 1311956 | 3/1973 |
| GB | 1393993 | 5/1975 |
| GB | 1436893 | 5/1976 |
| GB | 1493380 | 11/1977 |
| GB | 1495665 | 12/1977 |
| JP | 55-17382 | 2/1980 |
| JP | 61-057587 | 3/1986 |
| JP | 05-33359 | 12/1993 |
| JP | 07-53546 | 2/1995 |
| JP | 11-193277 | 7/1999 |
| JP | 2000-038350 | 2/2000 |
| JP | 2001-089452 | 4/2001 |

(56) References Cited

FOREIGN PATENT DOCUMENTS

| | | |
|---|---|---|
| JP | 2004-67575 | 3/2004 |
| JP | 2004-269468 | 9/2004 |
| JP | 2004-269469 | 9/2004 |
| JP | 2007-262009 | 10/2007 |
| NL | 66144961 | 4/1967 |
| NL | 6814810 | 4/1969 |
| RU | 938 559 | 11/1993 |
| RU | 2067978 | 10/1996 |
| RU | 2119917 | 10/1998 |
| RU | 2153495 | 7/2000 |
| RU | 2158258 | 10/2000 |
| RU | 2198879 | 2/2003 |
| RU | 2200734 | 3/2003 |
| RU | 2015141151 | 5/2017 |
| WO | WO 1981/003174 | 11/1981 |
| WO | WO 1991/006537 | 5/1991 |
| WO | WO 1992/001697 | 2/1992 |
| WO | WO 1992/012976 | 8/1992 |
| WO | WO 1994/007858 | 4/1994 |
| WO | WO 1994/013677 | 6/1994 |
| WO | WO 1995/033750 | 12/1995 |
| WO | WO 1996/028427 | 9/1996 |
| WO | WO 1996/032383 | 10/1996 |
| WO | WO 1996/033980 | 10/1996 |
| WO | WO 1996/033994 | 10/1996 |
| WO | WO 1996/035689 | 11/1996 |
| WO | WO 1996/036613 | 11/1996 |
| WO | WO 1997/008152 | 3/1997 |
| WO | WO 1997/014674 | 4/1997 |
| WO | WO 1997/026252 | 7/1997 |
| WO | WO 1997/028137 | 8/1997 |
| WO | WO 1997/029109 | 8/1997 |
| WO | WO 1997/040832 | 11/1997 |
| WO | WO 1997/048696 | 12/1997 |
| WO | WO 1997/049706 | 12/1997 |
| WO | WO 1998/004528 | 2/1998 |
| WO | WO 1998/008846 | 3/1998 |
| WO | WO 1998/008847 | 3/1998 |
| WO | WO 1998/011094 | 3/1998 |
| WO | WO 1998/013354 | 4/1998 |
| WO | WO 1998/019998 | 5/1998 |
| WO | WO 1998/027081 | 6/1998 |
| WO | WO 1998/035967 | 8/1998 |
| WO | WO 1998/047874 | 10/1998 |
| WO | WO 1998/047903 | 10/1998 |
| WO | WO 1999/009026 | 2/1999 |
| WO | WO 1999/051599 | 10/1999 |
| WO | WO 2000/011003 | 3/2000 |
| WO | WO 2000/027825 | 5/2000 |
| WO | WO 2000/031068 | 6/2000 |
| WO | WO 2000/031258 | 6/2000 |
| WO | WO 2000/034241 | 6/2000 |
| WO | WO 2000/035875 | 6/2000 |
| WO | WO 2000/035886 | 6/2000 |
| WO | WO 2000/055153 | 9/2000 |
| WO | WO 2000/064888 | 11/2000 |
| WO | WO 2001/060807 | 2/2001 |
| WO | WO 2001/022938 | 4/2001 |
| WO | WO 2001/023387 | 4/2001 |
| WO | WO 2001/023388 | 4/2001 |
| WO | WO 2001/025210 | 4/2001 |
| WO | WO 2001/027107 | 4/2001 |
| WO | WO 2001/037831 | 5/2001 |
| WO | WO 2001/046204 | 6/2001 |
| WO | WO 2001/047887 | 7/2001 |
| WO | WO 2001/049677 | 7/2001 |
| WO | WO 2001/053263 | 7/2001 |
| WO | WO 2001/058900 | 8/2001 |
| WO | WO 2001/060870 | 8/2001 |
| WO | WO 2001/062233 | 8/2001 |
| WO | WO 2001/076573 | 10/2001 |
| WO | WO 2001/085699 | 11/2001 |
| WO | WO 2001/087829 | 11/2001 |
| WO | WO 2001/087892 | 11/2001 |
| WO | WO 2001/090082 | 11/2001 |
| WO | WO 2002/002539 | 1/2002 |
| WO | WO 2002/002549 | 1/2002 |
| WO | WO 2002/006237 | 1/2002 |
| WO | WO 2002/006274 | 1/2002 |
| WO | WO 2002/008188 | 1/2002 |
| WO | WO 2002/019975 | 3/2002 |
| WO | WO 2002/024169 | 3/2002 |
| WO | WO 2002/032408 | 4/2002 |
| WO | WO 2002/032893 | 4/2002 |
| WO | WO 2002/039987 | 5/2002 |
| WO | WO 2002/040451 | 5/2002 |
| WO | WO 2002/040456 | 5/2002 |
| WO | WO 2002/040458 | 5/2002 |
| WO | WO 2002/040480 | 5/2002 |
| WO | WO 2002/044362 | 6/2002 |
| WO | WO 2002/045652 | 6/2002 |
| WO | WO 2002/050071 | 6/2002 |
| WO | WO 2002/059083 | 8/2002 |
| WO | WO 2002/060388 | 8/2002 |
| WO | WO 2002/064094 | 8/2002 |
| WO | WO 2002/064616 | 8/2002 |
| WO | WO 2002/070485 | 9/2002 |
| WO | WO 2002/072101 | 9/2002 |
| WO | WO 2002/081454 | 10/2002 |
| WO | WO 2002/085892 | 10/2002 |
| WO | WO 2002/092068 | 11/2002 |
| WO | WO 2002/098864 | 12/2002 |
| WO | WO 2002/098878 | 12/2002 |
| WO | WO 2002/102313 | 12/2002 |
| WO | WO 2003/000666 | 1/2003 |
| WO | WO 2003/002544 | 1/2003 |
| WO | WO 2003/004498 | 1/2003 |
| WO | WO 2003/018556 | 3/2003 |
| WO | WO 2003/026661 | 4/2003 |
| WO | WO 2003/029205 | 4/2003 |
| WO | WO 2003/032989 | 4/2003 |
| WO | WO 2003/050117 | 6/2003 |
| WO | WO 2003/051822 | 6/2003 |
| WO | WO 2003/057689 | 7/2003 |
| WO | WO 2003/059378 | 7/2003 |
| WO | WO 2003/061663 | 7/2003 |
| WO | WO 2003/062252 | 7/2003 |
| WO | WO 2003/073986 | 9/2003 |
| WO | WO 2003/074008 | 9/2003 |
| WO | WO 2003/076418 | 9/2003 |
| WO | WO 2003/077656 | 9/2003 |
| WO | WO 2003/080070 | 10/2003 |
| WO | WO 2003/087064 | 10/2003 |
| WO | WO 2003/088962 | 10/2003 |
| WO | WO 2003/093269 | 11/2003 |
| WO | WO 2003/094845 | 11/2003 |
| WO | WO 2003/061567 | 12/2003 |
| WO | WO 2003/103632 | 12/2003 |
| WO | WO 2003/103633 | 12/2003 |
| WO | WO 2003/103640 | 12/2003 |
| WO | WO 2003/104208 | 12/2003 |
| WO | WO 2003/105763 | 12/2003 |
| WO | WO 2003/105771 | 12/2003 |
| WO | WO 2003/106450 | 12/2003 |
| WO | WO 2004/000762 | 12/2003 |
| WO | WO 2004/000819 | 12/2003 |
| WO | WO 2004/000843 | 12/2003 |
| WO | WO 2004/002495 | 1/2004 |
| WO | WO 2004/004777 | 1/2004 |
| WO | WO 2004/004778 | 1/2004 |
| WO | WO 2004/009596 | 1/2004 |
| WO | WO 2004/009597 | 1/2004 |
| WO | WO 2004/009602 | 1/2004 |
| WO | WO 2004/010936 | 2/2004 |
| WO | WO 2004/010992 | 2/2004 |
| WO | WO 2004/013633 | 2/2004 |
| WO | WO 2004/014871 | 2/2004 |
| WO | WO 2004/017896 | 3/2004 |
| WO | WO 2004/019869 | 3/2004 |
| WO | WO 2004/020408 | 3/2004 |
| WO | WO 2004/020409 | 3/2004 |
| WO | WO 2004/024943 | 3/2004 |
| WO | WO 2004/029204 | 4/2004 |
| WO | WO 2004/031189 | 4/2004 |

(56) References Cited

FOREIGN PATENT DOCUMENTS

| | | |
|---|---|---|
| WO | WO 2004/033431 | 4/2004 |
| WO | WO 2004/033710 | 4/2004 |
| WO | WO 2004/035588 | 4/2004 |
| WO | WO 2004/037823 | 5/2004 |
| WO | WO 2004/041164 | 5/2004 |
| WO | WO 2004/056748 | 7/2004 |
| WO | WO 2004/056825 | 7/2004 |
| WO | WO 2004/056829 | 7/2004 |
| WO | WO 2004/058174 | 7/2004 |
| WO | WO 2004/058727 | 7/2004 |
| WO | WO 2004/062665 | 7/2004 |
| WO | WO 2004/064806 | 8/2004 |
| WO | WO 2004/065380 | 8/2004 |
| WO | WO 2004/066963 | 8/2004 |
| WO | WO 2004/058149 | 9/2004 |
| WO | WO 2004/074218 | 9/2004 |
| WO | WO 2004/074297 | 9/2004 |
| WO | WO 2004/076413 | 9/2004 |
| WO | WO 2004/010949 | 10/2004 |
| WO | WO 2004/071442 | 10/2004 |
| WO | WO 2004/085401 | 10/2004 |
| WO | WO 2004/096752 | 11/2004 |
| WO | WO 2004/096757 | 11/2004 |
| WO | WO 2004/098583 | 11/2004 |
| WO | WO 2004/099144 | 11/2004 |
| WO | WO 2004/103279 | 12/2004 |
| WO | WO 2004/103306 | 12/2004 |
| WO | WO 2004/103309 | 12/2004 |
| WO | WO 2004/103997 | 12/2004 |
| WO | WO 2004/104205 | 12/2004 |
| WO | WO 2004/110368 | 12/2004 |
| WO | WO 2004/110979 | 12/2004 |
| WO | WO 2004/111000 | 12/2004 |
| WO | WO 2004/113330 | 12/2004 |
| WO | WO 2005/000833 | 1/2005 |
| WO | WO 2005/007647 | 1/2005 |
| WO | WO 2005/007658 | 1/2005 |
| WO | WO 2005/016894 | 2/2005 |
| WO | WO 2005/020920 | 3/2005 |
| WO | WO 2005/021503 | 3/2005 |
| WO | WO 2005/023762 | 3/2005 |
| WO | WO 2005/025554 | 3/2005 |
| WO | WO 2005/026148 | 3/2005 |
| WO | WO 2005/020882 | 4/2005 |
| WO | WO 2005/030127 | 4/2005 |
| WO | WO 2005/030129 | 4/2005 |
| WO | WO 2005/030751 | 4/2005 |
| WO | WO 2005/032465 | 4/2005 |
| WO | WO 2005/033099 | 4/2005 |
| WO | WO 2005/035525 | 4/2005 |
| WO | WO 2005/037215 | 4/2005 |
| WO | WO 2005/040095 | 5/2005 |
| WO | WO 2005/041899 | 5/2005 |
| WO | WO 2005/042488 | 5/2005 |
| WO | WO 2005/044780 | 5/2005 |
| WO | WO 2005/046603 | 5/2005 |
| WO | WO 2005/047297 | 5/2005 |
| WO | WO 2005/049033 | 6/2005 |
| WO | WO 2005/058315 | 6/2005 |
| WO | WO 2005/058848 | 6/2005 |
| WO | WO 2005/058849 | 6/2005 |
| WO | WO 2005/061489 | 7/2005 |
| WO | WO 2005/063750 | 7/2005 |
| WO | WO 2005/070886 | 8/2005 |
| WO | WO 2005/072530 | 8/2005 |
| WO | WO 2005/075426 | 8/2005 |
| WO | WO 2005/079788 | 9/2005 |
| WO | WO 2005/080330 | 9/2005 |
| WO | WO 2005/082089 | 9/2005 |
| WO | WO 2005/082841 | 9/2005 |
| WO | WO 2005/085179 | 9/2005 |
| WO | WO 2005/090348 | 9/2005 |
| WO | WO 2005/097745 | 10/2005 |
| WO | WO 2005/100365 | 10/2005 |
| WO | WO 2005/058295 | 11/2005 |
| WO | WO 2005/117909 | 12/2005 |
| WO | WO 2005/121121 | 12/2005 |
| WO | WO 2005/123677 | 12/2005 |
| WO | WO 2006/001463 | 1/2006 |
| WO | WO 2006/009092 | 1/2006 |
| WO | WO 2006/010379 | 2/2006 |
| WO | WO 2006/011554 | 2/2006 |
| WO | WO 2006/013948 | 2/2006 |
| WO | WO 2006/020951 | 2/2006 |
| WO | WO 2006/010544 | 3/2006 |
| WO | WO 2006/034337 | 3/2006 |
| WO | WO 2006/034446 | 3/2006 |
| WO | WO 2006/039325 | 4/2006 |
| WO | WO 2006/040966 | 4/2006 |
| WO | WO 2006/043149 | 4/2006 |
| WO | WO 2006/043490 | 4/2006 |
| WO | WO 2006/047195 | 5/2006 |
| WO | WO 2006/047516 | 5/2006 |
| WO | WO 2006/050946 | 5/2006 |
| WO | WO 2006/052566 | 5/2006 |
| WO | WO 2006/064757 | 6/2006 |
| WO | WO 2006/067531 | 6/2006 |
| WO | WO 2006/067532 | 6/2006 |
| WO | WO 2006/070208 | 7/2006 |
| WO | WO 2006/076231 | 7/2006 |
| WO | WO 2006/076243 | 7/2006 |
| WO | WO 2006/076455 | 7/2006 |
| WO | WO 2006/078992 | 7/2006 |
| WO | WO 2006/079406 | 8/2006 |
| WO | WO 2006/083491 | 8/2006 |
| WO | WO 2006/088944 | 8/2006 |
| WO | WO 2006/100631 | 9/2006 |
| WO | WO 2006/100633 | 9/2006 |
| WO | WO 2006/100635 | 9/2006 |
| WO | WO 2006/063033 | 11/2006 |
| WO | WO 2006/131336 | 12/2006 |
| WO | WO 2006/137019 | 12/2006 |
| WO | WO 2006/137509 | 12/2006 |
| WO | WO 2007/003964 | 1/2007 |
| WO | WO 2007/005673 | 1/2007 |
| WO | WO 2007/024922 | 3/2007 |
| WO | WO 2007/035355 | 3/2007 |
| WO | WO 2007/037196 | 4/2007 |
| WO | WO 2007/039470 | 4/2007 |
| WO | WO 2007/060626 | 5/2007 |
| WO | WO 2007/080542 | 7/2007 |
| WO | WO 2007/083089 | 7/2007 |
| WO | WO 2007/085451 | 8/2007 |
| WO | WO 2007/086001 | 8/2007 |
| WO | WO 2007/089335 | 8/2007 |
| WO | WO 2007/091396 | 8/2007 |
| WO | WO 2007/091501 | 8/2007 |
| WO | WO 2007/092638 | 8/2007 |
| WO | WO 2007/098474 | 8/2007 |
| WO | WO 2007/100617 | 9/2007 |
| WO | WO 2007/109330 | 9/2007 |
| WO | WO 2007/109334 | 9/2007 |
| WO | WO 2007/095561 | 10/2007 |
| WO | WO 2007/115820 | 10/2007 |
| WO | WO 2007/116866 | 10/2007 |
| WO | WO 2007/120689 | 10/2007 |
| WO | WO 2007/120702 | 10/2007 |
| WO | WO 2007/061458 | 11/2007 |
| WO | WO 2007/092190 | 11/2007 |
| WO | WO 2007/129473 | 11/2007 |
| WO | WO 2007/129745 | 11/2007 |
| WO | WO 2007/132307 | 11/2007 |
| WO | WO 2008/005569 | 1/2008 |
| WO | WO 2008/005576 | 1/2008 |
| WO | WO 2008/008895 | 1/2008 |
| WO | WO 2008/016674 | 2/2008 |
| WO | WO 2008/018427 | 2/2008 |
| WO | WO 2008/019090 | 2/2008 |
| WO | WO 2008/023783 | 2/2008 |
| WO | WO 2008/024196 | 2/2008 |
| WO | WO 2008/016692 | 3/2008 |
| WO | WO 2008/025798 | 3/2008 |
| WO | WO 2008/028937 | 3/2008 |
| WO | WO 2008/029371 | 3/2008 |

(56) References Cited

FOREIGN PATENT DOCUMENTS

| | | |
|---|---|---|
| WO | WO 2008/030843 | 3/2008 |
| WO | WO 2008/035239 | 3/2008 |
| WO | WO 2008/029306 | 5/2008 |
| WO | WO 2008/070692 | 6/2008 |
| WO | WO 2008/074820 | 6/2008 |
| WO | WO 2008/074821 | 6/2008 |
| WO | WO 2008/076243 | 6/2008 |
| WO | WO 2008/076356 | 6/2008 |
| WO | WO 2008/079382 | 7/2008 |
| WO | WO 2008/089015 | 7/2008 |
| WO | WO 2008/091967 | 7/2008 |
| WO | WO 2008/114157 | 9/2008 |
| WO | WO 2008/128832 | 10/2008 |
| WO | WO 2008/128951 | 10/2008 |
| WO | WO 2008/097819 | 11/2008 |
| WO | WO 2008/137435 | 11/2008 |
| WO | WO 2008/152149 | 12/2008 |
| WO | WO 2009/019167 | 2/2009 |
| WO | WO 2009/019506 | 2/2009 |
| WO | WO 2009/011850 | 3/2009 |
| WO | WO 2009/038974 | 3/2009 |
| WO | WO 2009/064250 | 5/2009 |
| WO | WO 2009/078983 | 6/2009 |
| WO | WO 2009/094157 | 7/2009 |
| WO | WO 2009/103552 | 8/2009 |
| WO | WO 2009/115954 | 9/2009 |
| WO | WO 2009/125434 | 10/2009 |
| WO | WO 2009/126245 | 10/2009 |
| WO | WO 2009/126535 | 10/2009 |
| WO | WO 2009/151529 | 12/2009 |
| WO | WO 2009/151621 | 12/2009 |
| WO | WO 2009/151626 | 12/2009 |
| WO | WO 2010/011316 | 1/2010 |
| WO | WO 2010/027431 | 3/2010 |
| WO | WO 2010/072703 | 7/2010 |
| WO | WO 2010/074271 | 7/2010 |
| WO | WO 2010/075239 | 7/2010 |
| WO | WO 2010/075271 | 7/2010 |
| WO | WO 2010/075273 | 7/2010 |
| WO | WO 2010/084944 | 7/2010 |
| WO | WO 2010/093704 | 8/2010 |
| WO | WO 2011/005290 | 1/2011 |
| WO | WO 2011/005295 | 1/2011 |
| WO | WO 2011/005929 | 1/2011 |
| WO | WO 2011/008663 | 1/2011 |
| WO | WO 2011/030139 | 3/2011 |
| WO | WO 2011/059784 | 5/2011 |
| WO | WO 2011/094008 | 8/2011 |
| WO | WO 2011/109471 | 9/2011 |
| WO | WO 2011/127051 | 10/2011 |
| WO | WO 2012/015758 | 2/2012 |
| WO | WO 2012/040279 | 3/2012 |
| WO | WO 2012/109108 | 8/2012 |
| WO | WO 2012/135570 | 10/2012 |
| WO | WO 2012/145361 | 10/2012 |
| WO | WO 2012/145603 | 10/2012 |
| WO | WO 2012/145604 | 10/2012 |
| WO | WO 2012/170702 | 12/2012 |
| WO | WO 2013/055910 | 4/2013 |
| WO | WO 2014/136282 | 9/2014 |
| WO | 2014/179738 A1 | 11/2014 |
| WO | 2016/100310 A1 | 6/2016 |
| WO | 2016112075 | 7/2016 |
| WO | 2016164180 | 10/2016 |
| WO | WO 2016/209809 | 12/2016 |
| WO | WO 2018/151834 | 8/2018 |
| WO | WO 2018/151873 | 8/2018 |
| WO | WO 2020/146529 | 7/2020 |

OTHER PUBLICATIONS

Lewis et. al., Inflamm. Bowel Dis. vol. 14(12), pp. 1660-1666(pp. 1-16), publ. 2008 (Year: 2008).*

Juif et. al., Expert Opin. On Drug Metab. & Tox., vol. 12(8), pp. 879-895, publ. 2016 (Year: 2016).*

Clinical Trial Protocol: APD334-011. Feb. 8, 2017, [online], [found Jun. 22, 2023]. Found from Internet: https://classic.clinicaltrials.gov/ProvidedDocs/53/NCT03072953/Prot_SAP_000.pdf(pp. 11, 32, 47).

International Patent Application No. PCT/US2019/035662, International Preliminary Report on Patentability, mailed on Issued on Dec. 8, 2020, 13 pages.

Jin, Yi, et al., "CYP4F Enzymes Are Responsible for the Elimination of Fingolimod (FTY720), a Novel Treatment of Relapsing Multiple Sclerosis", Drug Metabolism Disposition, 2011, pp. 191-198, 39(2).

Russian Patent Application No. 2020143252; filed Jun. 5, 2019; Search Report, completed Jun. 22, 2023, 3 pages.

Combes et al., "Methotrexate (MTX) plus ursodeoxycholic acid (UDCA) in the treatment of primary biliary cirrhosis," Hepatology, 2005, 42(5):1184-1193.

International Search Report and Written Opinion in International Appln. No. PCT/US2019/035662, mailed on Oct. 30, 2019, 17 pages.

Rudic et al., "Ursodeoxycholic acid for primary biliary cirrhosis," Cochrane Database of Systematic Reviews, Dec. 2012, 1-139.

Sandborn et al., "A Randomized, Double-Blind, Placebo-Controlled Trial of a Selective, Oral Sphingosine 1-Phosphate (SIP) Receptor Modulator, Etrasimod (APD334), in Moderate to Severe Ulcerative Colitis (UC): Results From the OASIS Study," The American Journal of Gastroenterology, Oct. 2018, 113:S327-S328.

"2.9.26 Specific Surface Area by Gas Adsorption," European Pharmacopoeia, 2008, 2811-2814.

Abbott et al., "Blockade of the neuropeptide Y Y2 receptor with the specific antagonist BIIE0246 attenuates the effect of endogenous and exogenous peptide YY (3-36) on food intake," Brain Res, 2005, 1043:139-144.

Abdalla et al., "Synthesis and reaction of 3-cyano 2-(1H)-pyridones," Pakistan Journal of Scientific and Industrial Research, Jun. 1977, 30(3):139-149.

Abe et al., "First Synthesis and Determination of the Absolute Configuration of Sulphostin, a Novel Inhibitor of Dipeptidyl Peptidase IV," J. Nat. Prod., 2004, 67:999-1004.

Abramovitch et al., "Solution and flash vacuum pyrolysis of some 2.6-disubstituted β-phenethysulfonyl azides and of β-styrenesulfonyl azide," J. Org Chem, 1985, 50-2066-2073.

Abstract #107, p. 56, Toward Understanding Islet Biology, Jan. 21, 2003-Jan. 26, 2003, Keystone, Colorado.

Abstract #112, p. 42, Diabetes Mellitus: Molecular Mechanisms, Genetics and New Therapies, Jan. 27, 2005-Feb. 2, 2005, Keystone, Colorado.

Abstract #117 & Poster, Diabetes: Molecular Genetics, Signaling Pathways and Integrated Physiology, Jan. 14, 2007-Jan. 19, 2007, Keystone, Colorado, 3 pages.

Abstract #228, p. 54, Diabetes Mellitus: Molecular Mechanisms, Genetics and New Therapies, Jan. 27, 2005-Feb. 2, 2005, Keystone, Colorado.

Abstract #230 & Poster, Diabetes: Molecular Genetics, Signaling Pathways and Integrated Physiology, Jan. 14, 2007-Jan. 19, 2007, Keystone, Colorado, 6 pages.

Accession No. 2003:2246299 Chemicals, IH-Pyrazolo [3,4-d] pyrimidin-4-amine, N-cyclohexyl-N-methyl-1-(3--methyphenyl)—(2003),1 page.

Accession No. 2003:2246300 Chemicals, 1H-Pyrazolo [3,4-d] pyrimidin-4-amine, N-cyclohexyl-1-(2,4-dimethlphenyl)-N-methyl—(2003), 1 page.

Accession No. 2003:2415108 Chemcats, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1, 1 page.

Accession No. 2003:2415906 Chemcats, Interbioscreen Compound Library, Chemical Name: 1H-Pyrazolo[3,4-d]pyrimidine-4-amine, N-cyclohexyl-1-1-(4-methylphenyl)-, XP-002311325, 2003, CAS Registry No. 393844-89-8, 1 page.

Accession No. 2003:2416398 Chemcats, Interbioscreen Compound Library, Chemical Name: 1H-Pyrazolo[3,4-d]pyrimidine-4-amine, N-cyclohexyl-1-1-(2,4-dimethylphenyl)-N-methyl-, XP-002311324, 2003, CAS Registry No. 393844-91-2, 1 page.

(56) References Cited

OTHER PUBLICATIONS

Accession No. 2003:2417080 Chemcats, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6, 1 page.
Actelion, Clinical Trials.gov, "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis" http://clinicaltrials.gov/ct2/show/NCT00852670, 2009.
Adams et al., "Etrasimod (APD334), an Oral, Next-Generation Sphingosine-1-Phosphate Receptor Modulator Inhibits the Development of Colitis in Lymphoid-Null Mice Injected with Colitogenic CD4+ T Cells," The FASEB Journal, Apr. 2017, 31(S1): 993.11-993.11.
Adrian et al., "Human Distribution and Release of a Putative New Gut Hormone, Peptide YY," Gastroenterol., 1985, 89(5):1070-1077.
Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," Endocrinology, 2005, 146(4):2055-2059.
Ahren et al., "Inhibition of Dipeptidyl Peptidase-4 Reduces Glycemia, Sustains Insulin Levels, and Reduces Glucagon Levels in Type 2 Diabetes," J. Clin. Endocrinol. Metab., 2004, 89:2078-2084.
Ahren et al., "Inhibition of Dipeptidyl Peptidease IV Improves Metabolic Control Over a 4-week Study Period in Type 2 Diabetes," Diabetes Care, 2002, 25:869-875.
Aidsinfo.nih.gov [online] "Dyslipidemia," Nov. 1, 2012, retrieved Jan. 22, 2014, retrieved from URL <http://aidsinfo.nih.gov/guidelines/html/2/pediatric-arv-guidelines/91/dyslipidemia>, 4 pages.
Allende et al., "Sphingosine-1-phosphate lyase deficiency produces a pro-inflammatory response while impairing neutrophil trafficking," J Biol Chem; 2011, 286:7348-58.
Ambooken et. al., "Malignant pyoderma gangrenosum eroding the parotid gland successfully treated with dexamethasone pulse therapy," Int. J. Dermatol., 2014, 53:1536-1538.
American Diabetes Association, "Dyslipidemia Prevalent in Type 2 Diabetes," Jul. 2010, http://docnews.diabetesjournals.org/content/3/3/19.1.full, retrieved on Sep. 24, 2014, 2 pages.
American Diabetes Association, "Hyperglycemia (High blood sugar)," accessed Jul. 1, 2011, http://www.diabetes.org/living-with-diabetes/treatment-and-care/blood-glucose-control/hyperglycemia.html, 1 page.
American Gastroenterological Assoc.[online], "IBD emerges as a global disease," Jan. 5, 2012, retrieved on Jan. 7, 2015, retrieved from URL <www.sciencedaily.com/releases/2012/01/120104135402.htm>, 5 pages.
American Heart Association [online], "Metabolic Syndrome," available on or before Nov. 2001, retrieved on Sep. 24, 2014, retrieved from URL <http://www.americanheart.org/pre-senter.jhtml?identifier=4756>, 3 pages.
Appukkuttan et al, "Translation-Metal-Free Sonogashira-Type Coupling Reactions in Water," European Journal of Organic Chemistry, 2003, 24-4713-4716.
Arbiser, "Why targeted therapy hasn't worked in advanced cancer," J Clinical Invest., Oct. 2007, 117(10):2762-2765.
Arehart et al, "Acceleration of Cardiovascular Disease by a Dysfunctional Prostacyclin Receptor Mutation—Potential Implications for Cyclooxygenase-2 Inhibition," Circ Res, 2008, 102:986-993.
Arena Pharmaceuticals [online], "Arena Pharmaceuticals Reports Positive Phase 2 Results from the OASIS Trial for Etrasimod in Patients with Ulcerative Colitis," Mar. 19, 2018, retrieved Mar. 21, 2022, retrieved from URL <https://invest.arenapharm.com/news-releases/news-release-details/arena-pharmaceuticals-reports-positive-phase-2-results-oasis>, 5 pages.

Arvanitis et al., "CRF Ligands via Suzuki and negishi couplings of 3-pyridyl boronic acids or halides with 2-benzyloxy-4-chloro-3-nitropyridione," Bioorganic & Medicinal Chemistry Letters, 2003, 13(2)-289-291.
Arvanitis et al., "Imidazo[4,5-b]ppyridines as corticotropin releasing factor receptor ligands," Bioorganic & Medicinal Chemistry Letters, 2003, 12(1):125-128.
Arvanitis et al., "Non-peptide corticotropin-releasing hormone antagonists; syntheses and structure-activity relationships of 2-anilinopyrimidines and triaznes," J Med Chem., 1999, 42(5):805-18.
Arvela et al., "Rapid cyanation of aryl iodides in water using microwave promotion," Org. Bio. Chem., 2003, 1:1119-1121.
Arvela et al., "Rapid, Easy Cyanation of Aryl Bromides and Chlorides Using Nickel Salts in Conjunction with Microwave Promotion," J. Org. Chem., 2003, 68:9122-9125.
Atik et al., "Burden of Osteoporosis," Clin Orthop Relat Res, 2006, 443:19-24.
Atwal et al., "Synthesis and Biological Activity of 5-aryl-4-(5-methyl-1H-imidazol-4-yl)piperidin-1-yl)pyrimidine Analogs as Potent, Highly Selective, and Orally Bioavailable NHE-1 Inhibitors," Bioorganic & Medicinal Chemistry Letters, 2006, 16(18):4796-4799.
Augustyns, et al., "Inhibitors of proline-specific dipeptidyl peptidases: DPP IV inhibitors as a novel approach for the treatment of type 2 diabetes," Expert Opin. Ther. Patents, 2005, 15:1387-1407.
Avoiding Fatal Responses to Flu Infection, ScienceDaily, http://www.sciencedaily.com/releases/2011/09/110915134410.htm, Sep. 15, 2011, 2 pages.
Bailey et al., "Interactions Between Grapefruit Juice and Cardiovascular Drugs," American Journal of Cardiovascular Drug, 2004, 4(5):281-297.
Baindur et al., "Solution-Phase Synthesis of a Library of 3,5,7-Trisubstituted 3H-[1,2,3]triazolo[4,5-Id]pyrimidines," J. Comb. Chem., 2003. 5:653-659.
Bakkestuen et al., "Regioselective N-9 arylation of purines employing arylboronic acids in presence of Cu(II)," Tetrahedron Letters, 2003, 44:3359-3362.
Balasubramaniam et al, "Neuropeptide Y (NPY) Y2 receptor-selective agonist inhibits food intake and promotes fat metabolism in mice: Combined anorectic effects of Y2 and Y4 receptor-selective agonists," Peptides, 2007, 28:235-240.
Balasubramaniam et al, "Structure-Activity Studies Including a Ψ(CH-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, 43:3420-3427.
Balatoni et al., "FTY720 sustains and restores neuronal function in the DA rat model of MOG-induced experimental autoimmunue encephalomyelitis," Brain Res. Bull., 2007, 74:307-316.
Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions," Tetrahedron, 2002, 58:7607-7611.
Bar-Haim et al., "Interrelationship between Dendritic Cell Trafficking and Francisella tularensis Dissemination following Airway Infection," PLoS Pathog., 2008, 4(11):e1000211, 15 pages.
Barta et al., "Synthesis and activity of selective MMP inhibitors with an aryl backbone," Bioorg & Med Chem Ltrs, 2000, 10(24):2815-2817.
Baskin et al., "A mild, convenient synthesis of sulfinic acid salts and sulfonamides from alkyl and aryl halides," Tetrahedron Letters, 2002, 43:8479-8483.
Baskin et al., "An Efficient Copper Catalyst for the Formation of Sulfones from Sulfinic Acid Salts and Aryl Iodides," Org. Lett., 2002, 4(25):4423-4425.
Batterham et al, "Gut hormone PYY3-36 physiologically inhibits food intake," Nature, 2002, 418:650-654.
Baumruker et al., "FTY720, an immunomodulatory sphingolipid mimetic: translation of a novel mechanism into clinical benefit in multiple sclerosis," Expert Opin. Investig. Drugs, 2007, 16(3):283-289.
Bayes et al., "Apolipoprotein E alleles, Dyslipemia, and Kidney Transplantation", Transplantation Proceedings, 2002, 34(1):373.

(56) References Cited

OTHER PUBLICATIONS

Becalski et al., "Synthesis of carbolines by the Graebe-Ullmann method," Acta Pol Pharm., 1977, 41:601-606.
Bedford et al., "Nonquaternary Cholinesterase Reactivators. 3.3(5)-Substituted 1,2,4-Oxadiazol-5(3)-Aldoximes And 1,2,4-Oxadiazole-5(3)-Thiocarbohydroximates As Reactivators Of Organophsphonate-Inhibited Eel And Hunan Acetylcholinesterase In Vitro," J Med Chem, 1986, 29(11):2174-2183.
Behre, "Adiponectin, obesity and atherosclerosis," Scand J Clin Lab Invest, 2007, 67:449-458.
Beller et al., "Based-catalyzed amination of olefins; an example of an environmentally friendly synthesis of amines," Chemosphere, 2001, 43(1):21-26.
Bergasa et. al., "Pruritus and fatigue in primary biliary cirrhosis," Best Practice & Research Clinical Gastroenterology, Aug. 2000, 14(4):643-655.
Berge et al., "Pharmaceutical Salts," J Pharma Sci., 1977, 66(1):1-19.
Betti, et al., "Novel 3-Aralkyl-7 (amino-substituted)-1,2,3-triazole[4,5-d]primidines with High Affinity toward A1 Adenosine Receptors," J. Med. Chem, 1998, 41:668-673.
Bhatt and Thakkar, "Preparation and study of a nickel(II) ion selective electrode," Indian J. Chem, May 1994, 33A:436-437.
Biagi et al, "Synthesis of 4,6-Disubstituted- and 4,5,6-trisubstituted 2-phenyl-pyrimidines and their affinity towards A1 adenosine receptors," Farnaco, 1997, 52(1):61-65.
Bilchik et al, "Peptide YY is a Physiological Regulator of Water and Electrolyte Absorption in the Canine Small Bowel in Vivo," Gastroenterol., 1993, 105:1441-1448.
Biopharmatiques, "Merging Pharma and Biotech", http://www.biopharmaceutiques.com/fr/tables/clinical_studies_709.html, 2009, 1 page.
Boey et al, "Peptide YY ablation in mice leads to the development of hyperinsulinaemia and obesity," Diabetologia, 2006, 49:1360-1370.
Boey et al, "PYY transgenic mice are protected against diet-induced and genetic obesity," Neuropeptides, 2008, 42:19-30.
Boismenu et al., "Insights from mouse models of colitis," K. Leukoc Biol, 67:267-278, 2000.
Bol'but, et al., "A new synthetic approach to fused pyrimidin-4-ones", Institute of Organic Chemistry, National Academy of Sciences of Ukraine, 2003, accessed Mar. 30, 2008, http://conf.iflab.kiev.ua/eng/reports/show/?id=348, 2 pages (Abstract).
Boldt et al, "Simple Synthesis of 2,4-diaminopyridines," Angewandte Chemie International Edition, 1970, 5 pages.
Bolick et al., "Sphingosine-1-Phosphate Prevents Tumor Necrosis Factor-alpha-Mediated Monocyte Adhesion to Aortic Endothelium in Mice," Arterioscler. Thromb. Vasc. Biol., 2005, 25:976-981.
Bollag et al., "Glucose-dependent insulinotropic peptide is an integrative hormone with osteotropic effects," Mol Cell Endocrinol, 2001, 177:35-41.
Bollag et al., "Osteoblast-Derived Cells Express Functional Glucose-Dependent Insulinotropic Peptide Receptors," Endocrinology, 2000, 141:1228-1235.
Bomika et al, "Some Nucleophilic Substitution Reactions of 2-Chloro-3-Cyanopyridines," Khimiya Geterotsiklicheskikh Soedinenii, Aug. 1976, 8:1085-1088 (Translated pp. 896-899).
Boschelli et al, "1,3,4-Oxadiazole, 134-thiadiazole, and 1,3,4-triazole analogs of the fenamates: in vitro inhibition of cyclooxygenase and 5-Lipoxygenase activities," J Med Chem, 1953, 36:1802-1810.
Boswell et al, "Synthesis of Some N-carboxylic acid derivatives of phenoxypyrrolidines, 4-phenoxypiperidines, and 3-phenoxynortropanes with muscle relaxant and anticonvulsant activities," J Med Chem, 1974, 17(9):100-1008.
Bradley, "TNF-mediated inflammatory disease," J Pathol, 2008, 214:149-160.
Brancati et al., "Body Weight Patterns from 20 to 49 Years of Age and Subsequent Risk for Diabetes Mellitus," Arch. Intern. Med., 1999, 159:957-963.

Breuer, "Hypertriglyceridemia: A Review of Clinical Relevance and Treatment Options: Focus on Cerivastatin," Current Medical Research and Opinion, 2001, 17(1):60-73.
Brewer, "Benefit-Risk Assessment of Rosuvastatin 10 to 40 Milligrams," American Journal of Cardiology, 2003, 92(4B):23K-29K.
Brinkman, "Sphingosine 1-phosphate receptors in health and disease: Mechanistic insights from gene deletion studies and reverse pharmacology," Pharmacol. Ther., 2007, 115:84-105.
Brinkmann et al., "Fingolimod (FTY720): discovery and development of an oral drug to treat multiple sclerosis," Nat Rev Drug Discov, Nov. 2010; 9(11):883-97.
Brinkmann et al., "FTY720 Alters Lymphocyte Homing and Protects Allografts Without Inducing General Immunosuppression," Transplantation Proc., 2001, 33:530-531.
Brinkmann et al., "FTY720: Altered Lymphocyte Traffic Results in Allograft Protection," Transplantation, Sep. 2001, 72(5):764-769.
Brinkmann et al., "The Immune Modulator FTY720 Targets Sphingosine 1-Phosphate Receptors," J Biol. Chem., 2002, 277(24):21453-21457.
Brinkmann, "FTY720 (fingolimod) in Multiple Sclerosis: therapeutic effects in the immune and the central nervous system", British Journal of Pharmacology, 158: 1173-1182, 2009.
Bromidge et al., "Design of [R-(Z)-]-(+)-α-(methoxylmino)-lazabicyclo[2.2.2]octane-3-acetonitri le (SB 202026), a functionally selective azabicyclic muscarinic M1 against incorporating the N-methoxy imidoyl nitrile group as a novel ester bioisostere," J Med Chem, 1997, 40(26):4265-4280.
Brossard et al., "Pharmacokinetics and pharmacodynamics of ponesimod, a selective S1P1 receptor modulator, in the first-in-human study," British Journal of Clinical Pharmacology, Dec. 2013, 76(6):888-896.
Brunauer et al., "Adsorption of Gases in Multimolecular Layers," J. Am. Chem. Soc., Feb. 1938, 60(2):309-319.
Brunsting et al. "Pyoderma (Echthyma) Gangrenosum Clinical and Experimental Observations in Five Cases Occurring in Adults," Arch Dermatol Syph, 1930, 22:655-680.
Budde et al., "First Human Trial of FTY720, a Novel Immunomodulator, in Stable Renal Transplant Patients," J Am Soc. Nephrol., 2002, 13:1073-1083.
Buehler et al, "Physiologically active compounds. VI. Cyclic amino thiolesters of substituted chloracetic, benzilic and glycolic acids," J Med Chem, 1965, 8:643-647.
Bulger et al., "An investigation into the alkylation of 1,2,4-triazole," Tetrahedron Letters, 2000, 41:1297-1301.
Burisch et al., "The burden of inflammatory bowel disease in Europe," J Crohns Colitis., 2013, 7(4):322-37.
Buzard, Daniel J. et al, "Recent Progress in the Development of Selective S1P1 Receptor Agonists for the Treatment of Inflammatory and Autoimmune Disorders", Expert Opinion, 1141-1159, 2008.
Buzard et al., "Discovery of APD334: design of a clinical stage functional antagonist of the sphinogosine-1-phosphate-1 receptor," ACS Med. Chem. Lett., 2014, 5(12):1313-1317.
Buzard et al., "Discovery and Characterization of Potent and Selective 4-Oxo-4-(5-(5-phenyl-1,2,4-oxadiazol-3-yl)indolin-1-yl)butanoic acids as S1P1 Agonists", Biorganic Med. Chem. Lett., 2011, 6013-6018.
Buzard, Daniel J. et al., "Discovery and Characterization of Potent and Selective 4-Oxo-4-(5-(5-phenyl-1,2,4-oxadiazol-3-yl)indolin-1-yl)butanoic acids as S1P1 Receptor Agonists", Arena Pharmaceuticals, Inc., MEDI099, ACS, Mar. 2011, 1 page.
Caldwell et al., "Fluoropyrrolidine amides as dipeptidyl peptidase IV inhibitors," Bioorg. Med.Chem. Lett., 2004, 14:1265-1268.
Capuzzi et al., "Beneficial effects of rosuvastatin alone and in combination with extended-release niacin in patients with a combined hyperlipidemia and low high-density lipoprotein cholesterol levels," American Journal of Cardiology, 2003, 91(11):1304-1310.
Capuzzi et al., "Rosuvastatin Alone or With Extended-Release Niacin: A New Therapeutic Option for Patients With Combined Hyperlipidemia," Preventive Cardiology, Fall 2004, 7(4):176-181.
Carswell et al., "Rosuvastatin," Drugs, 2002, 62(14):2075-2085.

(56) References Cited

OTHER PUBLICATIONS

Centers for Disease Control and Prevention [online], "Inflammatory bowel disease (IBD)," last reviewed Mar. 14, 2017, retrieved on Aug. 20, 2019, retrieved from URL <https://www.cdc.gov/ibd/>, 2 pages.
Chan et al., "Isoquinoline-6-Carboxamides as Potent and Selective Anti-Human Cytomegalovirus (HCMV)Inhibitors," Bioorganic & Medicinal Chemistry Letters, 1999, 9:2583-2586.
Chapman et al., "Non-High-Density Lipoprotein Cholesterol as a Risk Factor: Addressing Risk Associated with Apolipoprotein B-Containing Lipoproteins," European Heart Journal Supplements, 2004, 6(Suppl. A):A43-A48.
Chapoulaud et al., "Synthesis of 4,8-Diarylcinnolines and Quinazolines with Potential Applications in Nonlinear Optics. Diazines. Part 28," Tetrahedron (2000) 56:5499-5507.
Chaudhri et al, "Gastrointestinal Satiety Signals," Annu Rev Physiol, 2008, 70:239-255.
Chawla et al., Challenges in Polymorphism of Pharmaceuticals, CRIPS, Jan.-Mar. 2004, vol. 5, No. 1, 4 pages.
Chen et al., "Design and Synthesis of a Series of Non-Peptide High-Affinity Human Corticotropin-Releasing Factor1 Receptor Antagonists," J Med. Chem., 1996, 39:4358-4360.
Chen et al., "Free Radical Method for the Synthesis of Spiro-Piperidinyl Heterocycles," Tetrahedron Letters, 1996, 37(3):5233-5234.
Chen et al., "Inhibitory Effect of Candesartan and Rosuvastatin on CD40 and MMPs Expression in Apo-E Knockout Mice: Novel Insights into the Role of RAS and Dyslipidemia in Atherogenesis," Journal of Cardiovascular Pharmacology, 2004, 44(4):446-452.
Chen et al., "Optimization of 3-phyenylprazolo[1,5-alpha]pyrimidines as potent corticotrophin-releasing factor-I antagonists with adequate lipophilicity and water solubility," Bioorganic & Medicinal Chemistry Letters, 2004, 14:3669-3673.
Chen et al., "Synthesis and Oral Efficacy of a 4-(Bulylethylamino)pyrrolo[2,3-d]pyrimidine: A Centrally Active Corticotropin-Releasing Factor: Receptor Antagonist," J. Med. Chem., 1997, 40:1749-1754.
Cheng and Robins, "Potential purin antagonists. VI. Synthesis of 1-alkyl and 1-aryl-4-substituted pyrazolo[3,4-d]pyrimidines," J. Org Chem, 1956, 21:1240-1256.
Cheng, "Rosuvastatin in the Management of Hyperlipidemia," Clinical Therapeutics, 2004, 26(9):1368-1387.
Cheng-Lai, "Cerivastatin," Heart Disease, 2000, (2):93-99.
Cheng-Lai, Rosuvastatin; A New HMG-CoA Reductase Inhibitor for the Treatment of Hypercholesterolemia; Heart Disease, 5(1), 72-78 (2003).
Cheung et. al., "Combined ursodeoxycholic acid (UDCA) and fenofibrate in primary biliary cholangitis patients with incomplete UDCA response may improve outcomes," Aliment Pharmacol Ther., Nov. 2015, 43(2):283-293.
Chiba et al., "Role of Sphingosine 1-Phosphate Receptor Type 1 in Lumphocyte Egress from Secondary Lymphoid Tissues and Thymus," Cell Mole Immunol., Feb. 2006, 3(1):11-19.
Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.
Chorvat et al,, "Synthesis, Corticotropin-Releasing Factor Receptor Binding Affinity, and Pharmacokinetic Properties of Triazolo-, Imidazo-, and Pyrrolopyrimidines and -pyridines," J. Med. Chem., 1999. 42:833-848.
Chu et al., "A Role for Intestinal Endocrine Cell-Expressed GPR119 in Glycemic Control by Enhancing GLP-1 and Glucose-Dependent Insulinotropic Peptide Release," Endocrinology, 2008, 149(5):2038-2047.
Chu et al., "A role for β-cell-expressed G protein-coupled receptor 119 in glycemic control by enhancing glucose-dependent insulin release," Endocrinology, 2007, 148:2601-2609.
Chu, "Section 1: Drug Development," Cancer: Principles and Practice of Oncology, 2005, Lippincott Williams & Wilkins, 27 pages.

Chun et al., "International Union of Pharmacology. XXXIV. Lysophospholipid Receptor Nomenclature," Pharmacol. Rev., 2002, 54(2):256-269.
Citkowitz, "Hypertriglyceridemia," eMedicine Endorinology, Jul. 2008, http://emedicine.medscape.com/article/126568-print, retrieved on Sep. 24, 2014, 18 pages.
Clark et al., "Synthesis and Analgesic Activity of 1,3-Dihydro-3-(Substituted phenyl)imidazo(4,5-b]pyridine-2-ones and 3-(Substituted phenyl)-1,2,3-triazolo(4,5bpyridines," J. Med. Chem., 1978, 21(9):965-978.
Clark, "Treating Dyslipidemia with Statins: The Risk-Benefit Profile," American Heart Journal, 2003, 145(3):387-396.
Cleveland Clinic [online], "Metabolic Syndrome," Dec. 2009, retrieved on Sep. 24, 2014, retrieved from URL <http://my.clevelandclinic.org/disorders/metabolic_syndrome/hic_metabolic_syndrome.aspx>, 2 pages.
Clinical Trials [online], "Efficacy and Safety of Etrasimod (APD334) in Inflammatory Bowel Disease Patients With Active Skin Extraintestinal Manifestations," Dec. 31, 2020, Retrieved Jan. 25, 2022, retrieved from URL <https://clinicaltrials.gov/ct2/show/NCT03139032?term=etrasimod&draw=3&rank=13>, 32 pages.
Cocco et al., "Transformation of 6-Methylthiopyrimidines. Preparation of New Pyrimidine Derivatives and Fused Azolopyrimidines," Journal of Heterocyclic Chemistry, 2000, 37(4):707-710.
Cocuzza et al, "Use of the suzuki reaction for the synthesis of aryl-substituted heterocycles as corticotropin-releasing hormone (CRH) antagonists," Bioorganic & Medicinal Chemistry Letters, 1999, 9:1063-1066.
Coelho et al., "The Immunomodulator FTY720 bas a direct cytoprotective effect in oligodendrocyte Progenitors," J Pharmacol. Exp. Ther., 2007, 323:626-635.
Cohen et al., "The Preparation and Properties of 6-Halomethylpurines," Div. of Nucleoprotein Chemistry, Sloan-Kettering Institute for Cancer Research, and Sloan Kettering Div. Grad. School of Med. Sci., Cornell Univ. Med. College, 1962, 27:3545-3549.
Cohen, "Neutrophilic dermatoses: a review of current treatment options," Am J Clin Dermatol., 2009, 10(5):301-12.
Colandrea et al., "Synthesis and regioselective alkylation of 1,6-and 1,7-naphythridines," Tetrahedron Letters, 2000, 41:8053-8057.
Collier et al, "Radiosynthesis and In-vivo Evaluation of the Psuedopeptide 8-pioid Antagonist [125I]-ITIPP(Ψ)," J. Labelled Compd. Radiopharm., 1999, 42, S264-S266.
Cossey et al, "Pyridines and pyridinium salts from cyanoacetamides," Australian Journal of Chemistry, 1976, 29(5):1039-1050.
Coste et al., "Antinociceptive activity of the S1P-receptor agonist FTY720," J Cell Moll Med., 2008, 12(3):995-1004.
Cover Sheet and 23 Compounds, ChemCats file, 11 pp., (2006).
Cover Sheet and 1185 Compounds, CAS Registry and ChemCats files, 391 pp., (various dates—Jan. 12, 2005-Nov. 10, 2006).
Cover Sheet and 18 Compounds, CAS Registry, 9 pp., (various dates—Aug. 1, 2004-Jan. 13, 2005).
Cover Sheet and 2534 Compounds, CAS Registry and ChemCats files, 817 pp., (various dates—Feb. 7, 2006-Nov. 6, 2006).
Cover Sheet and 54 Compounds, CAS Registry and ChemCats files, 23 pp., (various dates—Jan. 15, 1998-Jun. 16, 2004).
Cox, "Peptide YY: A neuroendocrine neighbor of note," Peptides, 2007, 28:345-351.
Crohn's and Colitis Foundation of America. The Facts About Inflammatory Bowel Diseases. Nov. 2014, New York, NY 10017. http://www.ccfa.org/assets/pdfs/ibdfactbook.pdf. Accessed Jan. 7, 2015.
Crosby et al., "030 Etrasimod, an oral, selective sphingosine 1-phosphate receptor modulator improves skin inflammation in a contact hypersensitivity dermatitis model," Journal of Investigative Dermatology, 2019, 139(9):Supplement 219, 1 page.
Crouse, et al., "Measuring Effects on Intima Media Thickness: An Evaluation of Rosuvastatin in Subclinical Atherosclerosis—The Rationale and Methodology of the METEOR Study," Cardiovascular Drugs and Therapy, 2004, 18(3):231-238.
Cruze et al, "The Y2 receptor mediates increases in collateral-dependent blood flow in a model of peripheral arterial insufficiency," Peptides, 2007, 28:269-280.

(56) References Cited

OTHER PUBLICATIONS

Cryan et al, "Behavioral characterization of the novel GABAB receptor-positive modulator GS39783 (N,N'-dicyclopentyl-2-methylsulfanyl-5-nitro-pyrimidine-4,6-diamine): anxiolytic-like activity without side effects associated with baclofen or benzodiazepines," Journal of Pharmacology and Experimental Therapeutics, 2004, 310(3):952-963.

Dai et al., "The First General Method for Palladium-Catalyzed Negishi Cross-Coupling of Aryl and Vinyl Chlorides: Use of Commercially Available Pd(P(t-Bu)3)2 as a Catalyst," J. Am. Chem. Soc., 2001, 123(12):2179-2724.

D'Ambrosio et al., "Ponesimod, a selective S1P1 receptor modulator: a potential treatment for multiple sclerosis and other immune-mediated diseases," Therapeutic Advances in Chronic Disease, 2016, 7(1):18-33.

Danese et al., "Ulcerative colitis," N Engl J Med, 2011, 365(18):1713-1725.

Daniel et al., "FTY720 Ameliorates Th1-Mediated Colitis in Mice by Directly Affecting the Functional Activity of DC4+CD25+ Regulatory T Cell1," J Immunol., 2007, 178:2458-2468.

Davidson, "Rosuvastatin: A Highly Efficacious Statin for the Treatment of Dyslipidemia," Expert Opinion on Investigational Drugs, 2002, 11(3):455.

De Denus et al., "Dyslipidemias and HMG-CoA Reductase Inhibitor Prescription in Heart Transplant Recipients," Annals of Pharmacotherapy, 2004, 28 (7/8):1136-1141.

Deacon et al, "Degradation of Endogenous and Exogenous Gastric Inhibitory Polypeptide in Healthy and in Type 2 Diabetic Subjects as Revealed Using a New Assay for the Intact Peptide," The Journal of Clinical Endocrinology & Metabolism, 2000, 85:3575-3581.

Deacon, "Therapeutic Strategies Based on Glucagon-Like Peptide 1," Diabetes, Sep. 2004, 53:2181-2189.

Deacon, "What do we know about the secretion and degradation of incretin hormones?" Regul Pept, 2005, 128:117-124.

Deguchi et al., "The S1P receptor modulator FTY720 prevents the development of experimental colitis in mice," Oncol. Rep., 2006, 16:699-703.

Deighan, et al., "Comparative Effects of Cerivastatin and Fenofibrate on the Atherogenic Lipoprotein Phenotype in Proteinuric Renal Disease," Journal of the American Society of Nephrology, 2001, 12(2):341-348.

Delmas and Meunier, "The Management of Paget's Disease of Bone," The New England Journal of Medicine, Feb. 1997, 336: 558-566.

Demuth et al., "Type 2 diabetes—Therapy with dipeptidyl peptidase IV inhibitors," Biochimica et Biophysica Acta (BBA), 2005, 1751(1):33-44.

Desimoni et al, "Polynuclear Isoxazole Types-I-Isoxazolo[4,5-d]Pyrimidines," Tetrahedron, 1967, 23:675-680.

Dev et al., "Brain sphingosine-1-phosphate receptors: Implication for FTY720 in the treatment of multiple sclerosis," Pharmacol Ther., 2008, 117:77-93.

Devita et al, "Identification and initial structure-activity relationships of a novel non-peptide quinolone GnRH receptor antagonist," Bioorg & Med Chem Ltrs, 1999, 9(17):2615-2620.

Di Braccio et al., "Synthesis and preliminary pharmacological examination of 2,4-disubstituted N,N-dialkyl-1,8-napthyridine-3-carboxamides," Farmaco (1989) 44(9):865-881.

Dillmann et al., "S1PR4 Signaling Attenuates ILT 7 Internalization To Limit IFN-α Production by Human Plasmacytoid Dendritic Cells," J Immunol., 2016, 15;196(4):1579-90.

Ding et al., "A Combinatorial Scaffold Approach toward Kinase-Directed Heterocycle Libraries" J. Am. Chem. Soc. (2002) 124:1594-1596.

Dorwald, Side Reactions in Organic Synthesis, 2005, Wiley (Table of Contents Only).

Drucker et al., "The incretin system: glucagon-like peptide-1 receptor agonists and dipeptidyl peptidase-4 inhibitors in type 2 diabetes," The Lancet, 2006, 368:1696-1705.

Drucker, "The biology of incretin hormones," Cell Metabolism, 2006, 3:153-165.

Dubau-Assibat et al., "Lawesson's Reagent: An Efficient 1,3-Dipole Trapping Agent", J. Org. Chem., 1995, 60(12):3904-3906.

Dugue et al., "Detection and Incidence of Muscular Adverse Drug Reactions: A prospective Analysis from Laboratory Signals," European Journal of Clinical Pharmacology, 2004, 60(4):285-292.

During et al., "Glucagon-like peptide-1 receptor is involved in learning and neuroprotection," Nat. Med., 2003, 9:1173-1179.

Dzierba et al., "Synthesis, Structure-Activity Relationships, and in Vivo Properties of 3,4-Dihydro-1H-pyrido[2,3-b]pyrazin-2-ones as Corticotropin-Releasing Factor-1 Receptor Antagonists," Journal of Medicinal Chemistry, 2004, 47(23):5783-5790.

Eberlein et al, "A New Molecular Form of PYY: Structural Characterization of Human PYY (3-36) and PYY(1-36)," Peptides, 1989, 10:797-803.

Edmondson et al., "Potent and selective proline derived dipeptidyl peptidase IV inhibitors," Bioorg. Med. Chem. Lett., 2004, 14:5151-5155.

Eicher et al., "Reaction of Triafulvenes with Isonitriles. A simple synthesis of diphenyl-substituted functionalized cyclobutene derivatives and related products," Synthesis (1987)(7):619-626.

Ekblad et al, "Distribution of pancreatic polypeptide and peptide YY," Peptides, 2002, 23:251-261.

Ekstrand et al, "Deletion of neuropeptide Y (NPY) 2 receptor in mice results in blockage of NPY-induced angiogenesis and delayed wound healing," PNAS USA, 2003, 100:6033-6038.

El Bahh et al, "The anti-epileptic actions of neuropeptide Y in the hippocampus are mediated by Y2 and not Y5 receptors," Eur. J. Neurosci., 2005, 22:1417-1430.

emedicinehealth.com [online], "High Blood Sugar" available on or before Jan. 23, 2016, via Internet Archive: Wayback Machine URL <http://web.archive.org/web/2016*/http://www.emedicinehealth.com/high_blood_sugar_hyperglycemia/page9_em.htm>, retrieved on Jul. 1, 2011, URL<http://www.emedicinehealth.com/high_blood_sugar_hyperglycemia/page9_em.htm>, 2 pages.

Escher et al, "Cyclopentylamine Substituted Triazolo[4,5-D]Pyrimidine: Implications for Binding to the Adenosine Receptor," Tetrahedron Letters (1991) 32(29):3583-3584.

Estel et al., "Synthesis Of Ortho-Substituted Aminopyridines. Metalation Of Pivaloylamino Derivatives," J. Heterocyclic Chem., 1989, 26:105-112.

Fellstrom, et al, "Why Do We Need a Statin Trial in Hemodialysis Patients?" Kidney International Supplement, 2003 63(84):S204-S206.

Feng et al., "Research Progress on Extraintestinal Manifestations of Inflammatory Bowel Disease," Journal of Gastroenterology and Hepatology, 2015, 24(6):631-640 (with English abstract).

Fenofibrate Prescribing Information, Revised Nov. 2018, 19 pages.

Fischer et al., "What rheumatologists can learn from gastroenterologists," Zeitschrift für Rheumatologie, 2018, 77(6):460-468, 10 pages (with English abstract).

Fischer et al., "Targeting receptor tyrosine kinase signalling in small cell lung cancer (SCLC): What have we learned so far?" Cancer Treatment Revs., 2007, 33:391-406.

Flock et al., "GPR119 Regulates Murine Glucose Homeostasis Through Incretin Receptor-Dependent and Independent Mechanisms," Endocrinology, Feb. 2011, 152(2):374-383.

Freling et al., "Cumulative incidence of, risk factors for, and outcome of dermatological complications of anti-TNF therapy in inflammatory bowel disease: a 14-year experience," Am J Gastroenterol, 2015, 110:1186-1196.

Fu et al., "Long-term islet graft survival in streptozotocin- and autoimmune-induced diabetes models by immunosuppressive and potential insulinotropic agent FTY720," Transplantation, May 2002, 73(9):1425-1430.

Fujii et al., "FTY720 suppresses CD4+CD44highCD62L-effector memory T cell-mediated colitis," Am J Physiol Gastrointest Liver Physiol., 2006, 291:G267-G274.

Fujino et al., "Amelioration of experimental autoimmune encephalomyelitis in Lewis rats by FTY720 treatment," J Pharmacol. Exp. Ther., 2003, 305(1):70-77.

(56) References Cited

OTHER PUBLICATIONS

Fujishiro et al., "Change from Cyclosporine to Combination Therapy of Mycophenolic Acid with the New Sphinogosine-1-phosphate Receptor Agonist, KRP-203, Prevents Host Nephrotoxicity and Transplant Vasculopathy in Rats," J Heart Lung Transplant, 2006, 25:825-833.
Fyfe et al. "GPR119 agonists as potential new oral agents for the treatment of type 2 diabetes and obesity," Expert Opinion on Drug Discovery, 2008, 3(4):403-413.
Fyfe et al., "GPR119 Agonists Are Potential Novel Oral Agents for the Treatment of Diabesity," Diabetes, 2007, 56(1):A142 (Abstract).
Gabriel et al., "High throughput screening technologies for direct cyclic AMP measurement", ASSAY and Drug Development Technologies, 2003, 1(2):291-303.
Gameiro et al., "Pyoderma gangrenosum: challenges and solutions" Clin. Cos. Inv. Dermatol, 2015, 8:285-293.
Gangloff et al., "Synthesis of 3,5-disubstituted-1,2,4-oxadiazoles using tetrabutylammonium fluoride as a mild and efficient catalyst," Tetrahedron Letters, 2001, 42:1441-1443.
Garcia, et al., "Effects of Cerivastatin in Dyslipemia and Other Cardiovascular Risk Factors after Renal Transplantation," Transplantation Proceedings, 2002, 34(1),:401-402.
GeneMedRX [online], "Cytochrome P-450 (CYP) Metabolism Reference Table," available on or before Nov. 8, 2017, via Internet Archive: <https://web.archive.org/web/20171108224330/http://www.genemedrx.com/Cytochrome_P450 Metabolism_Table.php>, retrieved on Mar. 23, 2022, URL <http://www.genemedrx.com/Cytochrome_P450_Metabolism_Table.php>, 3 pages.
Gergely et al., "The selective sphingosine 1-phosphate receptor modulator BAF312 redirects lymphocyte distribution and has species-specific effects on heart rate," British J of Pharm, 2012, 167(5):1035-1047.
Gewald and Bellmann, "Synthese und Reaktionen von 4-Aminoisothiazolen," Liebigs Annalen der Chemie, 1979, 10:1534-1546.
Gilligan et al., "Corticotropin-releasing factor antagonists: Recent advances and exciting prospects for the treatment of human diseases," Current Opinion in Drug Discovery & Development, 2004, 7(4):487-497.
Gilligan, et al., "Corticotropin Releasing Factor (CRF) Receptor Modulators: Progress and Opportunities for New Therapeutic Agents," J. Med. Chem, 2000, 43(9):1641-1660.
Giner-Sorolla et al., "The Synthesis and Properties of 6-Mercaptomethylpurine and Derivatives," Cornell University Medical College, 1965, 8:667-672.
Girouard and Iadecola, "Neurovascular coupling in the normal brain and in hypertension, stroke and Alzheimer disease," J. Appl. Physiol., 2006, 100:328-335.
Goldner et al., "Die Darstellung 2, 9-; 2,6,9- and 6,9-substituierter Purine," Journal fuer Praktische Chemie (Leipzig), 1961, 12:242-252.
Golub et al., "Molecular Classification of Cancer: Class Discovery and Class Prediction by Gene Expression Monitoring," Science, 1999, 286:531-537.
Gomez et al., "Intestinal peptide YY: ontogeny of gene expression in rat bowel and trophic actions on rat and mouse bowel," Am. J. Physiol., 1995, 268:G71-G81.
Gomtsyan et al., "Design, synthesis, and structure-activity relationship of 6-alkynylpyrimidines as potent adenosine kinase inhibitors," J Med Chem. (2002) 45(17):3639-3648.
Gonon et al, "Adiponectin protects against myocardial ischaemia-reperfusion injury via AMP-activated protein kinase, Akt, and nitric oxide," Cardiovasc Res., 2008, 78:116-122.
Gottlieb, et al., "NMR Chemical Shifts of Common Laboratory Solvents as trace Impurities," J. Org. Chem. 1997, 62, 7512-7515.
Grandt et al, "Two molecular forms of Peptide YY (PYY) are abundant in human blood: characterization of a radioimmunoassay recognizing PYY 1-36 and PYY 3-36," Regul. Pept., 1994, 51:151-159.

Greig et al., "New Therapeutic Strategies and Drug Candidates for Neurodegenerative Diseases: p53 and TNF-α Inhibitors, and GLP-1 Receptor Agonists," Ann NY Acad Sci, 2004, 1035:290-315.
Griesser, "The Importance of Solvates" in Polymorphism in the Pharmaceutical Industry, 211-233 (Rolf Hilfiker, ed., 2006).
Grise et al, "Peptide YY Inhibits Growth of Human Breast Cancer in Vitro and in Vivo," J. Surg. Res., 1999, 82:151-155.
Groeneveld, "Vascular pharmacology of acute lung injury and acute respiratory distress syndrome," Vascular Pharmacol., 2003, 39:247-256.
Groger "Moderne methoden der Suzuki-kreuzkupplung: die langerwarteten universellen synthesevarianten mit arylchloriden," J Prakt Chem, 2000, 342(4):334-339 (English Abstract).
Guerre-Millo, "Adiponectin: An Update," Diabetes & Metabolism, 2008, 34:12-18.
Guerrero et al., "Sphingosine 1-phosphate receptor 1 agonists: a patent review (2013-2015)," Expert Opinion on Therapeutic Patents, 2016, 26(4):455-470, 41 pages.
Guilherme et al., "Adipocyte dysfunctions linking obesity to insulin resistance and type 2 diabetes," Molecular Cell Biology, May 2008, 9:367-377.
Guillory, "Generation of Polymorphs, Hydrates, Solvates, and Amorphous Solids," in: Polymorphism in Pharmaceutical Solids, ed. Harry G.Brittan, vol. 95, Marcel Dekker, Inc. New York, 1999, pp. 202-209.
Gundersen "Synthesis of purinecarbonitriles by Pd(0)-catalysed coupling of halopurines with zinc cyanide," Acia Chemica Scandinavia (1996) 50:58-63.
Hafenbradl et al., "In vitro Characterization of Small-Molecule Kinase Inhibitors," Protein Kinase as Drug Targets, 2011 (B. Kiebl et al. eds) 185 pages.
Hale et al., "Potent S1P receptor agonists replicate the pharmacologic actions of the novel immune modulator FTY720," Bioorganic Med Chem. Lett., 2004, 14:3351-335.
Hamada et al., "An Improved Synthesis Of Arylsulfonyl Chlorides From Aryl Halides," Synthesis, 1986, 852-854.
Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI 098, ACS Poster, Mar. 2011, 1 page.
Hansmann et al, "Pulmonary Arterial Hypertension is Linked to Insulin Resistance and Reversed by Peroxisome Proliferator-Activated Receptor-γ Activation," Circulation, 2007, 115:1275-1284.
Hara et al, "Measurement of the High-Molecular Weight Form a Adiponectin in Plasma is Useful for the Prediction of Insulin Resistance and Metabolic Syndrome," Diabetes Care, 2006, 29:1357-1362.
Hay et al, "Inflammatory Bowel Disease: Costs-of-Illness," J Clin Gastroenterol, 1992, 14:309-317.
He et al., "4-(1,3-Dimethozyprop-2-ylamino)-2,7-dimethyl-8-(2,4-dichlorophenyl)-pyrazolo[1,5-al-1,3,5-triazine: A Potent, Orally Bioavailable CRF1 Receptor Antagonist," J. Med. Chem., 2000, 43:449-456.
Hecht et al., "On the 'activation' of cytokins," J Biological Chemistry, 1975, 250(18):7343-7351.
Hersperger et al., "Palladium-Catalyzed Cross-Coupling Reactions for the Synthesis of 6,8-Disubstituted 1,7-Napbthyridines: A Novel Class of Potent and Selective Phosphodiesterase Type 4D Inhibitors," J. Med. Chem., 2000, 43:675-682.
Herzinger et al., "Sphingosine-1-Phosphate Signaling and the Skin," Am J Clin Dermatol., 2007, 8(6):329-336.
Hill and Peters, "Environmental Contributions to the Obesity Epidemic," Science, 1998, 280:1371-1374.
Hinchcliff et al., "Systemic Sclerosis/Scleroderma: A Treatable Multisystem Disease," Am Fam Physician, Oct. 2008, 78(8):961-968.
Hocek et al., "An Efficient Synthesis of 2-Substituted 6-Methylpurine Bases and Nucleosides by Fe- or Pd-Catalyzed Cross-Coupling Reactions of 2,6-Dichloropurines," J. Org. Chem., 2003, 68:5773-5776.

(56) References Cited

OTHER PUBLICATIONS

Holdgate et al., "Molecular Mechanism for Inhibition of 3-hydroxy-3-methy glutaryl CoA (HMG-CoA) Reductase by Rosuvastatin," Biochemical Society Transactions, 2003, 31(3):528-531.
Huang et al., "Synthesis and Antiplatelet Activity of Phenyl Quinolones," Bioorganic & Medicinal Chemistry, 1998, 6:1657-1662.
Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.
Idzko et al., "Local application of FTY720 to the lung abrogates experimental asthma by altering dendritic cell function," J Clinc Invest., Nov. 2006, 116(11):2935-2944.
International Standard, "Determination of the specific surface area of solids by gas adsorption—BET method," 2010, Second Edition, 1-24.
Irwin et al., "Therapeutic potential of the original incretin hormone glucose-dependent insulinotropic polypeptide: diabetes, obesity, osteoporosis and Alzheimer's disease," Expert Opinion Investi. Drugs, 2010, 19(9):1039-1048.
Ishii et al., "Sphingosine-1-phosphate mobilizes osteoclast precursors and regulates bone homeostasis," Nature, Mar. 2009, 458(7237):524-528.
Ismail et al., "Number and Type of Vertebral Deformities: Epidemiological Characteristics and Relation to Back Pain and Height Loss," Osteoporosis International, 1999, 9:206-213.
Jia et al., "Design, Synthesis and Biological Activity of Novel Non-Amidine Factor Xa Inhibitors, Part 1: P1 Structure-Activity Relationships of the Substituted 1-(2-Naphtyl)-1H-pyrazole-5-carboxylamides," Bioorganic & Medicinal Chemistry Letters, 2002,12:1651-1655.
Jogie et al., "Unusual protein-binding specificity and capacity of aza-arenophilic gels," Journal of Molecular Recognition, 1998, 11:261-262.
Jones and Leonard, "The Emergence of GPR119 Agonists as Anti-Diabetic Agents," Ann. Rep. Med. Chem., 2009, 44:149-170.
Jones et al. "GPR119 agonists for the treatment of type 2 diabetes," Expert Opin. Ther. Patents, 2009, 19(10): 1339-1359.
Jones, "The Discovery of APD334, A Selective S1P1 Functional Antagonist", EFMC-ISMC (2014), Sep. 8, 2014 (PowerPoint), 22 pages.
Jones, Robert M., "Discovery of Potent and Selective Sphingosine-1-Phosphate 1 (S1P1) Receptor Agonists", CHI 6th Annual Drug Discovery Chemistry, San Diego, CA, Apr. 12, 2011, 22 pages.
Jones, Robert M., "Discovery of Potent and Selective Sphingosine-1-Phosphate 1(S1P1) Receptor Agonists", CHI 6th Annual Discovery on Target, Boston, MA, Nov. 3, 2011, 26 pages.
Joshi et al., "Endogenous PYY and GLP-1 mediate L-glutamine responses in intestinal mucosa," British Journal of Pharmacology, 2013, 170:1092-1101.
Judge and Bever, "Potassium channel blockers in multiple sclerosis: neuronal Kv channels and effects of symptomatic treatment," Pharmacology & Therapeutics, 2006, 111:224-259.
Jung et al., "Functional Consequences of S1P Receptor Modulation in Rat Oligodendroglial Lineage Cells," Glia, 2007, 55:1656-1667.
Kametani et al. "Benzyene Reaction. IX. Benzyene Reaction of o-halobenzenes with acetonitrile or phenylacetonitrile in organic solvents," J. Org. Chem., 1972, 36(2):327-330.
Kaneider et al., "The immune modulator FTY720 targets sphingosine-kinase-dependent migration of human monocytes in response to amyloid beta-protein and its precursor," FASEB J, 2004, 18:309-311.
Kanstrup et al., "Quality of Lipid-Lowering Therapy in Patients with Ischaemic Heart disease; A Register-Based Study in 3477 Patients," Journal of Internal Medicine, 2004, 255(3):367-372.
Kappos et al., "A placebo-controlled trial of oral fingolimod in relapsing multiple sclerosis," N Engl J Med., 2010. 362(5):387-401.
Kappos et al., "Oral Fingolimod (FTY720) for Relapsing Multiple Sclerosis," N Engl J Med., 2006, 355:1124-1140.

Karimian et al., "Sphingosine kinase-1 inhibition protects primary rat hepatocytes against bile salt-induced apoptosis," Biochim Biophys Acta., 2013, 1832(12):1922-9.
Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol., Dec. 2005, 2(6):439-448.
Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.
Kawakita et al., CAPLUS Abstract 115:136096, 1991, 3 pages.
Kawasaki, Andrew et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists", Arena Pharmaceuticals, Inc., MEDI254, ACS, Mar. 2011, 1 page.
Kawase et al., "a-trifluoromethylated acyloins induce apoptosis in human oral tumor cell lines," Bioorg & Med Chem Ltrs, 1999, 9(21):3113-3118.
Keane et al., "The CHORUS (Cerivastatin in Heart Outcomes in Renal Disease: Understanding Survival) Protocol: A Double-Blind, Placebo-Controlled Trial in Patients with ESRD," American Journal of Kidney Diseases, 2001, 37(1, Suppl. 2):S48-S53.
Keighley and Stockbrugger, "Inflammatory bowel disease," Ailment Pharmacol Ther, 2003, 18:66-70.
Keire et al., "Primary structures of PYY, [Pro34] PYY, and PYY-(3-36) confer different conformations and receptor selectivity," Am. J. Physiol. Gastrointest. Liver Physiol., 2000, 279:G126-G131.
Kelley et al., "Benzodiazepine receptor binding activity of 8-substituted-9-(3-substituted-benzyl)-6 diamethylamino)-9H-purines," Med Chem , 1990, 33(1):196-202.
Kelly et al., "A Synthesis of Aaptamine," Tetrahedron,1985, 41(15):3033-3066.
Kempson et al., "Fused pyrimidine based inhibitors of phosphodiesterase 7 (PDE7): synthesis and initial structure-activity relationships," Bioorganic & Medicinal Chemistry Letters, 2005, 15:1829-1833.
Keul et al., "The Sphinogosine-1-Phosphate Analogue FTY720 Reduces Atherosclerosis in Apolipoprotein E-Deficient Mice," Arterioscler Thromb Vasc Biol., 2007, 27:607-613.
Khattab et al., "Quinolines with heteroatom substituents in position 2 and 4. Nucleophilic substitution of 2,4-dichloro-3-phenylquinolines," ACH—Models in Chemistry, 1994, 131(3-4):521-527.
Kim and Egan, "The Role of Incretins in Glucose Homeostasis and Diabetes Treatment," Pharmacological Reviews, 2008, 60(4):470-512.
Kim et al., "Sphingosine-1-phosphate inhibits human keratinocyte proliferation via Akt/protein kinase B inactivation," Cell Signal, 2004, 16:89-95.
Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.
Kitabayashi et al., "FTY720 Prevents Development of Experimental Autoimmune Myocarditis Through Reduction of Circulating Lymphocytes," J Cardiovasc. Pharmacol. 2000, 35:410-416.
Klotzer et al., "Chlorierende formylierungsreaktionen an pyrimidinen," Monatshefte fuer Chemie, 1965, 96(5):1567-1572 (English Abstract).
Kohno et al., "A Novel Immunomodulator, FTY720, Prevents Development of Experimental Autoimmune Myasthenia Gravis in C57BL/6 Mice," Biol Pharma Bull., 2005, 28(4):736-739.
Kohno et al., "A Novel Immunomodulator, FTY720, Prevents Spontaneous Dermatitis in NC/Nga Mice," Biol. Pharm. Bull., 2004, 27(9):1392-1396.
Kolosov et al., "The interaction between 4-[phenyl-5-acetyl-6-methyl-3,4-dihydropyrimidine-2-one and 4-brombenzaldehyde", Institute of Organic Chemistry, Kharkiv, retrieved on Mar. 30, 2008, http://conf.iflab.kiev.ua/eng/reports/show/?id=926, 2 pages (Abstract Only).
Komori et al., "Effect of Etrasimod on Circulating Lymphocyte Subsets: Data from a Randomized Phase 1 Study in Healthy Japanese and Caucasian Men", The American Journal of Gastroenterology, Dec. 2020, 115: p. S12.

(56) References Cited

OTHER PUBLICATIONS

Koreck et al., "The role of innate immunity in the pathogenesis of acne," Dermatol., 2003, 206:96-105.
Kotian et al., "Synthesis, ligand binding, and quantitative structure-activity relationship study of 3β-(4'-substituted phenyl)-2β-heterocyclic tropanes: evidence for an electrostatic interaction at the 2β-position," J Med Chem, 1996, 39(14):2753-2763.
Koumbourlis, "Scoliosis and the respiratory system," Paediatric Respiratory Reviews, 2006. 7:152-160.
Kovarick et al., "Multiple-Dose FTY720: Tolerability, Pharmacokinetics, and Lymphocyte Responses in Healthy Subjects," The Journal of Clinical Pharmacology, May 2004, 44(5):532-537.
Krauze et al., "Derivatives of 3-cyano-6-phenyl-4-(3'-pyridyl)-pyridine-2(1H)-thione and their neurotropic activity," European Journal of Medicinal Chemistry, 1999, 34(4):301-310.
Krauze et al., "Synthesis of 3-oxoisothiazolo[5,4-b]pyridines," Khimiya Geterotsiklicheskikh Soedinenii, 1982, (4):508-512.
Kreisberg et al, "Hyperlipidemia (High Blood Fat)," The Journal of Clinical Endocrinology & Metabolism, 2005, 90:0, 2 pages.
Kubota et al, "Disruption of Adiponectin Causes Insulin Resistance and Neointimal Formation," J. Biol. Chem., 2002, 2002, 277:25863-25866.
Kumagai et al., "Synthesis, SAR and biological activities of CRH1 Receptor: Novel 3- or 4-carbamoyl-1,2,5,6-tetrahydropyridinopyr-rolopyrimidine derivative," 4th ACS National Meeting, Aug. 18-22, 2002, Boston, MA, Poster #259, 1 page.
Kurose et al., "Effects of FTY720, a novel immunosuppressant, on experimental autoimmune uveoretinitis in rats," Exp. Eye Res., 2000, 70:7-15.
Lai et al, "Association between Obesity and Hyperlipidemia Among Children," Yale Journal of Biology and Medicine 74 (2001), pp. 205-210.
Lai et al., "A one-pot method for the efficient conversion of aryl-and acyl-substituted methyl alcohols into chlorides," Synthetic Communications, 2003, 33(10):1727-1732.
Lala et al., "Role of nitric oxide in tumor progression: Lessons from experimental tumors," Cancer Metastasis Rev., 1998, 17:91-106.
Lamontagne et al., "Antagonism of Sphingosine-1-Phosphate Receptors by FTY720 Inhibits Angiogenesis and Tumor Vascularization," Cancer Res., 2006, 66:221-231.
Lan, "GPR119 is Required for Physiological Regulation of Gucagon-like Peptide-1 Secretion but not for Metabolic Homeostasis," J. Endocrinol., 2009, 201:219-230.
Lanier et al., "Small molecule corticotrophin-releasing factor antagonists," Expert Opinion, 2002, 12(11):1619-1630.
Le Bas, et al, "Radioiodinated Analogs of EP 00652218 for the Exploration of the Tachykinin NK1 Receptor by Spect," J. Labelled Compl. Radiopharm. 2001, 44, S280-S282.
Le Stunff and Bougneres, "Early Changes in Postprandial Insulin Secretion, Not in Insulin Sensitivity, Characterize Juvenile Obesity," Diabetes, 1994, 43:696-702.
Leadbeater et al., "First Examples of Transition-Metal Free Sonogashira-Type Couplings," Organic Letters, 2003, 5(21):3919-3922.
Lechleitner, "Dyslipidemia and Renal Disease—Pathophysiology and Lipid Lowering Therapy in Patients with Impaired Renal Function," Journal of Clinical and Basic Cardiology, 2000, 3(1):3-6.
Lee et al, "Neuropeptide Y induces ischemia angiogenesis and restores function of ischemic skeletal muscles," J. Clin. Invest., 2003, 111;1853-1862.
Lee et al., "FTY720: A Promising Agent for Treatment of Metastatic Hepatocellular Carcinoma," Clin. Cancer Res., 2005, 11:8458-8466.
Lee et al., "Impaired angiogenesis in neuropeptide Y (NPY)-Y2 receptor knockout mice," Peptides, 2003, 24:99-106.
Lee et al., "Synthesis and biological evaluation of clitocine analogues as adenosine kinase inhibitors," Bioorg & Med Chem Ltrs, 2001, 11(18):2419-2422.
Leese et al., "Potential antipurines. Part II. Synthesis of 6- and 9-substituted purines and 8-azapurines," Journal of the Chemical Society, 1958, 4107-4110.

LeWitt, "Levodopa for the Treatment of Parkinson's Disease," The New England Journal of Medicine, Dec. 2008, 359(23):2468-2476.
Lima et al., "FTY720 Treatment Prolongs Skin Graft Survival in a Completely Incompatible Strain Combination," Transplant Proc., 2004, 36:1015-1017.
Lin, et al., "Synthesis and Antitumor Activity of Halogen-Substituted 4-(3,3-Dimethyl-1-triazeno)uinolones," J. Med. Chem., 1978, 21(3):268-272.
Lindvall and Kokaia, "Stem cells for the treatment of neurological disorders," Nature, 2006, 44:1094-1096.
Litvak et al., "Polynucleotides and Their Components in the Processes of Aromatic Nucleophilic Substitution: II.1 Nucleophilic Modification of 3',5'-Bis-O-(a,β,α',β'-tetrafluoropyrid-y-yl)thymidine," Russian Journal of Bioorganic Chemistry, 2004, 30(4):337-343.
Litvinov et al., "Naphythyridines. Structure, physicochemical properties and general methods of synthesis," Russian Chemical Reviews, 2000, 69(3):201-220.
Liu et al, "Human Pancreatic Cancer Growth is inhibited by Peptide YY and BIM-43004-1," J. Surg. Res., 1995, 58:707-712.
Liu et al, "Pancreatic Peptide YY mRNA Levels Increase during Adaptation after Small Intestinal Resection," J. Surg. Res., 1995, 58:6-11.
Liu et al, "Peptide YY: A Potential Proabsorptive Hormone for the Treatment of Malabsorptive Disorders," Am Surg., 1996, 62:232-236.
Liu et al, "Y2 receptors decrease human pancreatic cancer growth and intracellular cyclic adenosine monophosphate levels," Surgery, 1995, 118:229-236.
Liu et al., "Long-Term Effect of FTY720 on Lymphocyte Count and Islet Allograft Survival in Mice," Microsurgery, 2007, 27:300-304.
Lleo et al., "Etiopathogenesis of primary viliary cirrhosis," World J Gastroenterol, Jun. 2008, 14(21):3328-3337.
Loftus, "Clinical epidemiology of inflammatory bowel disease: Incidence, prevalence, and environmental influences," Gastroenterology, 2004; 126(6):1504-17.
Loupy et al., "Easy and efficient SNAr Reactions on halopyridines in solvent free conditions," Heterocycles, 1991, 32(10):1947-1952.
Lumb et al, "Novel Selective Neuropeptide Y2 Receptor PEGylated Peptide Agonists Reduce Food Intake and Body Weight in Mice," J. Med. Chem., 2007, 50:2264-2268.
Lundberg et al., "Localization of peptide YY (PYY) in gastrointestinal endocrine cells and effects on intestinal blood flow and motility," PNAS USA, 1982, 79:4471-4475.
Luo et al., "Clinical manifestations and therapy of extraintestinal manifestations with inflammatory bowel disease," International Journal of Digestive Diseases, 2006, pp. 87-90 (with English abstract).
Luo et al., "Microwave-assisted synthesis of aminopyrimidines," Tetrahedron Letters, 2002, 43:5739-5742.
Ma et al., "Mild Method for Ullmann Coupling Reaction of Amines and Aryl Halides," Organic Letters, 2003, 5(14):2453-2455.
Macchia et al., "New N-n-propyl-substituted 3-aryl- and 3-cyclohexylpiperidines as partial agonists at the D4 dopamine receptor," J Med Chem, 2003, 46(1):161-168.
Mackman et al., "2-(2-Hydroxy-3-alkoxyphenyl)-IH-benzimidazole-5-carboxamidine derivatives as potent and selective urokinase-type plasminogen activator inhibitors," Bioorganic & Medicinal Chemistry Letters, 2002, 12(15):2019-2022.
Madhusudan et al., "Tyrosine kinase inhibitors in cancer therapy," Clinical Biochem., 2004, 37:618-635.
Maeda et al., "Diet-induced insulin resistance in mice lacking adiponectin/ACRP30," Nat. Med., 2002, 8:731-737.
Majeed et al, "Stannylation Reactions and Cross-Couplings in Pyrimidines," Tetrahedron, 1989, 45(4):993-1006.
Maki et al., "Prevention and Cure of Autoimmune Diabetes in Nonobese Diabetic Mice by Continuous Administration of FTY720," Transplantation, 2005, 79:1051-1055.
Maki et al., "Prevention of autoimmune diabetes by FTY720 in Nonobese diabetic mice," Transplantation, Dec. 2002, 74(12):1684-1686.

(56) References Cited

OTHER PUBLICATIONS

Markwalder, et al., "Synthesis and biological evaluation of 1-aryl-4,5-dihydro-1H-pyrazolo[3,4-d]pyrimidin-4-one inhibitors of cyclin-dependent kinases", J. Med. Chem., (2004), 47:5894-5911.
Marso et al., "Low Adiponectin Levels are Associated with Atherogenic Dyslipidemia and Lipid-Rich Plaque in Nondiabetic Coronary Arteries," Diabetes Care, 2008, 31:989-994.
Martin et al., "A Double-Blind, Randomized, Incomplete Crossover Trial to Assess the Dose Proportionality of Rosuvastatin in Healthy Volunteers," Clinical Therapeutics, 2003, 25(8):2215-2224.
Martin et al., "Absolute Oral Bioavailability of Rosuvastatin in Healthy White Adult Male Volunteers," Clinical Therapeutics, 2003, 25(10):2553-2563.
Martin et al., "An Open-Label, Randomized, Three-Way Crossover Trial of the Effects of Coadministration of Rosuvastatin and Fenofibrate on the Pharmacokinetic Properties of Rosuvastatin and Fenofibric Acid in Healthy Male Volunteers," Clinical Therapeutics, 2003, 25(2): 459-471.
Martin et al., "Metabolism, Excretion, and Pharmacokinetics of Rosuvastatin in Healthy Adult Male Volunteers," Clinical Therapeutics, 2003, 25(11):2822-2835.
Martini et al., "Current perspectives on FTY720," Expert Opin. Investig. Drugs, 2007, 16:505-518.
Martini et al., "S1P modulator FTY720 limits matrix expansion in acute anti-thy1 mesangioproliferative glomerulonephritis," Am J Physiol Renal Physiol., 2007, 292:F1761-F1770.
Marzano et. al., "Cutaneous manifestations in patients with inflammatory bowel diseases: pathophysiology, clinical features, and therapy," Inflamm. Bowel Dis., 2014, 20:213-227.
Marzano et. al., "Role of inflammatory cells, cytokines and matrix metalloproteinases in neutrophil-mediated skin diseases," Experimental Immunology, 2010, 162:1-11.
Matloubian et al., "Lymphocyte egress from thymus and peripheral lymphoid organs in dependent on S1P receptor 1," Nature, Jan. 2004, 427:355-360.
Matsuda et al., "Role of Adiponectin in Preventing Vascular Stenosis: The Missing Link of Adipo-Vascular Axis," J Biol Chem, 2002, 277:37487-37491.
Matsui et al., "Highly Potent Inhibitors of TNF-A Production. Part II: Metabolic Stabilization of a Newly Found Chemical Lead and Conformational Analysis of an Active Diastereoisomer," Bioorganic & Medicinal Chemistry, 2002, 10(12):3787-3805.
Matsuno et al., "Potent and Selective Inhibitors of Platelet-Derived Growth Factor Receptor Phosphorylation. 3. Replacement of Quinazoline Moiety and Improvement of Metabolic Polymorphism of 4-[4-N-Substituted (thio) caramoyl]-1-piperazinyl]-6,7-diamethoxyquinazoline Derivatives," J Med Chem, 2003, 46(23):4910-4925.
Matsuura et al., "Effect of FTY720, a novel immunosuppressant, on adjuvant- and collagen-induced arthritis in rats," Int. J Immunopharmacol. 2000, 22:323-331.
Matsuura et al., "Effect of FTY720, a novel immunosuppressant, on adjuvant-induced arthritis in rats," Inflamm. Res. 2000, 49:404-410.
MayoClinic.com [online], "Type 2 diabetes," Jan. 2021, retrieved on Mar. 24, 2022, retrieved from URL <https://www.mayoclinic.org/diseases-conditions/type-2-diabetes/symptoms-causes/syc-20351193>, 8 pages.
MayoClinic.com [online], "Obesity," Sep. 2021, retrieved on Mar. 24, 2022, retrieved from URL <https://www.mayoclinic.org/diseases-conditions/obesity/symptoms-causes/syc-20375742>.
MayoClinic.com [online], "Metabolic syndrome," May 2021, retrieved on Mar. 24, 2022, retrieved from URL <https://www.mayoclinic.org/diseases-conditions/metabolic-syndrome/symptoms-causes/syc-20351916>, 4 pages.
McFadden et al., "Peptide YY inhibits the growth of Barrett's esophageal adenocarcinoma in vitro," Am. J. Surg., 2004, 188:516-519.
McIntosh et al., "Dipeptidyl peptidase IV inhibitors: How do they work as new antidiabetic agents," Regulatory Peptides, 2005, 128:159-165.

Medscape [online], "Inflammatory Bowel Disease: Practice Essentials," Accessed Jan. 8, 2015, Last Updated Apr. 10, 2020, retrieved from URL <https://emedicine.medscape.com/article/179037-overview>, 2 pages.
Mentlein, "Therapeutic assessment of glucagon-like peptide-1 agonists compared with dipeptidyl peptidase IV inhibitors as potential antidiabetic drugs," Expert Opin Investig Drugs, 2005, 14(1):57-64.
Mesguiche et al., "4-Alkoxy-2,6-diaminopyrimidine Derivatives: Inhibitors of Cyclin Dependent Kinases 1 and 2," Bioorganic & Medicinal Chemistry Letters, 2003, 13(2):217-222.
Metzger et al., "Einstufensynthese von 2,4-Bis(sec-alkylamino-6-halogen-3-pyridincarbonitrilen**," Liebigs Annalen der Chemie, 1980, 6:946-953 (with English abstract).
Miron et al., "FTY720 Modulates Human Oligodendrocyte Progenitor Process Extension and Survival," Ann Neurol, 2008, 63:61-71.
Mitchell and Borasio, "Amyotrophic lateral sclerosis," The Lancet, Jun. 2007, 369: 2031-2041.
Mitsunobu, "The Use of Diethyl Azodicarboxylate and Triphenylphosphine in Synthesis and Transformation of Natural Products", Synthesis, 1981, 1-28.
Mittelbach and Junek., "Syntheses with Nitriles. 60. (1). Preparation of 4-Amino-5-cyano-6-phenylpyrimidines from 2-Amino-1,1-dicyano-2-phenylethene," J. Heterocyclic Chem, 1980, 17(7):1385-1387.
Miyamoto et al., "Therapeutic Effects of FTY720, a New Immunosuppressive Agent, in a Murine Model of Acute Viral Myocarditis," J Am Coll Cardiol., 2001, 37(6):1713-1718.
Miyashita et al., "Preparation of Heteroarenecarbonitriles by Reaction of Haloheteroarenes with Potassium Cyanide Catalyzed by Sodium p-Toluenesulfinate," Heterocycles, 1994, 39(1):345-350.
Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.
Mohan et al., "Solid-Phase Synthesis of N-Substituted Amidinophenoxy Pyridines as Factor XA Inhibitors," Bioorganic & Medicinal Chemistry Letters, 1998, 8(14):1877-1882.
Mombereau et al., "Genetic and Pharmacological Evidence of a Role for $GABA_B$ Receptors in the Modulation of Anxiety- and Antidepressant-Like Behavior," Neuropsychopharmacology, 2004, 29(6):1050-1062.
Mongin and Queguiner, "Advances in the directed metallation of azines and diazines (pyridines, pyrimidines, pyrazines, pyridazines, quinolines, benzodiazines and carbolines). Part 1: Metallation of pyridines, quinolines and carbolines," Tetrahedron, 2001, 57(19):4059-4090.
Montgomery et al., "Isonucleosides. I. Preparation of Methyl 2-Deoxy-2-(purin-9-yl)arabinofuranosides and Methyl 3-Deoxy-3-(purin-9-yl) xylofuranosides," Journal of Organic Chemistry, 1975, 40(13):1923-1927.
Morimoto et al., "Potent and selective ET-A Antagonists. 1. Syntheses and Structure-Activity Relationships of N-(6-(2-(Aryloxy)ethoxy)-4-pyrimidinyl)sulfonamide Derivatives," J Med Chem, 2001, 44 (21):3355-3368.
Morissette, et al., "High-Throughput Crystallization: Polymorphs, Salts, Co-Crystals and Solvates", Adv. Drug Delivery Rev., 56:275-300 (2004).
Moshchitskii et al., "Reaction of 2, 3, 5, 6-tetrachloro-4-pyridyl vinyl sulfone with nucleophilic agents," Khimiya Geterotsiklicheskikh Soedinenii, 1972, 1634-1637, (Translated pp. 1482-1485).
Mosti et al., "4-Substituted 1-Phenyl-1H-Indazoles With Analgesic, Antiinflammatory, Antipyretic and Local Anesthetic Activities," IL Farmaco, 1990, 45(4):415-429.
Mosti et al., "Synthesis and Preliminary biological Evaluation of Novel N-Substited 1-Amino-3-[1-methyl(phenyl)-1H-indazol-4-yloxy]-propan-2-ols Interesting as Potential Antiarrhythmic, Local Anaesthetic and Anagesic Agents," Arzneim-Forsch Drug Res, 2000, 50(11):963-972.
Muci and Buchwald, "Practical Palladium Catalysts for C—N and C—O Bond Formation," Topics in Current Chemistry, 2002, 219:131-209.
Muck et al., "Lack of Pharmacokinetic Drug-Drug Interaction between Orlistat and Cerivastatin," Clinical Drug Investigation, 2000, 19(1):71-73.

(56) References Cited

OTHER PUBLICATIONS

Muller et al., "7-Deaza-2-phenyladenines: Structure-Activity Relationships of Potent A₁ Selective Adenosine Receptor Antagonists," J Med Chem, 1990, 33:2822-2828.

Nakamura et al., "Effect of Cerivastatin on Endothelial Dysfunction and Aortic CD36 Expression in Diabetic Hyperlipidemic Rats," Hypertens Res, 2004, 27(8):589-598.

Nakashima et al., "Impaired Initiation of Contact Hypersensitivity by FTY720," J Invest Dermatol., 2008. 128:2833-2841.

Nakazato et al., "Design, synthesis and structure-affinity relationships of 4-methylidenepiperidine and 4-aryl-1,2,3,6-tetrahydropyridine derivatives as corticotropin-releasing factor1 receptor antagonists," Bioorganic & Medicinal Chemistry, 2000, 8(5):1183-1193.

Nakazato et al., "Synthesis, SAR and biological activities of CRH1 receptor: Novel 3- or 4-carbamoyl-1,2,5,6-tetrahydropyridinoquinoline derivative," 24th ACS National Meeting, Aug. 18-22, 2002, Boston, MA. Poster #258, 1 page.

National Diabetes Information Clearinghouse [online] "Insulin resistance and Pre-Diabetes," last updated May 2018, retrieved on Mar. 23, 2022, retrieved from URL <https://www.niddk.nih.gov/health-information/diabetes/overview/what-is-diabetes/prediabetes-insulin-resistance>, 6 pages.

National Library of Medicine [online], "Glucose Metabolism Disorders", 2011, retrieved Jan. 11, 2011, retrieved from URL <http://nlm.nih.gov/cgi/mesh/2011MB_cgi?mode=&term=Glucose+Metabolism+Disorders&field=entry>, 3 pages.

Nauck et al., "Gastric Inhibitory Polypeptide and Glucagon-Like Peptide-1 in the Pathogenesis of Type 2 Diabetes," Diabetes, 2004, 53(3):S190-196.

Nauck et al., "Incretins and Their Analogues as New Antidiabetic Drugs," Drug News Perspect, 2003, 16(7):413-422.

ndep.nih.gov [online], "Diabetes Prevention," May 26, 2009, retrieved Jul. 1, 2011, retrieved from URL <http://ndep.nih.gov/diabetes/prev/prevention.htm>, 7 pages.

Nesi et al., "New Difunctionalized 4-Nitroisoxazoles from α-Nitroacetophenone Oxime," Heterocycles, 1985, 23(6):1465-1469.

Nestle et al., "Plasmacytoid predendritic cells initiate psoriasis through interferon-alpha production," J Exp Med., 2005, 202(1):135-43.

Neurath et al., "Antibodies to Interleukin 12 Abrogate Established Experimental Colitis in Mice," J. Exp. Med. 182:1281-1290, 1995.

Newman et al., "Solid-state analysis of active pharmaceutical ingredient in drug products," DDT, Oct. 2003, 8(19):898-905.

Nezasa et al., "Uptake of rosuvastatin by isolated rat hepatocytes: comparison with pravastatin," Xenobiotica, 2003, 33(4):379-388.

Nicewonger et al., "Microwave-assisted acylation of 7-amino-5-aryl-6-cyanopyrido[2,3-d] pyrimidines," Molecular Diversity, 2003, 7(2-4):247-252.

Niementowski, J. Praktika Chem., [2] "Synthesen von Chinazolinverbindugen" (1895), 51, 564-572.

Nightingale et al., "Gastrointestinal hormones in short bowel syndrome. Peptide YY may be the 'colonic brake' to gastric emptying," Gut, 1996, 39:267-272.

Nishimura et al., "Adiponectin Prevents Cerebral Ischemic Injury Through Endothelial Nitric Oxide Synthase-Dependent Mechanisms," Circulation, 2008, 117:216-223.

Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.

Norman et al., "Structure-Activity Relationships of a Series of Pyrrolo[3,2-d] pyrimidine Derivatives and Related Compounds as Neuropeptide Y5 Receptor Antagonists," J Med Chem, 2000, 43(22):4288-4312.

Novinson et al., "Novel Heterocyclic Nitrofurfural Hydrazones. In vivo Antitrypanosomal Activity," J Med Chem, 1976, 19(4):512-516.

O'Brien et al., "Vascular cognitive impairment," The Lancet Neurology, Feb. 2003, 2:89-98.

Ogawa et al., "A novel sphingosine-1-phosphate receptor agonist KRP-203 attenuates rate autoimmune myocarditis," Biochem. Biophys. Res. Commun., 2007, 361:621-628.

Okada et al., "Peripherally Not Centrally Administered Peptide YY(PYY) Decreases High Fat Diet Intake," Endocrine Society, 1993, 520 B:180.

Okayasu et al, "A Novel Method in the Induction of Reliable Experimental Acute and Chronic Ulcerative Colitis in Mice," Gastroenterology, 98:694-702, 1990.

Okazaki et al., "Effects of FTY720 in MRL-Ipr/Ipr mice: therapeutic potential in systemic lupus erythematosus," J Rheumatol., 2002, 29:707-716.

Oku et al., "Adiponectin deficiency suppresses ABCA1 expression and ApoA-I synthesis in the liver," FEBS Letters, 2007, 581:5029-5033.

Olesen, "The use of bioisosteric groups in lead optimization," Current Opinion in Drug Discovery & Development, 2001, 4(4):471-478.

Olsson et al., "Rosuvastatin: A Highly Effective New HMG-CoA Reductase Inhibitor," Cardiovascular Drug Reviews, 2002, 20(4):303-328.

Olsson, "Statins: how far have we come? A review of rosuvastatin," International Journal of Clinical Practice, 2003, Supplement 137:15-25.

Oo et al., "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.

Ortiz et al., "A Novel Long-Acting Selective Neuropeptide Y2 Receptor Polyethylene Glycol-Conjugated Peptide Agonist Reduces Food Intake and Body Weight and Improves Glucose Metabolism in Rodents," JPET, 2007, 323:692-700.

Ouchi and Walsh, "Adiponectin as an anti-inflammatory factor," Clinica Chimica Acta, 2007, 380:24-30.

Ouchi et al., "Novel Modulator for Endothelial Adhesion Molecules: Adipocyte-Derived Plasma Protein Adiponectin," Circulation, 1999, 100:2473-2476.

Overton et al., "GPR119 a Novel G Protein-coupled Receptor Target for the Treatment of Type 2 Diabetes and Obesity," Brit. J. Pharmacol., 2008, 153:576-581.

Overton et al., "Deorphanization of a G protein-coupled receptor for oleoylethanolamide and its use in the discovery of small-molecule hypophagic agents," Cell Metabolism, 2006, 3:167-175.

Oxford Online Dictionary, Definition of Prescription, 2017, 4pp.

Ozeki el al., "Studies on Antiallergy Agent. 1. Synthesis of 1,4-Dihydro-4-oxo-3--quinolinecarboxylic Acids" Yakugaku Zasshi, 1987, 107(2):123-134.

Pan et al., "A Monoselective Sphingosine-1-Phosphate Receptor-1 Agonist Prevents Allograft Rejection in a Stringent Rat Heart Transplantation Model," Chem. Biol., 2006, 13:1227-1234.

Parker and Balasubramaniam, "Neuropeptide Y Y2 receptor in health and disease," British Journal of Pharmacology, 2008, 153:420-431.

Parlow et al., "Design, Synthesis, and Crystal Structure of Selective 2-Pyridone Tissue Factor VIIa Inhibitors," J Med Chem, 2003, 46(22):4696-4701.

Paul et al., "Evidence-based recommendations on topical treatment and phototherapy of psoriasis: systematic review and expert opinion of a panel of dermatologists," J Eur Acad Dermatol Venereol, 2012, 26 (suppl 3): 1-10.

Paulsen et al., "Darstellung von Bausteinen zur Synthese carbocyclischer furanose-analoga," Chemische Berichte, 1981, 114(1):346-358 (with English abstract).

Pearson, "Inflammatory bowel disease," Nursing Times, 2004, 100(9):86-90.

Peat et al., "Novel pyrazolopyrimidine derivatives as GSK-3 inhibitors", Bioorganic & Medicinal Chemistry Letters, 2004, 14:2121-2125.

Pederson, "The Impact of Obesity on the Pathogenesis of Non-Insulin-Dependent Diabetes Mellitus: A Review of Current Hypotheses," Diabetes/Metabolism Reviews., 1989, 5(6):495-509.

(56) References Cited

OTHER PUBLICATIONS

Pei et al., "Discovery and Structure-Activity Relationships of Piperidinone- and Piperidine-Constrained Phenethylamines as Novel, Potent, and Selective Dipeptidyl Peptidase IV Inhibitors," J Med Chem, 2007, 50:1983-1987.

Pelat et al., "Rosuvastatin Decreases Caveolin-1 and Improves Nitric Oxide-Dependent Heart Rate and Blood Pressure Variability in Apolipoprotein E-/- Mice in Vivo," Circulation, 2003, 107(19): 2480-2486.

Perry et al., "Prospective study of risk factors for development of non-insulin dependent diabetes in middle aged British men," BMJ, 1995, 310:560-564.

Peters et al., "Aminomethylpyrimidines as novel DPP-IV inhibitors: A 105-fold activity increase by optimization of aromatic substituents," Bioorganic & Medicinal Chemistry Letters, 2004, 14:1491-1493.

Peterson et al., "Expanding the Scope of Crystal Form Evaluation in Pharmaceutical Science," J Pharm Pharmaceut Sci, 2006, 9(3):317-326.

Pfeilschifter et al., "Treatment with the immunomodulator FTY720 does not promote spontaneous bacterial infections after experimental stroke in mice," Experimental Translational Stroke Med., 2011, 36 pages.

Phillips et al., "Discovery of N-[2-[5-[Amino(imino)methyl]-2-hydroxyphenoxyl]-3,5-difluoro-6-[3-(4,5-dihydro-1-methyl-1H-imidazol-2-yl)phenoxy]pyridin-4-yl)-N-methylglycine(ZK-807834): A Potent, Selective, and Orally Active Inhibitor of the Blood Coagulation Enzyme Factor Xa1-," J Med Chem. 1998, 41(19):3557-3562.

Pittner et al., "Effects of PYY[3-36] in rodent models of diabetes and obesity," International Journal of Obesity,2004, 28:963-971.

Pomorski, "Synthesis of Acids, Derivatives of 4-Hydroxy-1,5-Naphtbyridine," Roczniki Chemii Ann Soc Chim Polonorum, 1974, 48:321-325.

Potenza and Lerner, "A Rapid Quantitative Bioassay for Evaluating the Effects of Ligands Upon Receptors That Modulate cAMP Levels in a Melanophore Cell Line," Pigment Cell Research, 1992, 5(6):372-378.

Poupaert, "Drug Design: Basic Principles and Applications," Encyclopedia of Pharmaceutical Technology, 2007, 1362-1369 (James Swarbrick 3rd ed.).

Prasad et al., "Convenient Methods for the Reduction of Amides, Nitriles, Carboxylic Esters, Acids and Hydroboration of Alkenes Using NaBH4/12 System," Tetrahedron, 1992, 48(22):4623-4628.

Premenko-Lanier et al., "Transient FTY720 treatment promotes immune-mediated clearance of a chronic viral infection," Nature, Aug. 2008, 454:894-899.

Press et al., "Synthesis and SAR of 6-Substituted Purine Derivatives as Novel Selective Positive Inotropes," J Med Chem, 1992, 35(24):4509-4515.

prnewswire.com [online], "Arena Pharmaceuticals Reports Positive Long-Term Data from the Open-Label Extension of the Phase 2 OASIS Trial Evaluating Etrasimod for Treatment of Ulcerative Colitis," Jan. 2019, retrieved on Mar. 25, 2022, retrieved from URL <https://www.prnewswire.com/news-releases/arena-pharmaceuticals-reports-positive-long-term-data-from-the-open-label-extension-of-the-phase-2-oasis-trial-evaluating-etrasimod-for-treatment-of-ulcerative-colitis-300773493.html>, 2 pages.

Quaglino et. al., "Phenotypical characterization of circulating cell subsets in pyoderma gangrenosum patients: the experience of the Italian immuno-pathology group," J Eur Acad Dermatol Venereal, 2016, 30(4):655-8.

Quesada et al., "2-Amino-5-nitro-4,6-dipiperidionpyrimidinium hydrogensulfate monohydrate: hydrogen-bonded sheets containing highly distorted cations," Acta Cryst, 2003, 59:102-104 (Abstract; 1 page).

Quintela et al., "6-Dimethylamino 1H-Pyrazolo[3,4-d]pyrimidine Derivatives as New Inhibitors of Inflammatory Mediators in Intact Cells," Bioorganic &Medicinal Chemistry (2003) 11:863-868.

Quintela et al., "Pyrazolopyrimidines: synthesis, effect on histamine release from rat peritoneal mast cells and cytotoxic activity," Eur J Med Chem (2001) 36:321-332.

Raffel et al., "Diabetes Mellitus," Principles And Practice Of Medical Genetics, 1996, 1:1401-1440.

Raisz, "Pathogenesis of osteoporosis: concepts, conflicts, and prospects," J Clin Invest, 2005, 115(12):3318-3325.

Ram et al., "Chemotherapeutic agents: Part XXII—Synthesis of p-deficient pyrimidines as leishmanicides," Indian Journal of Chemistry, 1991, 30B(10):962-965.

Rao et al., "Impaired Glucose Tolerance and Impaired Fasting Glucose," 1962, American Family Physician, 69(8):1961-1968.

Rasenack et al., "Crystal habit and tableting behavior," International Journal of Pharmaceutics, Sep. 2002, 244(1-2): 45-57.

Rausch et al., "Predictability of FTY720 efficacy in experimental autoimmune encephalomyelitis by in vivo macrophage tracking: Clinical implications for ultrasmall superparamagnetic iron oxide-enhanced magnetic resonance imaging," J Magn. Reson. Imaging, 2004, 20:16-24.

Raveney et al., "Fingolimod (FTY720) as an Acute Rescue Therapy for Intraocular Inflammatory Disease," Arch Ophthalmol, 2008, 126(10):1390-1395.

Rayasam et al., "Fatty acid receptors as new therapeutic targets for diabetes," Expert Opin Thera Targets, 2007, 11(5):661-671.

Reed and Scribner, "In-vivo and in-vitro models of type 2 diabetes in pharmaceutical drug discovery," Diabetes Obes Metab, 1999 1(2):75-86.

Rehwald and Gewald, "Syntheses of Thieno[2,3-d)Pyrimidines and Aminopyrimidines from 2-Alkoxy-5-Cyano-4-Thioxopyrimidine Intermediates," Heterocycles, 1998, 48(6):1157-1167.

Reines et al., "Topical application of sphingosine-1-phosphate and FTY 720 attenuate allergic contact dermatitis reaction through inhibition of dendritic cell migration," J Clin Invest Dermatol, 2009, 129(8):1954-62.

Reinisch et al., "Adalimumab for induction of clinical remission in moderately to severely active ulcerative colitis: results of a randomised controlled trial," Gut, 2011, 60:780-787.

Remington's Pharmaceutical Sciences, 1985, Mack Publishing Company, 17:1418-1419, 5 pages.

Renshaw and Batterham, "Peptide YY: A Potential Therapy for Obesity," Current Drug Targets, 2005, 6:171-179.

Reshetnyak, "Primary biliary cirrhosis: Clinical and laboratory criteria for its diagnosis," World J of Gastroenterology, 2015, 21(25):7683-7708.

Rewcastle et al., "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," J Med Chem, 1996, 39:1823-1835.

Rheumatoid Arthritis Health Center—Most Common Types of Arthritis, WebMD, http://www.webmd.com/rheumatoid-arthritis/guide/most-common-arthritis-types, 2012, 2 pages.

Rimoin et al., "Emery And Rimoin's Principles And Practice Of Medical Genetics", 1996, 3:1401-1402.

RN 380350-42-5, STN/CAPLUS, 2002, 1 page.

Roberts and Suschitzky, "Peroxy-acid Oxidation of NN-Disubstituted Aminotetrafluoro-, Amino-3-chlorotrifluoro-, and Amino-3,5-dichlorodifluoro-pyridines," Journal of the Chemical Society, 1969 11:1485-1491.

Roberts et at., "Polychloroaromatic compounds. Part I. Oxidation of pentachloropyridine and its NN-disubstituted amino-derivatives with peroxyacids," Journal of the Chemical Society (Section) C: Organic (1968) (12):1537-1541.

Roberts, "Two More Drugs for Dyslipidemia", American Journal of Cardiology, 2004 93:809-811.

Robev, "4-Cyclopropylamino- and 4-Cyclobutylaminoderivatives of some Arylsubstituted 5-Cyanopyrimidines," Doktady Bolgarskoi Akademii Nauk, 1981 34(12):1677-1680.

Robins and Lin, "Potential Purine Antagonists. IV. Synthesis of Some 9-Methyl-6-substituted purines1," Dep of Chem, 1957, 79:490-494.

Rodriguez-Spong et al., "General Principles of Pharmaceutical Solid Polymorphism: A Supramolecular Perspective", Adv Drug Delivery Rev, 2004, 56:241-274.

(56) References Cited

OTHER PUBLICATIONS

Ronald Hoffman, M.D., "Crohns disease and ulcerative colitis," Sep. 1995, http://www.drhoffman.com/page.cfm/171, 5 pages.
Rondinone, "Diabetes: the latest developments in inhibitors, insulin sensitisers, new drug targets and novel approaches" Expert Opin, 2005, 9(2):415-418.
Rosen et al., "Egress: a receptor-regulated step in lymphocyte trafficking," Immunol. Rev. 2003, 195:160-177.
Rosenson, "Rosuvastatin: a new inhibitor of HMG-CoA reductase for the treatment of dyslipidemia", Expert Review of Cardiovascular Therapy, 2003, 1(4):495-505.
Rotwein et al., "Polymorphism in the 5' flanking region of the human insulin gene: a genetic marker for non-insulin-dependent diabetes," N Engl J Med, 1983, 308(2):65-71.
Ruggeri, "Platelets in atherothrombosis," Nat Med, 2002, 8(11):1227-1234.
Ruocco et. al., "Pyoderma gangrenosum: an updated review," Eur. Acad. Dermatol & Venereology, 2009, 23:1008-1017.
Sage, Document regarding search, Feb. 2003, 1 page.
Sakagawa et al., "Rejection following donor or recipient preoperative treatment with FTY720 in rat small bowel transplantation," Transpl. Immunol., 2004, 13:161-168.
Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.
Sandborn et al., "Efficacy and Safety of Etrasimod in a Phase 2 Randomized Trial of Patients with Ulcerative Colitis," Gastroenterology, Feb. 2020, 158(3):550-561.
Sandborn et al., "UEG Week 2018 Oral Presentations OP242—'A Randomized Double-Blind Placebo-Controlled Trial of A Selective, Oral Sphingosine 1-Phosphate Receptor Modulator, Etrasimod (ADP334), In Moderate To Severe Ulverative Colitis: Results From The Oasis Study'" United European Gastroenterology Journal, 2018, 6:A94-A95.
Sanna et al., "Enhancement of capillary leakage and restoration of lymphocyte egress by a chiral S1P1 antagonist in vivo," Nature Chem Biol., Aug. 2006, 2(8):434-441.
Sanna et al., "Sphingosine 1-Phosphate (S1P) Receptor Subtypes S1P1 and S1P3, Respectively, Regulate Lymphocyte Recirculation and Heart Rate," J. Biol Chem., 2004, 279(14):13839-13848.
Sauer et al., "Involvement of Smad Signlaing in Sphingosine 1-Phosphate-mediated Biological Responses of Keratinocytes," J Biol. Chem., 2004, 279:38471-38479.
Sawicka et al., "Inhibition of Th1- and Th2-Mediated Airway Inflammation by the Sphingosine 1-Phosphate Receptor Agonist FTY720," J Immunol., 2003, 171:6206-6214.
Schafer et al., "Zur synthese von 4-aminochinolinen durch intramolekulare Friedel-Cfafts-Reaktion," Montash fur Chemie (1978) 109:527-535 (English Abstract).
Schaper et al., "Sphingosine-1-phosphate differently regulates the cytokine production of IL-12, IL-23 and IL-27 in activated murine bone marrow derived dendritic cells," Mol Immunol., 2014, 59(1):10-8.
Schmid et al., "The Immunosuppressant FTY720 inhibits tumor Angiogenesis via the Sphingosine 1-Phosphate Receptor 1," J Cell Biochem., 2007, 101:259-270.
Schuppel et. al., "Sphingosine 1-phosphate restrains insulin-mediated keratinocyte proliferation via inhibition of Akt through the S1P2 receptor subtype," J Invest Dermatol, 2008, 128:1747-56.
Schuster, "Rosuvastatin—A Highly Effective New 3-hydroxy-3-methylglutaryl Coenzyme A Reductase Inhibitor: Review of clinical Trial Data at 10-40 mg doses in Dyslipidemic Patients" Cardiology, 99(3):126-139 (2003).
Schwab and Cyster, "Finding a way out: lymphocyte egress from lymphoid organs," Nature Immunol., Dec. 2007, 8(12):1295-1301.
Schwartz and Holst, "An Enteroendocrine Full Package Solution," Cell Metabolism, 2010, 11:445-447.
Scott et al., "Rosuvastatin: A Review of Its Use in the Management of Dyslipidemia," American Journal of Cardiovascular Drugs, 4(2), 117-138 (2004).
Semple et al., "Discovery of a second generation of the orphan G-protein coupled receptor GPR119 with an improved profile," Bioorganic & Medicinal Chemistry Letters, 2012, 22:1750-1755.
Shafiee et al., "An efficient enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," Tetrahedron: Asymmetry, Sep. 2005, 16:3094-3098.
Shah et al., "Current Approaches in the treatment of Alzheimer's disease," Biomedicine &Pharmacotherapy, 2008, 62:199-207.
Shah, "GPR119 Agonists for the Potential Treatment of Type 2 Diabetes and Related Metabolic Disorders," Vitamins & Hormones, 2010, 84:415-448.
Shah, "GPR119 agonists: A promising new approach for the treatment of type 2 diabetes and related metabolic disorders," Current Opin Drug Discov Develop., 2009, 12:519-532.
Shepherd et al., "Safety of Rosuvastatin," American Journal of Cardiology, 94(7):882-888 (2004).
Shibata et al., "Adiponectin protects against myocardial ischemia-reperfusion injury through AMPK- and COX-2-dependent mechanisms," Nat Med, 2005, 11:1096-1103.
Shibata et al., "Adiponectin protects against the development of systolic dysfunction following myocardial infarction," J. Mol. Cell Cardiol., 2007, 42:1065-1074.
Shibata et al., "Adiponectin Stimulates Angiogenesis in Response to Tissue Ischemia through Stimulation of AMP-activated Protein Kinase Signaling," J. Biol. Chem., 2004, 279:28670-28674.
Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.
Shore et al., "Adiponectin attenuates allergen-induced airway inflammation and hyperresponsiveness in mice," J. Allergy Clin. Immunol, 2006, 118:389-395.
Showell et al., "Tetrahydropyridyloxadiazoles: semirigid muscarinic ligands," J Med Chem (1991) 34(3):1086-1094.
Shtukenberg et al., "Spherulites," Chemical Reviews, 2012, 112:1805-1838.
Sigma-Aldrich, catalog entry for 2-amino-6-chloro-4-pyrimidinol hydrate (catalog No. 07460); page; retrieval date Mar. 16, 2010.
Sigma-Aldrich, catalog entry for 2-amino-6-hydroxy-2-mercaptopyrimidine monohydrate (catalog No. A57406); 1 page; retrieval date Mar. 16, 2010.
Sigma-Aldrich, catalog entry for 4,5-diamino-6-hydroxy-2-mercaptopyrimidine hemisulfate salt hydrate (392464); 1 page; retrieval date Mar. 16, 2010.
Sigma-Aldrich, catalog entry for 4,6-diamino-2-mercaptopyrimidine hydrate (catalog No. 125830); 1 page; retrieval date Mar. 16, 2010.
Silhar et al., "Facile and Efficient Synthesis of 6-(Hydroxymethyl)purines," Org. Lett. (2004) 6(19):3225-3228.
Silvestri et at, "Novel indolyl aryl sulfones active against HIV-1 carrying NNRTI resistance mutations: synthesis and SAR studies," J Med Chem (2003) 46(12):2482-2493.
Smith et al., "Effects of positive allosteric modulators of the GABAB receptor on cocaine self-administration in rats," Psychopharmacology (2004)173(1-2):105-111.
Smith et. al., "Clinical, molecular, and genetic characteristics of PAPA syndrome: a review," Current Genomics, 2010, Bentham Science Publ., 11:519-527.
Soga et al., "Lysophosphatidylcholine enhances glucose-dependent insulin secretion via an orphan G-protein-coupled receptor," Biochem Biophys Res Commun (2005) 326:744-751.
Spruce, Lyle W., "Document regarding search," 2004, 1 page.
Stahly, "Diversity in Single- and Multiple-Component Crystals. The Search for and Prevalence of Polymorphs and Cocrystals," Crystal Growth & Design (2007), 7(6), 1007-1026.
Starosotnikov et al., "Synthesis of 3-substituted 1-aryl-4,6-dinitro-1H-indazoles based on picrylacetaldehyde and their behavior in nucleophilic substitution reactions," Russian Chemical Bulletin 2003, 52(8), 1782-1709.

(56) References Cited

OTHER PUBLICATIONS

Steensma et al., "A novel method for the synthesis of aryl sulfones," Tetrahedron Ltrs (2001) 42:2281-2283.
Stein, "Management of Dyslipidemia in the High-Risk Patient," American Heart Journal, 144(6):S43-S50 (2002).
Sternfeld et al., "Synthesis and serotonergic activity of 3-[2-(pyrrolidin-1-yl)ethyl]indoles: potent agonists for the h5-HT1D receptor with high selectivity over the h5-HT1B receptor," J. Med Chem, 1999, 28(6):761-769.
Storey, et al., "Automation of Solid Form Screening Procedures in the Pharmaceutical Industry—How to Avoid the Bottlenecks", Crystallography Reviews, 10(1):45-46 (2004).
Strupczewski et al., "Synthesis and neuroleptic activity of 3-(1-substituted-4-piperidinyl)-1,2-benzisoxazoles," J Med Chem (1985) 28(6):761-769.
Sturino et al: "Discovery of a potent and selective prostaglandin D2 receptor antagonist, [(3R)-4-(4-chloro-benzyl)-7-Fluoro-5-(methylsulfonyl)-1,2,3,4-tetrahydrocyclopenta[b]indol-3-yl]-acetic acid (MK-0524)", Journal of Medicinal Chemistry, Feb. 22, 2007, pp. 794-806.
Su et. al., "Histopathologic and immunopathologic study of pyoderma gangrenosum," J Cut. Path, 1986, 13(5):323-330.
Suami et al., "Nucleoside analogs. I. Synthesis of 1,3-dihydroxy-2-(6-substituted-9-purinyl)cyclohexane," Journal of Heterocyclic Chemistry (1969) 6(5):663-665.
Sugimoto et al., "Lithiation of 1H-Pyrazolo[3,4-d]pyrimidine Derivative Using Lithium Alkanetellurolate," Tetrahedron Letters (1999) 40:2139-2140.
Sugimoto et al., "Preparation of Nitrogen-Containing π-Deficient Heteroaromatic Grignard Reagents: Oxidative Magnesiation of Nitrogen-Containing n-Deficient Halgenoheteroaromatics Using Active Magnesium," J. Org. Chem. (2003) 68:2054-2057.
Summer et al., "Alveolar macrophage activation and an emphysema-like phenotype in adiponectin-deficient mice," Am J. Physiol. Lung Cell Mol. Physiol, 2008, 294:L1035-L1042.
Suzuki et al., "Efficacy of Mycophenolic Acid Combined with KRP-203, a Novel Immunomodulator, in a Rat Heart Transplantation Model," J Heart Lung Transplant, 2006, 25:302-309.
Suzuki et al., "Immunosuppressive effect of a new drug, FTY720, on lymphocyte responses in vitro and cardiac allograft survival in rats," Transplant Immunol., 1996, 4:252-255.
Takei et al., "A New Synthetic Method for Some Pyrazolo[4,3-]pyrimidines1)," Bulletin of the Chemical Society of Japan, Aug. 23, 2005, 52(1):208-211.
Tao et al., "Adiponectin Cardioprotection After Myocardial Ischemia/Reperfusion Involves the Reduction of Oxidative/Nitrative Stress," Circulation, 2007, 115:1408-1416.
Tatemoto and Mutt, "Isolation of two novel candidate hormones using a chemical method for finding naturally occurring polypeptides," Nature, 1980, 285:417-418.
Tavarela, "Review article: Skin complications associated with inflammatory bowel disease," Aliment Pharmacol Ther, 2004, Suppl 4:50-53.
Taylor et al., "Insights into the mechanism of FTY720 and compatibility with regulatory T cells for the inhibition of graft-versus-host disease (GVHD)," Blood, 2007, 110:3480-3488.
Terashima et al., "Inhibition of human O6-alkylguanine-DNA alkyltransferase and potentiation of the cytotoxicity of chloroethylnitrosourea by 4(6)-(benzyloxy)-2,6(4)-diamino-5-(nitro or nitroso)pyrimidine derivatives and analogues," J Med Chem (1998) 41(4):503-508.
The Diabetes Mall [online] "Syndrome X," Feb. 2002, retrieved on Sep. 24, 2014, retrieved from URL <https://www.diabetesnet.com/about-diabetes/types-diabetes/syndrome-x>, 1 page.
The Pocket Oxford American Dictionary of Current English, "Advise" and "Prescribe" Oxford University Press, New York: 2002, pp. 11 and 623.
Thompson et al., "N6,9-Disubstituted Adenines: Potent, Selective Antagonists at the A1 Adenosine Receptor," J. Med. Chem. (1991) 34:2877-2882.
Thompson et al., "Synthesis and evaluation of 6-(dibromomethyl)-5-nitropyrimidines as potential antitumor agents," J Med Chem (1997) 40(5):766-770.
Tilg and Moschen, "Adipocytokines: mediators linking adipose tissue, inflammation and immunity," Nat. Rev. Immunol., 2006, 2006, 6:772-783.
Trejo et al., "Design and Synthesis of 4-Azaindoles as Inhibitors of p38 MAP Kinase," J. Med. Chem., (2003) 46:4702-4713.
Truong et al., "Human Islet Function is not Impaired by the Sphingosine-1-Phosphate Receptor Modulator FTY720," Am J Transplantation, 2007, 7:2031-2038.
Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.
Tseng and Liu, "Peptide YY and cancer: current findings and potential clinical applications," Peptides, 2002, 23:389-395.
Tsukiyama et al., "Gastric Inhibitory Polypeptide as an Endogenous Factor Promoting New Bone Formation after Food Ingestion," Mol Endocrinol., 2006, 20:1644-1651.
Tuomilehto et al., "A Review of the Efficacy of Rosuvastatin in Patients with Type 2 Diabetes," International Journal of Clinical Practice, Supplement, 143, 30-40 (2004).
Turck et al., "Advances in the directed metallation of azines and diazines (pyridines, pyrimidines, pyrazines, pyridazines, quinolones, benzodiazines and carbolines). Part 2: Metallation of pyrimidines, pyrazines, pyridazines and benzodiazines," Tetrahedron (2001) 57(21):4489-4505.
U.S. Department of Health & Human Services National Institutes of Health [online], "Pyoderma gangrenosum," Last updated Aug. 15, 2016, retrieved on Aug. 20, 2019, 7 pages.
Ueno et al., "The role of PYY in feeding regulation," Regul Pept., 2008, 145:12-16.
Ulrich, "Crystallization," Kirk-Othmer Encyclopedia of the Chemical Technology, 2002, Chapter 4, 8:95-147.
United States Pharmacopeial Convention, USP35 NF30, 2012: U. S. Pharmacopoeia National Formulary, Optical Microscopy, Physical Tests, 2012, 331-334.
University of Maryland Medical Center [online], "Familial hypercholesterolemia," 2011, retrieved on Jul. 2, 2011, retrieved from URL <http://www.umm.edu/ency/article/00392prv.htm>, 4 pages.
Ural et al., "Treatment with Cerivastatin in Primary Mixed Hyperlipidemia Induces Changes in Platelet Aggregation and Coagulation System Components," International Journal of Hematology, 76(3):279-283 (2002).
Urgaonkar et al., "Pd/P(i-BuNCH2CH2)3N: an efficient catalyst for Suzuki cross-coupling of aryl bromides and chlorides with arylboronic adds," Tetrahedron Letters (2002) 43(49):8921-8924.
Urwyler et al., "N,N'-Dicyclopentyl-2-methylsulfanyl-5-nitro-pyrimidine-4,6-diamine (GS39783) and Structurally Related Compounds: Novel Allosteric Enhancers of γ-Aminobutyric AcidB Receptor Function," Journal of Pharmacology and Experimental Therapeutics 2003, 307(1):322-330.
Vachal et al., "Highly selective and potent agonists of sphinogosin-1-phosphate 1 (S1P1) receptor," Bioorganic Med Chem Lett., Jul. 2006, 16(14):3684-3687.
Vaclavkova et al., "Oral ponesimod in patients with chronic plaque psoriasis: a randomised, double-blind, placebo-controlled phase 2 trial," Lancet, 2014, 384(9959):2036-45.
Valdimarsson et al., "Psoriasis—as an autoimmune disease caused by molecular mimicry," Trends in Immunology, Oct. 2009, 30(10):494-501.
Variankaval and Cote, "From form to function: Crystallization of active pharmaceutical ingredients," AIChe Journal, Jul. 2008, 54(7): 1682-1688.
Vascular Web [online], "Hyperlipidemia," 2010, retrieved on Jan. 28, 2011, retrieved from URL http://www.vascularweb.org/patients/NorthPoint/Hyperlipidemia.html>, 5 pages.
Vaughan et al., "The Reformatsky Reaction. I. Zinc and Ethyl α-Bromoisobutyrate," J. Org. Chem, Jun. 1965, 30:1790-1795.

(56) References Cited

OTHER PUBLICATIONS

Vavricka et al., "Extraintestinal manifestations of inflammatory bowel disease," Inflammatory Bowel Diseases, 2015, 21(8):1982-1992.
Vice et al., "Concise Formation of 4-Benzyl Piperidines and Related Derivatives Using a Suzuki Protocol," J. Org. Chem. (2001) 66:2487-2492, Supporting Information, pp. S1-S32.
Vice et al., "Concise Formation of 4-Benzyl Piperidines and Related Derivatives Using a Suzuki Protocol," J. Org. Chem. (2001) 66:2487-2492.
Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties," J. Med. Chem., 2003, 46:2774-2789.
Villhauer et al., "1-[2-[(5-Cyanopyridin-2-yl)amino]-ethylamino]acetyl-2-(S)-pyrrolidine-carbonitrile: A Potent, Selective, and Orally Bioavailable Dipeptidyl Peptidase IV Inhibitor with Antihyperglycemic Properties," J. Med. Chem., 2002, 45:2362-2365.
Villullas et al, "Characterisation of a Sphingosine 1-Phosphate-Activated Ca2+ Signalling Pathway in Human Neuroblastoma Cells," J. Neurosci. Res, 73:215-226, 2003.
Vinogradov et al., "Synthesis and reactions of 1-aryl-3-formyl-4,6-dinitro-1H-indazoles," Mendeleev Communications, 2002, (5), 198-200.
Vippagunta, et al., "Crystalline Solids," Adv. Drug Delivery Rev., 48:3-26 (2001).
Von den Driesch, "Pyoderma gangrenosum: a report of 44 cases with follow-up," Br. J. Dermatol, 1997, 137(6):1000-5.
Vona-Davis and McFadden, "PYY and the pancreas: Inhibition of tumor growth and inflammation," Peptides, 2007, 28:334-338.
Wang et al., "Amino-substituted heterocycles as isosteres of trans-cinnamides: design and synthesis of heterocyclic biaryl sulfides as potent antagonists of LFA-1/ICAM-1 binding," Bioorganic & Medicinal Chemistry Letters, 15(1), 195-201 (2005).
Wang et al., "Improving the Oral Efficacy of CNS Drug Candidates: Discovery of Highly Orally Efficacious Piperidinyl Piperidine M2 Muscarinic Receptor Antagonists," J Med Chem (2002). 45(25):5415-5418.
Webb et al., "Sphingosine 1-phosphate receptors agonists attenuate relapsing-remitting experimental autoimmune encephalitis in SJL mice," J Neuroimmunol, 2004, 153:108-121.
Weber et al., "Microbic Superinfection in Relapse of Inflammatory Bowel Disease," J Clin Gastroenterol., 1992, 14(4):302-308.
Webmd.com [online], "Type I Diabetes Prevention," retrieved on May 26, 2009. Retrieved from URL <http://diabetes.webmd.com/tc/type-1-diabetes-prevention>, 3 pages.
Webster, "The Pathophysiology of Acne," Cutis, 2005, 76(suppl. 2):4-7.
Weenig et al., "Skin ulcers misdiagnosed as pyoderma gangrenosum," N Engl J Med, 2002, 347:1412-1418.
Wells et al., Regioselective nucleophilic substitutions of fluorobenzene derivatives, Tetrahedron Letters, (1996) 37(36):6439-6442.
Werbel et al., "Synthesis and antimalarial effects of 5,6-dichioro-2-[(4-[[ [4-(diethylamino)1-methylbutyl]amino [[-6-methyl-2-pyrimidinyl)amino] benzimidazole and related benzimidazoles and I,H-Imidazo[4,5-b] pyridines," J. Het. Chem (1973) vol. 10, 363-382.
West, Solid State Chemistry and its application, New York, 1988, pp. 358 & 365.
Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.
Wikipedia [online], "Fingolimod," last edited on Feb. 5, 2022, retrieved on Mar. 23, 2022, retrieved from URL <https://en.wikipedia.org/wiki/Fingolimod>, 7 pages.
Wilson et al., "Microwave-assisted synthesis of 2-aminoquinolines," Tetrahedron Letters (2002) 43(4):581-583.
Winkelmann et al., "Haplotypes of the Cholesteryl Ester Transfer Protein Gene Predict Lipid-Modifying Response to Statin Therapy," Germany Pharmacogenomics Journal, 3(5): 284-296 (2003).
Woldbye et al., "Differential suppression of seizures via Y2 and Y5 neuropeptide Y receptors," Neurobiology of Disease, 2005, 20:760-772.
Wolfe et al., "Scope and limitations of the Pd/BINAP-catalyzed amination of aryl bromides," J Org Chem, 2000, 65(4):1144-1157.
Wolfe et al., "Simple, efficient catalyst system for the palladium-catalyzed amination of aryl chlorides, bromides, and triflates," J Org Chem, 2000, 65(4):1158-1174.
Wollina, "Pyoderma gangrenosum—a review," Orphanet Journal of Rare Diseases; 2007, 2:19.
Wolter et al., "Copper-Catalyzed Coupling of Aryl Iodides with Aliphatic Alcohols," Organic Letters, 2002, 4(6):973-976.
Wolter et al., "Copper-Catalyzed Coupling of Aryl Iodides with Aliphatic Alcohols," Organic Letters, 2002, 4(6):973-976, Supporting Information, pp. S1-S16.
World Health Organization Technical Report Series 921, "Prevention and Management of Osteopoosis," 2003, 206 pages.
World IBD Day [online], "World IBD Day," 2019, retrieved on Aug. 20, 2019, retrieved from URL <https://worldibdday.org/>, 6 pages.
Wortley et al., "Peptide YY Regulates Bone Turnover in Rodents," Gastroenterol., 2007, 133:1534-1543.
Wu et al., "One-Pot Two-Step Microwave-Assisted Reaction in Constructing 4,5-Disubstituted Pyrazolopyrimidines," Org. Lett., (2003) 5(20):3587-3590.
Xia et al., "Discovery of a nortropanol derivative as a potent and orally active GPR119 agonist for type 2 diabetes," Bioorganic Med. Chem. Lett., 2011, 21:3290-3296.
Xie et al., "Glucose-dependent insulinotropic polypeptide receptor knockout mice have altered bone turnover," Bone, 2005 37:759-769.
Xu et al., "Safety, pharmacokinetics, pharmacodynamics, and bioavailability of GSK2018682, a sphingosine-1-phosphate receptor modulator, in healthy volunteers," Am College of Clinical Pharm, 2014, 3(3): 170-178.
Yamamoto et al., "Correlation of the adipocyte-derived protein adiponectin with insulin resistance index and serum high-density lipoprotein-cholesterol, independent of body mass index, in the Japanese population," Clinical Science, 2002, 103:137-142.
Yamamoto, "Crohn's disease and mucocutaneous conditions," Journal of Clinical and Experimental Dermatology Research, 2014 4(2):1-6.
Yan et al., "Discovery of 3-arylpropionic acids as potent agonists of sphingosine-1-phosphate receptor-1 (S1P1) with high selectivity against all other known S1P receptor subtypes," Bioorg. Med. Chem. Lett., 2006, 16:3679-3683.
Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But not cytokine production in vivo," J Immunol., 1998, 160:5493-5499.
Yang et al., "Sphingosine kinase/sphingosine 1-phosphate (S1P)/S1P receptor axis is involved in liver fibrosis-associated angiogenesis," J Hepatol., 2013, 59(1):114-23.
Yang et al., "The immune modulator FYT720 prevents autoimmune diabetes in nonobese diabetic mice," Clin. Immunol., 2003, 107:30-35.
Yarovenko et al., "New method for the preparation of 5-amino-1,2,4-oxadiazoles," Bull Acad Sci, USSR Div Chem Sci, (1991) 40:1924.
Yates et al., "Further evidence for an association between psoriasis, Crohn's disease and ulcerative colitis," Br J Dermatol, 1982, 106(3):323-330.
Yokota et al., "Adiponectin, a new member of the family of soluble defense collagens, negatively regulates the growth of myelomonocytic progenitors and the functions of macrophages," Blood, 2000, 96:1723-1732.
Yoon et al., "Reaction of Diisobutylaluminum Hydride with Selected Organic Compounds Containing Representative Functional Groups," J. Org. Chem., (1985) 50:2443-2450.
Yoshida et al., "AS1907417, a novel GPR119 agonist, as an insulinotropic and β-cell preservative agent for the treatment of type 2 diabetes," Biochemical and Biophysical Research Communications, 2010, 400:745-751.

(56) References Cited

OTHER PUBLICATIONS

Yuan et al., "3-Aryl pyrazolo[4,3-d]pyrimidine derivatives nonpeptide CRF-1 antagonists," Bioorganic Medicinal Chemistry Lett. (2002) 2133-2136.

Zamponi et al., "Unique structure-activity relationship for 4-isoxazolyl-1,4-dihydropyridines," J Med Chem (2003) 46:87-96.

Zamponi et al., "Unique structure-activity relationship for 4-isoxazolyl-1,4-dihydropyridines," J Med Chem (2003), Supporting Information., pp. 1-31.

Zander et al., "Effect of 6-week course of glucagon-like peptide 1 on glycaemic control, insulin sensitivity, and β-cell function in type 2 diabetes: a parallel-group study," Lancet, 2002, 359:824-830.

Zhang et al., "FTY720 attenuates accumulation of EMAP-II+ and MHC-II+ monocytes in early lesions of rat traumatic brain injury," J Cell Mol Med., 2007, 11(2):307-314.

Zhang et al., "FTY720: A Most Promising Immunosuppressant Modulating Immune Cell Functions," Mini Rev. Med Chem., 2007, 7:845-850.

Zhang, et al., "Preparation of 1-(Tri-n-Butylstannyl) Furanoid Glycals and Their Use in Palladium-Mediated Coupling Reactions," Tetrahedron Letters (1993) 34(10):1571-1574.

Zhong et al., "Effects of glucose-dependent insulinotropic peptide on osteoclast function," Am J Physiol Endocrinol Metab, 2007, 292:E543-E548.

Zhu et al., "Synthesis and Mode of Action of 125I-and 3H-Labeled Thieno[2,3-c]pyridine Antagonists of Cell Adhesion Molecule Expression," J. Org. Chem., 2002, 67(3):943-948.

Zon and Peterson, "In vivo Drug Discovery in the Zebrafish," Nature Reviews, Jan. 2005, 4:35-44.

Cheng, et al., "Food Effects on Oral Drug Absorption: Application of Physiologically-Based Pharmacokinetic Modeling as a Predictive Tool", Pharmaceuticals, 12, 672 (2020).

* cited by examiner

Compound 1 Mean Plasma Concentration-Time Profiles
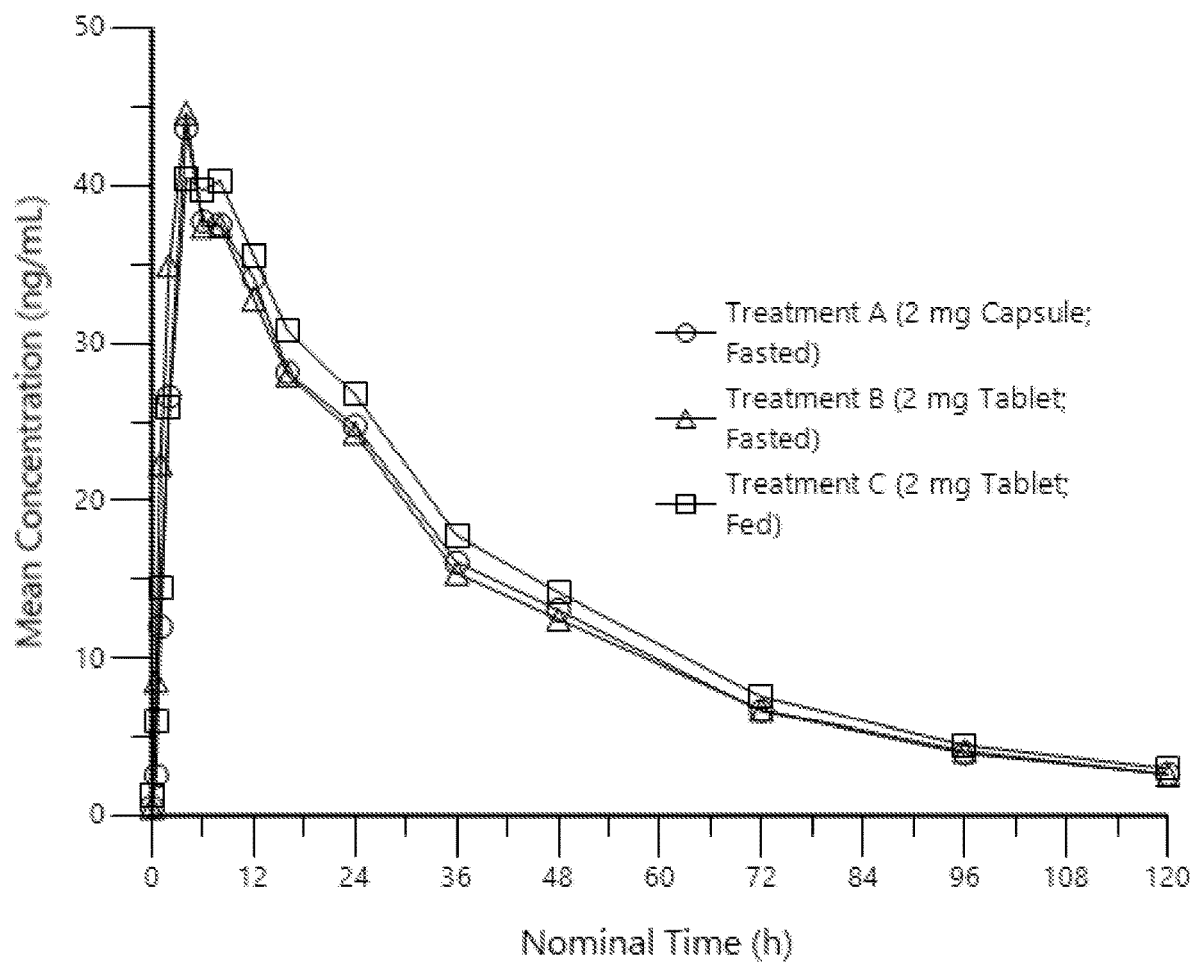

METHODS OF TREATING CONDITIONS RELATED TO THE S1P₁ RECEPTOR

CROSS-REFERENCE TO RELATED APPLICATIONS

This is a national phase application of International Application No. PCT/US2019/035662 filed on Jun. 5 2019, and published in the English language, which claims the benefit of provisional application U.S. 62/681,426, filed on Jun. 6, 2018, provisional application U.S. 62/746,946, filed on Oct. 17, 2018, and provisional application U.S. 62/850,470, filed on May 20, 2019, each of which is incorporated by reference in its entirety.

FIELD

Provided are methods useful in the treatment of sphingosine 1-phosphate subtype 1 ($S1P_1$ or S1P1) receptor-associated disorders.

The sphingosine-1-phosphate (SIP) receptors 1-5 constitute a family of G protein-coupled receptors with a seven-transmembrane domain. These receptors, referred to as $S1P_1$ to $S1P_5$ (formerly termed endothelial differentiation gene (EDG) receptor-1, -5, -3, -6, and -8, respectively; Chun et al., *Pharmacological Reviews*, 54:265-269, 2002), are activated via binding by sphingosine-1-phosphate. which is produced by the sphingosine kinase-catalyzed phosphorylation of sphingosine. $S1P_1$, $S1P_4$ and $S1P_5$ receptors activate Gi but not Gq, whereas $S1P_2$ and $S1P_3$ receptors activate both Gi and Gq. The $S1P_3$ receptor, but not the $S1P_1$ receptor, responds to an agonist with an increase in intracellular calcium.

In view of the growing demand for SIP; agonists useful in the treatment of $S1P_1$ receptor-associated disorders, the compound (R)-2-(7-(4-cyclopentyl-3-(trifluoromethyl)benzyloxy)-1,2,3,4-tetrahydrocyclopenta[b]indol-3-yl)acetic acid (Compound 1, APD334), or a pharmaceutically acceptable salt, solvate, or hydrate thereof,

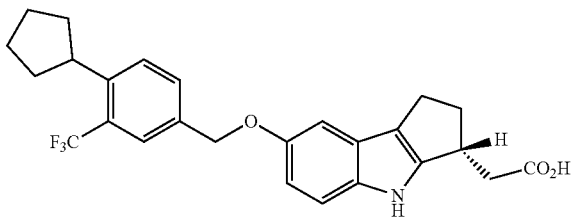 [SMILES: O=C(O)C[C@H]1CCc2c1[nH]c1ccc(OCc3ccc(C4CCCC4)c(C(F)(F)F)c3)cc21]

has emerged as an important new compound, see PCT patent application, Serial No. PCT/US2009/004265 hereby incorporated by reference in its entirety. Compound 1, or a pharmaceutically acceptable salt, solvate, or hydrate thereof, is an investigational drug candidate intended for the treatment of sphingosine 1-phosphate subtype 1 ($S1P_1$) receptor-associated disorders.

Many $S1P_1$ agonists cause side effects, and particularly cardiovascular related adverse events, that require that doctors titrate patients slowly to a maintenance dose. This titration period can take weeks or even a month. The complexity and length of the titration regimen may result in prematurely discontinuing therapy by patients prior to reaching the maintenance dose or to doctors preferring other therapeutic options.

There exists a need for effectively treating individuals who are in need of treatment with Compound 1, or a pharmaceutically acceptable salt, solvate, or hydrate thereof. The present disclosure satisfies this need and provides related advantages as well.

Citation of any reference throughout this application is not to be construed as an admission that such reference is prior art to the present application.

SUMMARY

Provided is a method of treating an individual with a sphingosine 1-phosphate subtype 1 ($S1P_1$) receptor-associated disorder comprising: administering to the individual in need thereof a pharmaceutical dosage form comprising a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, wherein the pharmaceutical dosage form has a mean fed/fasted ratio of the area under the plasma concentration versus time curve of from about 0.8 to about 1.25 and a mean fed/fasted ratio of the maximum plasma concentration (Cmax) from about 0.8 to about 1.25.

Also provided is a method of administering a sphingosine 1-phosphate subtype 1 (SIP)) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof wherein the patient is also being administered a cytochrome P450 2C8 (CYP2C8) inhibitor, cytochrome P450 2C9 (CYP2C9) inhibitor, UDP-glucuronosyltransferase (UGT) enzyme UGT1A1 inhibitor, or UDP-glucuronosyltransferase (UGT) enzyme UGT1A6 inhibitor, comprising: administering to the patient a therapeutically effective amount of the $S1P_1$ modulator, wherein the therapeutically effective amount of the $S1P_1$ modulator is less than the amount that would be administered to a patient who is not also being administered a CYP2C8 inhibitor, CYP2C9 inhibitor, UGT1A1 inhibitor, or UGT1A6 inhibitor.

Also provided is a method of administering a sphingosine 1-phosphate subtype 1 ($S1P_1$) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof, comprising: administering to the patient a therapeutically effective amount of the $S1P_1$ modulator, subsequently determining that the patient is to begin treatment with a CYP2C8 inhibitor. CYP2C9 inhibitor, UDP-glucuronosyltransferase (UGT) enzyme UGT1A1 inhibitor, or UDP-glucuronosyltransferase (UGT) enzyme UGT1A6 inhibitor and administering the $S1P_1$ modulator in an amount that is less than the amount that would be administered to a patient who is not also being administered CYP2C8 inhibitor, CYP2C9 inhibitor, UDP-glucuronosyltransferase (UGT) enzyme UGT1A1 inhibitor, or UDP-glucuronosyltransferase (UGT) enzyme UGT1A6 inhibitor.

Also provided is a method of administering a sphingosine 1-phosphate subtype 1 ($S1P_1$) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof wherein the patient is also being administered a substrate of a membrane transporter wherein the membrane transporter is selected from P-glycoprotein (Pgp), BCRP (breast cancer resistance protein), and OATP1B1, comprising: administering to the patient a therapeutically effective amount of the S1P$_1$ modulator.

Also provided is a method of administering a sphingosine 1-phosphate subtype 1 (S1P$_1$) receptor modulator chosen from R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt and/or isotopic variant thereof, to a patient in need thereof, comprising: administering to the patient a therapeutically effective amount of the S1P$_1$ receptor modulator, subsequently determining that the patient is to begin treatment with a substrate of a membrane transporter wherein the membrane transporter is selected from P-glycoprotein (Pgp), BCRP (breast cancer resistance protein), and OATP1B1, and continuing administration of the therapeutically effective amount of the S1P$_1$ receptor modulator to the patient.

These and other aspects of the invention disclosed herein will be set forth in greater detail as the patent disclosure proceeds.

BRIEF DESCRIPTION OF THE DRAWINGS

FIG. 1 shows the mean plasma concentration-time profiles for the tablet formulation of Compound 1 administered under fed versus fasted conditions.

DETAILED DESCRIPTION

As used in the present specification, the following words and phrases are generally intended to have the meanings as set forth below, except to the extent that the context in which they are used indicates otherwise.

COMPOUND 1: As used herein, "Compound 1" means (R)-2-(7-(4-cyclopentyl-3-(trifluoromethyl)benzyloxy)-1,2,3,4-tetrahydrocyclopenta[b]indol-3-yl)acetic acid including crystalline forms thereof. As a non-limiting example, Compound 1 may be present as an anhydrous, non-solvated crystalline form as described in WO 2010/011316 (incorporated by reference herein in its entirety). As another non-limiting example, an L-arginine salt of Compound 1 may be present as an anhydrous, non-solvated crystalline form as described in WO 2010/011316 and WO 2011/094008 (each of which is incorporated by reference herein in its entirety). As another non-limiting example, a calcium salt of Compound 1 may be present as a crystalline form as described in WO 2010/011316 (incorporated by reference herein in its entirety).

ADMINISTERING: As used herein. "administering" means to provide a compound or other therapy, remedy, or treatment such that an individual internalizes a compound.

CO-ADMINISTER: As used herein, "co-administer" and "co-administration" and variants thereof mean the administration of at least two drugs to a patient either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

PRESCRIBING: As used herein, "prescribing" means to order, authorize, or recommend the use of a drug or other therapy, remedy, or treatment. In some embodiments, a health care practitioner can orally advise, recommend, or authorize the use of a compound, dosage regimen or other treatment to an individual. In this case the health care practitioner may or may not provide a prescription for the compound, dosage regimen, or treatment. Further, the health care practitioner may or may not provide the recommended compound or treatment. For example, the health care practitioner can advise the individual where to obtain the compound without providing the compound. In some embodiments, a health care practitioner can provide a prescription for the compound, dosage regimen, or treatment to the individual. For example, a health care practitioner can give a written or oral prescription to an individual. A prescription can be written on paper or on electronic media such as a computer file, for example, on a hand-held computer device. For example, a health care practitioner can transform a piece of paper or electronic media with a prescription for a compound, dosage regimen, or treatment. In addition, a prescription can be called in (oral), faxed in (written), or submitted electronically via the internet to a pharmacy or a dispensary. In some embodiments, a sample of the compound or treatment can be given to the individual. As used herein, giving a sample of a compound constitutes an implicit prescription for the compound. Different health care systems around the world use different methods for prescribing and/or administering compounds or treatments and these methods are encompassed by the disclosure.

A prescription can include, for example, an individual's name and/or identifying information such as date of birth. In addition, for example, a prescription can include: the medication name, medication strength, dose, frequency of administration, route of administration, number or amount to be dispensed, number of refills, physician name, physician signature, and the like. Further, for example, a prescription can include a DEA number and/or state number.

A healthcare practitioner can include, for example, a physician, nurse, nurse practitioner, or other related health care professional who can prescribe or administer compounds (drugs) for the treatment of a sphingosine 1-phosphate subtype 1 (S1P$_1$) receptor-associated disorder. In addition, a healthcare practitioner can include anyone who can recommend, prescribe, administer, or prevent an individual from receiving a compound or drug including, for example, an insurance provider.

PREVENT, PREVENTING, OR PREVENTION: As used herein, the term "prevent," "preventing", or "prevention" such as prevention of a sphingosine 1-phosphate subtype 1 (S1P$_1$) receptor-associated disorder or the occurrence or onset of one or more symptoms associated with the particular disorder and does not necessarily mean the complete prevention of the disorder. For example, the term "prevent," "preventing" and "prevention" means the administration of therapy on a prophylactic or preventative basis to an individual who may ultimately manifest at least one symptom of a disease or condition but who has not yet done so. Such individuals can be identified on the basis of risk factors that are known to correlate with the subsequent occurrence of the disease. Alternatively, prevention therapy can be administered without prior identification of a risk factor, as a prophylactic measure. Delaying the onset of at least one symptom can also be considered prevention or prophylaxis.

TREAT, TREATING, OR TREATMENT: As used herein the term "treat," "treating", or "treatment" means the administration of therapy to an individual who already manifests at least one symptom of a disease or condition or who has previously manifested at least one symptom of a disease or condition. For example, "treating" can include alleviating, abating or ameliorating a disease or condition symptoms, preventing additional symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. For example, the term "treating" in reference to a disorder means a reduction in severity of one or more symptoms associated with that particular disorder. Therefore, treating a disorder does not necessarily mean a reduction in severity of all symptoms associated with a disorder and does not necessarily mean a complete reduction in the severity of one or more symptoms associated with a disorder.

TOLERATE: As used herein, an individual is said to "tolerate" a dose of a compound if administration of that dose to that individual does not result in an unacceptable adverse event or an unacceptable combination of adverse events. One of skill in the art will appreciate that tolerance is a subjective measure and that what may be tolerable to one individual may not be tolerable to a different individual. For example, one individual may not be able to tolerate headache, whereas a second individual may find headache tolerable but is not able to tolerate vomiting, whereas for a third individual, either headache alone or vomiting alone is tolerable, but the individual is not able to tolerate the combination of headache and vomiting, even if the severity of each is less than when experienced alone.

ADVERSE EVENT: As used herein, an "adverse event" is an untoward medical occurrence that is associated with treatment with Compound 1 or a pharmaceutically acceptable salt, solvate, or hydrate thereof. In one embodiment, an adverse event is selected from: leukopenia, constipation, diarrhea, nausea, abdominal pain, neutropenia, vomiting, back pain, and menstrual disorder. In one embodiment, an adverse event is heart block, for example, a first-degree atrioventricular heart block. In one embodiment, an adverse event is an acute heart rate reduction. In one embodiment, an adverse event is an abnormal pulmonary function test finding, such as an FEV1 below 80%, FVC. In one embodiment, an adverse event is an abnormal liver function test, such as an elevated ALT & AST>2X ULN. In one embodiment, an adverse event is macular edema.

IN NEED OF TREATMENT and IN NEED THEREOF: As used herein. "in need of treatment" and "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly. the compounds of the invention can be used in a protective or preventive manner; or compounds of the invention can be used to alleviate, inhibit or ameliorate the disease, condition or disorder.

INDIVIDUAL: As used herein, "individual" means any animal, including mammals, preferably mice, rats, other rodents, rabbits, dogs, cats, swine, cattle, sheep, horses, or primates and most preferably humans. In some embodiments, a human individual is referred to a "patient."

ACUTE HEART RATE REDUCTION: As used herein, "acute heart rate reduction" means a heart rate decrease from normal sinus rhythm of, for example, 10 or more beats per minute (bpm), such as less than about 5 bpm, e.g., less than about 4 bpm or less than about 3 bpm or less than 2 bpm, that is maximal within a few hours, for example 1-3 hours, after drug administration, and thereafter the heart rate returns towards the pre-dose value.

NORMAL SINUS RHYTHM: As used herein, "normal sinus rhythm" means the sinus rhythm of the individual when not undergoing treatment. The evaluation of normal sinus rhythm is within the ability of a physician. A normal sinus rhythm will generally give rise to a heart rate in the range from 60-100 bpm.

DOSE: As used herein, "dose" means a quantity of Compound 1, or a pharmaceutically acceptable salt, solvate, or hydrate thereof, given to the individual for treating or preventing the disease or disorder at one specific time.

STANDARD DOSE: As used herein, "standard dose" means the dose of Compound 1, or a pharmaceutically acceptable salt, solvate, or hydrate thereof, that is given to the individual for treating or preventing the disease or disorder. In some embodiments, administration of the standard dose achieves a target reduction in peripheral blood lymphocyte counts, e.g., a reduction in baseline of at least 35%, such as at least 40%, such as at least 45%, such as at least 50%, such as at least 55%, such as at least 60%, such as at least 65%, such as at least 70%. In some embodiments, administration of the standard dose achieves a reduction in baseline of about 35% to about 70%, such as about 40% to about 65%, such as about 50% to about 65%. In some embodiments, administration of the standard dose achieves target peripheral blood lymphocyte counts, e.g., less than 1000 lymphocytes per microliter, such as 400-800 lymphocytes per microliter. The target dose may vary depending on the nature and severity of the disease to be treated.

THERAPEUTICALLY EFFECTIVE AMOUNT: As used herein, "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician. In some embodiments, the therapeutically effective amount is the standard dose.

FASTED INDIVIDUAL: As used herein, "fasted individual" means an individual who has not eaten any food, i.e., has fasted for at least 6-8 hours, such as about 8 hours, before the administration of Compound 1, or a pharmaceutically acceptable salt, hydrate, or solvate thereof, and who does not eat any food and continues to fast for at least 1 hour after the administration of Compound 1, or a pharmaceutically acceptable salt, hydrate, or solvate thereof. In certain embodiments, the individual may also refrain from ingesting certain non-food substances during the fasting period. For example, in certain embodiments the individual does not ingest any supplements and/or drugs during the fasting period. In certain embodiments, the individual does not ingest any high calorie liquids during the fasting period. In certain embodiments, the individual does not ingest any liquids other than water during the fasting period. In certain embodiments, the individual may ingest small amounts of low-calorie beverages, such as tea, coffee, or diluted juices.

MAYO CLINIC SCORE (MCS): As used herein, "Mayo Clinic Score" or "MCS" means an instrument designed to measure disease activity of ulcerative colitis and consists of up to 4 subscores: stool frequency, rectal bleeding, findings of flexible proctosigmoidoscopy, and physician global assessment with each component ranging from 0 to 3 (0=normal, 1=mild, 2=moderate, 3=severe). Total score therefore ranges from 0 to 12, with a higher score indicating more severe disease. The 6-point Mayo score is based on stool frequency and rectal bleeding PROs collected daily using electronic patient diaries and excludes the findings on endoscopy and the physician's global assessment. The 3-point Mayo score is based on stool frequency, rectal bleeding, and findings on endoscopy and has a total score ranging from 0 to 9. The 2-point Mayo score is based on rectal bleeding and findings on endoscopy and has a total score ranging from 0 to 6. The physician's global assessment acknowledges the three other criteria findings of the MCS, the individual's daily record of abdominal discomfort and general sense of well-being, and other observations, such as physical findings and the individual's performance.

MILDLY TO MODERATELY ACTIVE ULCERATIVE COLITIS: As used herein, "mildly to moderately active ulcerative colitis" means ulcerative colitis characterized by a 4-component MCS of 4 to 10.

MODERATELY TO SEVERELY ACTIVE ULCERATIVE COLITIS: As used herein, "moderately to severely active ulcerative colitis" means ulcerative colitis characterized by a 3-component MCS of 4 to 9 including an endoscopic subscore of ≥2 and a rectal bleeding score of ≥1. The 3-component MCS uses 3 of the 4 components of the complete MCS (endoscopic findings, rectal bleeding, and stool frequency).

CLINICAL REMISSION: As used herein, "clinical remission" with respect to ulcerative colitis means a 3-component Mayo Clinic score as follows: an endoscopy score (using flexible proctosigmoidoscopy) of 0) or 1, a rectal bleeding score of 0, and a stool frequency score of 0) or 1 with a decrease of ≥1 point from baseline subscore.

CLINICAL RESPONSE: As used herein, "clinical response" with respect to ulcerative colitis means a reduction in the 3-component Mayo Clinic score of ≥2 points and a decrease of ≥30% from baseline with an accompanying decrease in rectal bleeding subscore of ≥1 or absolute rectal bleeding score of 0) or 1.

ENDOSCOPIC IMPROVEMENT: As used herein, "endoscopic improvement" with respect to ulcerative colitis means ulcerative colitis characterized by a Mayo endoscopic subscore (using findings of flexible proctosigmoidoscopy) of ≤1 point.

ENDOSCOPIC REMISSION: As used herein. "endoscopic remission" with respect to ulcerative colitis means ulcerative colitis characterized by findings from flexible proctosigmoidoscopy subscore of the Mayo Clinic score=0.

IMPROVEMENT IN RECTAL BLEEDING: As used herein. "improvement in rectal bleeding" with respect to ulcerative colitis means a change from baseline <0.

HISTOLOGIC HEALING/HISTOLOGIC IMPROVEMENT: As used herein, "histologic healing." "histological healing," "histologic improvement," or "histological improvement" with respect to ulcerative colitis means a score of <3.1 on the Geboes Index.

HISTOLOGIC REMISSION: As used herein, "histologic remission" or "histological remission" with respect to ulcerative colitis means a score of <2.0 on the Geboes Index.

MUCOSAL HEALING: As used herein, "mucosal healing" is both endoscopic improvement and histological remission.

IMPROVEMENT IN STOOL FREQUENCY: As used herein, "improvement in stool frequency" with respect to ulcerative colitis means a change from baseline <0. 5-AMINOSALICYLATES: As used herein, "5-aminosalicylates", means a class of drugs that include, for example, CANASA® (mesalamine), COLAZAL® (balsalazide disodium), ASACOL® (mesalamine). DELZICOL® (mesalamine), and DIPENTUM® (olsalazine).

IMMUNOSUPPRESSIVES: As used herein. "immunosuppressives", means a class of drugs that include, for example, AZASAN® (azathioprine), IMURAN® (azathioprine), GENGRAF® (cyclosporine), NEORAL® (cyclosporine), and SANDIMMUNE® (cyclosporine).

GLUCOCORTICOSTEROIDS: As used herein, "glucocorticosteroids", means a class of drugs that include, for example, UCERIS® (budesonide): DELTASONE® (prednisone). MEDROL® (methylprednisolone), and hydrocortisone.

TNFα ANTAGONISTS: As used herein, "TNFα antagonists" or "tumor necrosis factor-α antagonists", means a class of drugs that include, for example, SIMPONI® (golimumab), REMICADE® (infliximab), HUMIRA® (adalimumab), and CIMZIA® (certolizumab pegol).

INTEGRIN RECEPTOR ANTAGONISTS: As used herein, "integrin receptor antagonists", means a class of drugs that include, for example, ENTYVIO® (vedolizumab).

PHARMACEUTICAL COMPOSITION: As used here. "pharmaceutical composition" means a composition comprising at least one active ingredient, such as Compound 1: including but not limited to, salts, solvates, and hydrates of Compound 1, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

AGONIST: As used herein. "agonist" means a moiety that interacts with and activates a G-protein-coupled receptor, such as the $S1P_1$ receptor, such as can thereby initiate a physiological or pharmacological response characteristic of that receptor. For example, an agonist activates an intracellular response upon binding to the receptor or enhances GTP binding to a membrane. In certain embodiments, an agonist of the invention is an $S1P_1$ receptor agonist that is capable of facilitating sustained $S1P_1$ receptor internalization (see e.g., Matloubian et al., Nature, 427, 355, 2004).

ANTAGONIST: As used herein, "antagonist" means a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

INVERSE AGONIST: As used herein, "inverse agonist" means a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. In some embodiments, the baseline intracellular response is inhibited in the presence of the inverse agonist by at least 30%. In some embodiments, the baseline intracellular response is inhibited in the presence of the inverse agonist by at least 50%. In some embodiments, the baseline intracellular response is inhibited in the presence of the inverse agonist by at least 75%, as compared with the baseline response in the absence of the inverse agonist.

HYDRATE: As used herein, "hydrate" means a compound of the invention or a salt thereof, that further includes a stoichiometric or non-stoichiometric amount of water bound by non-covalent intermolecular forces.

SAFETY POPULATION: As used herein, "safety population" means all randomized subjects who received study medication.

SOLVATE: As used herein, "solvate" means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

It is understood that when the phrase "pharmaceutically acceptable salts, solvates and hydrates" or the phrase "pharmaceutically acceptable salt, solvate, or hydrate" is used when referring to Compound 1, it embraces pharmaceutically acceptable solvates and/or hydrates of Compound 1, pharmaceutically acceptable salts of Compound 1, as well as pharmaceutically acceptable solvates and/or hydrates of pharmaceutically acceptable salts of Compound 1. It is also understood that when the phrase "pharmaceutically acceptable solvates and hydrates" or the phrase "pharmaceutically acceptable solvate or hydrate" is used when referring to Compound 1 that are salts, it embraces pharmaceutically acceptable solvates and/or hydrates of such salts.

It will be apparent to those skilled in the art that the dosage forms described herein may comprise, as the active component, either Compound 1 or a pharmaceutically acceptable salt or as a solvate or hydrate thereof. Moreover, various hydrates and solvates of Compound 1 and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95. Marcel Dekker, Inc., New York, 1999. Accordingly, one aspect of the present disclosure pertains to methods of prescribing and/or administering hydrates and solvates of Compound 1 and/or its pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington Pharma Tech (Wilmington, DE). Avantium Technologies (Amsterdam) and Aptuit (Greenwich. CT).

The present disclosure includes all isotopes of atoms occurring in the present compounds, salts, solvates, and hydrates. Isotopes include those atoms having the same atomic number but different mass numbers. One aspect of the present invention includes every combination of one or more atoms in the present compounds, salts, solvates, and hydrates that is replaced with an atom having the same atomic number but a different mass number. One such example is the replacement of an atom that is the most naturally abundant isotope, such as $^1$H or $^{12}$C, found in one the present compounds, salts, solvates, and hydrates, with a different atom that is not the most naturally abundant isotope, such as $^2$H or $^3$H (replacing $^1$H), or $^{11}$C, $^{13}$C, or $^{14}$C (replacing $^{12}$C). When such a replacement has taken place, it is commonly referred to as being isotopically labeled. Isotopic-labeling of the present compounds, salts, solvates, and hydrates can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$O, An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, salts, solvates, and hydrates, wherein the naturally occurring distribution of the isotopes in the composition is perturbed. Another aspect of the present invention includes compositions and pharmaceutical compositions comprising the compounds, salts, solvates, and hydrates, as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Compounds of the present invention can be converted to "prodrugs." The term "prodrugs" means compounds that have been modified with specific chemical groups known in the art and that when administered into an individual undergo biotransformation to give the parent compound.

Prodrugs can thus be viewed as compounds of the invention containing one or more specialized non-toxic protective groups used in a transient manner to alter or to eliminate a property of the compound. In one general aspect, the "prodrug" approach is utilized to facilitate oral absorption. A thorough discussion is provided in T. Higuchi and V. Stella, Prodrugs as Novel Delivery Systems Vol. 14 of the A.C.S. Symposium Series; and in *Bioreversible Carriers in Drug Design*, ed. Edward B. Roche, American Pharmaceutical Association and Pergamon Press. 1987, both of which are hereby incorporated by reference in their entirety.

AUC: As used herein, "AUC" refers to the area under the curve, or the integral, of the plasma concentration of an active pharmaceutical ingredient or metabolite over time following a dosing event.

$AUC_{0-t}$: As used herein "$AUC_{0-t}$" is the integral under the plasma concentration curve from time 0 (dosing) to time "t".

$AUC_{0-\infty}$: As used herein, "$AUC_{0-\infty}$" is the AUC from time 0 (dosing) to time infinity. Unless otherwise stated, AUC refers to $AUC_{0-\infty}$.

Cmax: As used herein, Cmax (or $C_{max}$) is a pharmacokinetic parameter denoting the maximum observed blood plasma concentration following delivery of an active pharmaceutical ingredient. Cmax occurs at the time of maximum plasma concentration, $t_{max}$.

$t_{max}$: As used herein, "$t_{max}$" is a pharmacokinetic parameter denoting the time to maximum blood plasma concentration following delivery of an active pharmaceutical ingredient $t_{1/2}$: As used herein, "$t_{1/2}$" or "plasma half-life" or "elimination half-life" or the like is a pharmacokinetic parameter denoting the apparent plasma terminal phase half-life, i.e., the time, after absorption and distribution of a drug is complete, for the plasma concentration to fall by half.

As used herein. "a substance having a narrow therapeutic index" means a substance falling within any definition of narrow therapeutic index as promulgated by the U.S. Food and Drug Administration or any successor agency thereof, for example, a substance having a less than 2-fold difference in median lethal dose (LD50) and median effective dose (ED50) values or having a less than 2-fold difference in the minimum toxic concentration and minimum effective concentration in the blood; and for which safe and effective use of the substance requires careful titration and patient monitoring.

As used herein, a substance is a "substrate" of enzyme activity when it can be chemically transformed by action of the enzyme on the substance. "Enzyme activity" refers broadly to the specific activity of the enzyme (i.e., the rate at which the enzyme transforms a substrate per mg or mole of enzyme) as well as the metabolic effect of such transformations. Thus, a substance is an "inhibitor" of enzyme activity when the specific activity or the metabolic effect of the specific activity of the enzyme can be decreased by the presence of the substance, without reference to the precise mechanism of such decrease. For example, a substance can be an inhibitor of enzyme activity by competitive, non-competitive, allosteric or other type of enzyme inhibition, by decreasing expression of the enzyme, or other direct or indirect mechanisms. Similarly, a substance is an "inducer" of enzyme activity when the specific activity or the metabolic effect of the specific activity of the enzyme can be increased by the presence of the substance, without reference to the precise mechanism of such increase. For example, a substance can be an inducer of enzyme activity by increasing reaction rate, by increasing expression of the enzyme, by allosteric activation or other direct or indirect mechanisms. Any of these effects on enzyme activity can occur at a given concentration of active agent in a single sample, donor, or patient without regard to clinical significance. It is possible for a substance to be a substrate, inhibitor, or inducer of an enzyme activity. For example, the substance can be an inhibitor of enzyme activity by one mechanism and an inducer of enzyme activity by another mechanism. The function (substrate, inhibitor, or inducer) of the substance with respect to activity of an enzyme can depend on environmental conditions.

When an integer is used in a method disclosed herein, the term "about" can be inserted before the integer.

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps, or group of compositions of matter shall be taken to encompass one and a plurality (i.e. one or more) of those steps, compositions of matter, groups of steps, or groups of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally equivalent products, compositions, and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination. For example, a method that recites prescribing and/or administering Compound 1 or a pharmaceutically acceptable salt, solvate, or hydrate thereof can be separated into two methods; one method reciting prescribing Compound 1 or a pharmaceutically acceptable salt, solvate, or hydrate thereof and the other method reciting administering Compound 1 or a pharmaceutically acceptable salt, solvate, or hydrate thereof. In addition, for example, a method that recites prescribing Compound 1 or a pharmaceutically acceptable salt, solvate, or hydrate thereof and a separate method of the invention reciting administering Compound 1 or a pharmaceutically acceptable salt, solvate, or hydrate thereof can be combined into a single method reciting prescribing and/or administering Compound 1 or a pharmaceutically acceptable salt, solvate, or hydrate thereof.

Provided herein are methods of co-administering Compound 1 with another drug. Also provided herein are methods of reducing the dosage of Compound 1 when co-administered with another drug. Also provided herein are methods of reducing the dosage of another drug when co-administered with Compound 1. Also provided herein are methods of discontinuing the administration of Compound 1 when an individual is administered another drug. Also provided herein are methods of discontinuing the administration of another drug when an individual is administered Compound 1. Also provided herein are methods of continuing the administration of Compound 1 when an individual is administered another drug. Also provided herein are methods of continuing the administration of another drug when an individual is administered Compound 1. Also provided herein are methods of monitoring an individual who is co-administered Compound 1 and another drug. Also provided herein are methods of titrating the dosage of Compound 1 when co-administered with another drug. Also provided herein are methods of titrating the dosage of another drug when co-administered with Compound 1. Also provided herein are methods that entail combinations of the foregoing methods.

Provided is a method of treating an individual with a sphingosine 1-phosphate subtype 1 ($S1P_1$) receptor-associated disorder comprising: administering to the individual in need thereof a pharmaceutical dosage form comprising a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, wherein the pharmaceutical dosage form has a mean fed/fasted ratio of the area under the plasma concentration versus time curve of from about 0.8 to about 1.25 and a mean fed/fasted ratio of the maximum plasma concentration (Cmax) from about 0.8 to about 1.25.

Also provided is a method of administering a sphingosine 1-phosphate subtype 1 (SIP)) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof wherein the patient is also being administered a cytochrome P450 2C8 (CYP2C8) inhibitor, cytochrome P450 2C9 (CYP2C9) inhibitor, UDP-glucuronosyltransferase (UGT) enzyme UGT1A1 inhibitor, or UDP-glucuronosyltransferase (UGT) enzyme UGT1A6 inhibitor, comprising: administering to the patient a therapeutically effective amount of the $S1P_1$ modulator, wherein the therapeutically effective amount of the $S1P_1$ modulator is less than the amount that would be administered to a patient who is not also being administered a CYP2C8 inhibitor, CYP2C9 inhibitor, UGT1A1 inhibitor, or UGT1A6 inhibitor.

Also provided is a method of administering a sphingosine 1-phosphate subtype 1 ($S1P_1$) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof, comprising: administering to the patient a therapeutically effective amount of the $S1P_1$ modulator, subsequently determining that the patient is to begin treatment with a CYP2C8 inhibitor. CYP2C9 inhibitor, UDP-glucuronosyltransferase (UGT) enzyme UGT1A1 inhibitor, or UDP-glucuronosyltransferase (UGT) enzyme UGT1A6 inhibitor and administering the $S1P_1$ modulator in an amount that is less than the amount that would be administered to a patient who is not also being administered CYP2C8 inhibitor, CYP2C9 inhibitor, UDP-glucuronosyltransferase (UGT) enzyme UGT1A1 inhibitor, or UDP-glucuronosyltransferase (UGT) enzyme UGT1A6 inhibitor.

In some embodiments, the method further comprises informing the patient or a medical care worker that administration of the $S1P_1$ modulator to a patient who is also being administered a CYP2C8 inhibitor, CYP2C9 inhibitor, UDP-glucuronosyltransferase (UGT) enzyme UGT1A1 inhibitor, or UDP-glucuronosyltransferase (UGT) enzyme UGT1A6 inhibitor results in higher exposure of the $S1P_1$ modulator than administration of the $S1P_1$ modulator to a patient who is not being administered a CYP2C8 inhibitor. CYP2C9 inhibitor, UDP-glucuronosyltransferase (UGT) enzyme UGT1A1 inhibitor, or UDP-glucuronosyltransferase (UGT) enzyme UGT1A6 inhibitor.

In some embodiments, the method further comprises informing the patient or a medical care worker that administration of the $S1P_1$ modulator to a patient who is also being administered a CYP2C8 inhibitor, CYP2C9 inhibitor, UDP-glucuronosyltransferase (UGT) enzyme UGT1A1 inhibitor, or UDP-glucuronosyltransferase (UGT) enzyme UGT1A6 inhibitor may result in increased risk of one or more exposure-related adverse reactions than administration of the $S1P_1$ modulator to a patient who is not being administered a CYP2C8 inhibitor, CYP2C9 inhibitor, UDP-glucuronosyltransferase (UGT) enzyme UGT1A1 inhibitor, or UDP-glucuronosyltransferase (UGT) enzyme UGT1A6 inhibitor.

In some embodiments, the patient is also being administered a CYP2C8 inhibitor. In some embodiments, the patient is also being administered a CYP2C9 inhibitor. In some embodiments, the patient is also being administered a UDP-glucuronosyltransferase (UGT) enzyme UGT1A1 inhibitor. In some embodiments, the patient is also being administered a UDP-glucuronosyltransferase (UGT) enzyme UGT1A6 inhibitor.

In some embodiments, the CYP2C8 inhibitor is gemfibrozil, ritonavir, clopidogrel, lopinavir, deferasirox, lapatinib, trimethoprim, thiazolidinediones, montelukast, quercetin, candesartan cilexetil (cyclohexylcarbonate ester prodrug of candesartan), zafirlukast, clotrimazole, felodipine, mometasone furoate, salmeterol, raloxifene, fenofibrate, ritonavir, levothyroxine, tamoxifen, loratadine, oxybutynin, medroxyprogesterone, simvastatin, ketoconazole, ethinyl estradiol, spironolactone, lovastatin, nifedipine, or irbesartan. In some embodiments, the CYP2C8 inhibitor is gemfibrozil.

In some embodiments, the CYP2C9 inhibitor is amiodarone, disulfram, doxifluridine, efavirenz, fluconazole, imatinib, lefluonomide, metronidazole, miconazole, phenytoin, sulfamethoxazole, sulfapenazone, sildenafil, zafirlukast, valdecoxib, diclofenac, voriconazole, tamoxifen, losartan, warfarin, etodolac, mefenamic acid, meloxicam, suprofen, irbesartan, ibuprofen, fluvastatin, sertraline, fluvoxamine, pantoprazole, rosiglitazone, lansoprazole, ritonavir, nicardipine, aprepitant, delavirdine, desloratadine, glyburide, ketoconazole, gemfibrozil, acenocoumarol, avasimibe, rosuvastatin, lovastatin, simvastatin, atorvastatin, cerivastatin, quinine, clozapine, or diazepam. In some embodiments, the CYP2C9 inhibitor is fluconazole. In some embodiments, the CYP2C9 inhibitor is gemfibrozil.

In some embodiments, the CYP2C9 inhibitor is ticlopidine, omeprazole, paroxetine, valsartan, bortezomib, valproic acid, nevirapine, azelastine, lornoxicam, fenofibrate, isoniazid, phenylbutazone, probenecid, sulfaphenazole, teniposide, etravirine, sulfadiazine, sulfinpyrazone, sulfisoxazole, trimethoprim, leflunomide, nilotinib, pyrimethamine, sorafenib, capecitabine, fluorouracil, sitaxentan, tranylcypromine, aminophenazone, clopidogrel, verapamil, etoricoxib, propofol, ketoprofen, seratrodast, sulfamoxole, amlodipine, amodiaquine, anastrozole, atovaquone, chloramphenicol, cyclosporine, cimetidine, clotrimazole cocaine, colchicine, cholecalciferol, cyclizine, dexfenfluramine, dextropropoxyphene, dicoumarol, diltiazem, disulfiram, epinephrine, eprosartan, ethanol, felodipine, flecainide, histamine, indinavir, lopinavir, loratadine, medroxyprogesterone acetate, methazolamide, moclobemide, modafinil, nelfinavir, nifedipine, nilutamide, nilvadipine, olanzapine, phentermine, pioglitazone, pranlukast, pravastatin, promethazine, propafenone, quinidine, rutin, saquinavir, selegiline, sulfadimethoxine, sulfamethizole, sulfanilamide, sulfapyridine, tegaserod, methimazole, thioridazine, tioconazole, tolcapone, triazolam, troglitazone, bicalutamide, rabeprazole, armodafinil, diethylstilbestrol, agomelatine, noscapine, clevidipine, cisplatin, human serum albumin, sulconazole, vismodegib, regorafenib, gefitinib, parecoxib, lumacaftor, abiraterone, ticagrelor, ceritinib, floxuridine, crisaborole midostaurin, belinostat, lifitegrast, rhein, diacerein, doconexent, topiroxostat, zucapsaicin, stiripentol, lobeglitazone, dosulepin, benzbromarone, manidipine, enasidenib, candesartan, rucaparib, isavuconazole, cimicifuga racemose, nabilone, acetyl sulfisoxazole, or curcumin.

In some embodiments, the UDP-glucuronosyltransferase (UGT) enzyme UGT1A1 inhibitor is adenine, propofol, indomethacin, nilotinib, pazopanib, regorafenib, flunitrazepam, erlotinib, sorafenib, enasidenib, pibrentasvir, glecaprevir, rucaparib, ertugliflozin, or fostamatinib.

In some embodiments, the UDP-glucuronosyltransferase (UGT) enzyme UGT1A6 inhibitor is troglitazone.

In some embodiments, the UGT substrate is diclofenac.

Also provided is a method of administering a sphingosine 1-phosphate subtype 1 (S1P$_1$) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof wherein the patient is also being administered a substrate of a membrane transporter wherein the membrane transporter is selected from P-glycoprotein (Pgp), BCRP (breast cancer resistance protein), and OATP1B1, comprising: administering to the patient a therapeutically effective amount of the S1P$_1$ modulator.

Also provided is a method of administering a sphingosine 1-phosphate subtype 1 (S1P$_1$) receptor modulator chosen from R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt and/or isotopic variant thereof, to a patient in need thereof, comprising: administering to the patient a therapeutically effective amount of the S1P$_1$ receptor modulator, subsequently determining that the patient is to begin treatment with a substrate of a membrane transporter wherein the membrane transporter is selected from P-glycoprotein (Pgp), BCRP (breast cancer resistance protein), and OATP1B1, and continuing administration of the therapeutically effective amount of the S1P$_1$ receptor modulator to the patient.

In some embodiments, the method further comprises monitoring the patient for signs and symptoms of toxicity and clinical response associated with the substrate of the membrane transporter.

In some embodiments, the method further comprises reducing the amount of the substrate of the membrane transporter administered to the patient based on the patient's ability to tolerate one or more exposure-related adverse reactions related to the substrate of the membrane transporter.

In some embodiments, the method further comprises informing the patient or a medical care worker that co-administration of the S1P$_1$ receptor modulator and the substrate of a membrane transporter may result in increased exposure of the substrate of the membrane transporter.

In some embodiments, the method further comprises informing the patient or a medical care worker that co-administration of the S1P$_1$ receptor modulator and the substrate of the membrane transporter may result in increased risk of one or more exposure-related adverse reactions associated with the substrate of the membrane transporter.

In some embodiments, monitoring for signs and symptoms of toxicity and clinical response comprises monitoring the serum concentration of the substrate of the membrane transporter.

In some embodiments, monitoring for signs and symptoms of toxicity and clinical response comprises determining whether the patient experiences one or more exposure-related adverse reaction associated with serum concentration of the substrate of the membrane transporter.

In some embodiments, monitoring for signs and symptoms of toxicity and clinical response comprises monitoring efficacy of the substrate of the membrane transporter.

In some embodiments, the membrane transporter is P-glycoprotein (Pgp). In some embodiments, the membrane transporter is BCRP (breast cancer resistance protein). In some embodiments, the membrane transporter is OATP1B1.

In some embodiments, the membrane transporter is P-glycoprotein. In some embodiments, the substrate of the membrane transporter is chosen from digoxin, loperamide, berberine, irinotecan, doxorubicin, vinblastine, paclitaxel, and fexofenadine.

In some embodiments, the membrane transporter is BCRP. In some embodiments, the substrate of the membrane transporter is chosen from mitoxantrone, methotrexate, topotecan, imatinib, irinotecan, statins, sulphate conjugates, and porphyrins.

In some embodiments, the membrane transporter is OATP1B1. In some embodiments, the substrate of the membrane transporter is chosen from bromosulphophthalein, oestrone-3-sulphate, oestradiol-17β-glucuronide, statins, repaglinide, valsartan, olmesartan, bilirubin glucuronide, bilirubin, and bile acids. In some embodiments, the substrate of the membrane transporter is rifampin.

In some embodiments, the membrane transporter is OATP1B3. In some embodiments, the substrate of the membrane transporter is rifampin.

In some embodiments, the dosage form is administered under fasted conditions. In some embodiments, the dosage form is administered under fed conditions.

In some embodiments, the method is non-gender specific.

In some embodiments, the individual is also being administered one or more agents independently chosen from oral corticosteroids and aminosalicylates.

In some embodiments, the individual is not being administered one or more agents independently chosen from natalizumab, efalizumab, and rituximab. In some embodiments, the administration of Compound 1 is not initiated if the individual is being administered one or more agents independently chosen from natalizumab, efalizumab, and rituximab. In some embodiments, the administration of Compound 1 is discontinued if the individual is being administered one or more agents independently chosen from natalizumab, efalizumab, and rituximab. In some embodiments, the dose of Compound 1 is reduced if the individual is being administered one or more agents independently chosen from natalizumab, efalizumab, and rituximab. In some embodiments, the individual has not been administered a biologic agent. In some embodiments, the individual has not been administered two or more biologic agents. In some embodiments, the individual has not been administered three or more biologic agents. In some embodiments, the individual is not being administered a biologic agent. In some embodiments, the individual is not being administered two or more biologic agents. In some embodiments, the individual is not being administered three or more biologic agents.

In some embodiments, the standard dose is administered without titration; and the individual does not experience a severe related adverse event.

In some embodiments, the therapeutically effective amount is equivalent to about 0.5 to about 5.0 mg of Compound 1 if the individual does not have an active infection. In some embodiments, Compound 1 is not administered to the individual 1 if the individual has an active infection. In some embodiments, the active infection is a serious active infection. In some embodiments, the method further comprises monitoring the individual for an active infection. In some embodiments, the method further comprises discontinuing administration if the individual develops an active infection.

In some embodiments, the method further comprises monitoring for adverse events during the administration of Compound 1, or a pharmaceutically acceptable salt, hydrate, or solvate thereof, and optionally, interrupting or terminating the administration of Compound 1, or a pharmaceutically acceptable salt, hydrate, or solvate thereof.

In some embodiments, the treatment further comprises monitoring heart rate during the administration, monitoring pulmonary function during the administration, or monitoring liver function during the administration.

In some embodiments, the treatment further comprises monitoring heart rate during the administration.

In some embodiments, the treatment further comprises monitoring pulmonary function during the administration.

In some embodiments, the treatment further comprises monitoring liver function during the administration.

In some embodiments, the method reduces the incidence and severity of adverse events resulting from the treatment of the sphingosine 1-phosphate subtype 1 (S1P$_1$) receptor-associated disorder.

In some embodiments, the adverse event is a serious adverse event.

In some embodiments, the serious adverse event is selected from leukopenia, constipation, diarrhea, nausea, abdominal pain, neutropenia, vomiting, back pain, and menstrual disorder.

In some embodiments, the method results in no serious adverse events.

In some embodiments, the standard dose is administered without substantially inducing an acute heart rate reduction or heart block in the individual.

In some embodiments, Compound 1 is administered without causing a reduction of more than 6 bpm in heart rate.

In some embodiments. Compound 1 is administered without a first-dose effect on heart rate as seen with other SIP receptor modulators. In some embodiments, Compound 1 is administered without a first-dose effect on AV conduction as seen with other SIP receptor modulators.

In some embodiments, the individual was previously administered at least one agent selected from: a TNF antagonist, an integrin antagonist, and an immunosuppressive agent.

In some embodiments, the individual had an inadequate response with, lost response to, or was intolerant to the at least one agent.

In some embodiments, the individual had demonstrated, over the previous 3-month period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 6-month period, an inadequate response to, loss of response to, or intolerance of at least one agent selected from oral 5-aminosalicylates, corticosteroids, immunosuppressives. TNFα antagonists, and integrin antagonists. In some embodiments, the individual had demonstrated, over the previous 9-month period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 1-year period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 2-year period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 3-year period, an inadequate response to, loss of response to, or intolerance of at least one agent selected from oral 5-aminosalicylates, corticosteroids, immunosuppressives. TNFα antagonists, and integrin antagonists. In some embodiments, the individual had demonstrated, over the previous 4-year period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 5-year period, an inadequate response to, loss of response to, or intolerance of at least one agent selected from oral 5-aminosalicylates, corticosteroids, immunosuppressives, TNFα antagonists, and integrin antagonists.

In some embodiments, the standard dose is administered without titration.

In some embodiments, the individual has fasted prior to being administered the standard dose In some embodiments, treating comprises inducing and/or maintaining clinical response; improving endoscopic appearance of the mucosa; and/or inducing and/or maintaining clinical remission.

In some embodiments, treating comprises inducing and/or maintaining histologic improvement.

In some embodiments, treating comprises inducing and/or maintaining histologic remission.

In some embodiments, treating comprises inducing and/or maintaining mucosal healing.

In some embodiments, prior to the administering the individual has a 3-component Mayo Clinic Score of at least 6.

In some embodiments, the method results in an improvement of the individual's 3-component Mayo Clinic Score. In some embodiments, the method results in an improvement of the individual's 2-component Mayo Clinic Score. In some embodiments, the method results in an improvement of the individual's Total Mayo Clinic Score.

In some embodiments of the method of treatment of inflammatory bowel disease, e.g., ulcerative colitis, such as moderately to severely active ulcerative colitis, the treatment results in endoscopic improvement, e.g., improving endoscopic appearance of the mucosa.

In some embodiments of the method of treatment of inflammatory bowel disease, e.g., ulcerative colitis, such as moderately to severely active ulcerative colitis, the treatment results in inducing clinical remission. In some embodiments of the method of treatment of inflammatory bowel disease, e.g., ulcerative colitis, such as moderately to severely active ulcerative colitis, the treatment results in maintaining clinical remission. In some embodiments of the method of treatment of inflammatory bowel disease, e.g., ulcerative colitis, such as moderately to severely active ulcerative colitis, the treatment results in inducing and maintaining clinical remission.

In some embodiments of the method of treatment of inflammatory bowel disease, e.g., ulcerative colitis, such as moderately to severely active ulcerative colitis, the treatment results in inducing clinical response. In some embodiments of the method of treatment of inflammatory bowel disease, e.g., ulcerative colitis, such as moderately to severely active ulcerative colitis, the treatment results in maintaining clinical response. In some embodiments of the method of treatment of inflammatory bowel disease, e.g., ulcerative colitis, such as moderately to severely active ulcerative colitis, the treatment results in inducing and maintaining clinical response.

In some embodiments, the treatment reduces a lymphocyte count in the individual by at least 40%. In some embodiments, the treatment reduces a lymphocyte count in the individual by at least 45%, 50%, 55%, 60%, or 65%.

In some embodiments of the method of treatment of inflammatory bowel disease, e.g., ulcerative colitis, such as moderately to severely active ulcerative colitis, the treatment results in corticosteroid-free remission.

In some embodiments of the method of treatment of inflammatory bowel disease, e.g., ulcerative colitis, such as moderately to severely active ulcerative colitis, the treatment results in endoscopic remission.

In some embodiments of the method of treatment of inflammatory bowel disease, e.g., ulcerative colitis, such as moderately to severely active ulcerative colitis, the treatment results in an improvement in rectal bleeding.

In some embodiments of the method of treatment of inflammatory bowel disease, e.g., ulcerative colitis, such as moderately to severely active ulcerative colitis, the treatment results in histologic healing.

In some embodiments of the method of treatment of inflammatory bowel disease, e.g., ulcerative colitis, such as moderately to severely active ulcerative colitis, the treatment results in an improvement in stool frequency.

In some embodiments of the method of treatment of inflammatory bowel disease, e.g., ulcerative colitis, such as moderately to severely active ulcerative colitis, the treatment further comprises monitoring the level of level of fecal calprotectin.

In some embodiments of the method of treatment of inflammatory bowel disease, e.g., ulcerative colitis, such as moderately to severely active ulcerative colitis, the treatment further comprises monitoring the level of level of c-reactive protein (CRP).

In some embodiments, treating is reducing a sign and/or symptom of ulcerative colitis. In some embodiments, treating is reducing a sign of ulcerative colitis. In some embodiments, treating is reducing a symptom of ulcerative colitis. In some embodiments, treating is reducing a sign and/or symptom of Crohn's disease. In some embodiments, treating is reducing a sign of Crohn's disease. In some embodiments, treating is reducing a symptom of Crohn's disease.

In some embodiments, treating is inducing and/or maintaining clinical remission. In some embodiments, treating is inducing and maintaining clinical remission. In some embodiments, treating is inducing and/or maintaining clinical remission and/or clinical response. In some embodiments, treating is inducing and maintaining clinical remission and clinical response. In some embodiments, treating is inducing clinical remission and/or clinical response. In some embodiments, treating is maintaining clinical remission and/or clinical response. In some embodiments, treating is inducing clinical remission and clinical response. In some embodiments, treating is maintaining clinical remission and clinical response. In some embodiments, treating is inducing and/or maintaining clinical remission and/or mucosal healing. In some embodiments, treating is inducing and maintaining clinical remission and mucosal healing. In some embodiments, treating is inducing and maintaining mucosal healing. In some embodiments, treating is inducing and maintaining clinical remission. In some embodiments, treating is inducing clinical remission. In some embodiments, treating is inducing mucosal healing. In some embodiments, treating is maintaining clinical remission. In some embodiments, treating is maintaining mucosal healing. In some embodiments, treating is achieving and/or sustaining clinical remission in induction responders. In some embodiments, treating is achieving and sustaining clinical remission in induction responders. In some embodiments, treating is achieving clinical remission in induction responders. In some embodiments, treating is sustaining clinical remission in induction responders. In some embodiments, treating is inducing and/or maintaining clinical response. In some embodiments, treating is inducing and maintaining clinical response. In some embodiments, treating is inducing clinical response. In some embodiments, treating is maintaining clinical response. In some embodiments, treating is inducing endoscopic improvement. In some embodiments, treating is maintaining endoscopic improvement. In some embodiments, treating is achieved endoscopic improvement. In some embodiments, treating is improving endoscopic remission. In some embodiments, treating is maintaining endoscopic remission. In some embodiments, treating is inducing histologic healing. In some embodiments, treating is maintaining histologic healing. In some embodiments, treating is improving stool frequency. In some embodiments, treating is maintaining improvement in stool frequency. In some embodiments, treating is improving endoscopic appearance of the mucosa. In some embodiments, treating is maintaining endoscopic improvement of the mucosa. In some embodiments, treating is improving endoscopic appearance of the mucosa during induction. In some embodiments, treating eliminates the need for corticosteroid use. In some embodiments, treating allows for reduced corticosteroid use. In some embodiments, treating allows for the use of a lower dose of a corticosteroid. In some embodiments, treating is achieving corticosteroid-free remission. In some embodiments, treating is sustaining corticosteroid-free remission. In some embodiments, treating is improving rectal bleeding. In some embodiments, treating is maintaining improvement in rectal bleeding. In some embodiments, treating is improving endoscopic subscore. In some embodiments, treating is maintaining improvement in endoscopic subscore.

In some embodiments, ulcerative colitis has been diagnosed using a 2-component Mayo Clinic Score. For example, in some embodiments, ulcerative colitis has been diagnosed using a score ranging from 0 to 9 for rectal bleeding and endoscopic findings. In some embodiments, ulcerative colitis has been diagnosed using a 3-component Mayo Clinic Score. For example, in some embodiments, ulcerative colitis has been diagnosed using a score ranging from 0 to 9 for stool frequency, rectal bleeding, and endoscopic findings. In some embodiments, ulcerative colitis has been diagnosed using a Total Mayo Score. For example, in some embodiments, ulcerative colitis has been diagnosed using a score ranging from 0 to 12 for stool frequency, rectal bleeding, endoscopic findings, and Physicians Global Assessment.

In some embodiments, improvement in ulcerative colitis is measured using a 2-component Mayo Clinic Score. In some embodiments, improvement in ulcerative colitis is measured using a 3-component Mayo Clinic Score. In some embodiments, improvement in ulcerative colitis is measured using a Total Mayo Score. In some embodiments, improvement in ulcerative colitis is measured by clinical remission. In some embodiments, improvement in ulcerative colitis is measured by lymphocyte reduction. In some embodiments, improvement in ulcerative colitis is measured by endoscopic improvement. In some embodiments, improvement in ulcerative colitis is measured by 6-point Mayo Score. For example, in some embodiments, improvement in ulcerative colitis is measured by stool frequency and rectal bleeding. In some embodiments, improvement in ulcerative colitis is statistically significant.

In some embodiments, Compound 1 is not recommended in an individual with active, severe infection. In some embodiments, Compound 1 is not recommended in an individual with an active infection. In some embodiments, Compound 1 is not recommended in an individual with a severe infection. In some embodiments, Compound 1 is not recommended in an individual with an active, severe infection until the infection is controlled. In some embodiments, Compound 1 is not recommended in an individual with an active infection until the infection is controlled. In some embodiments, Compound 1 is not recommended in an individual with a severe infection until the infection is controlled. In some embodiments, administration of Compound 1 is not started during an active infection. In some embodiments, an individual is monitored for infection. In some embodiments, administration of Compound 1 is stopped if an individual develops an infection. In some embodiments, administration of Compound 1 is stopped if infection becomes serious. In some embodiments, administration of Compound 1 is discontinued if an individual develops an infection. In some embodiments. Compound 1 is not administered to an individual with an infection. In some embodiments, Compound 1 is not administered during an active infection. In some embodiments, administration of Compound 1 is not started during active infection; an individual is monitored if an infection develops during administration; and administration is stopped if the infection becomes serious. In some embodiments, an infection is mild. In some embodiments, an infection is moderate. In some embodiments, an infection is severe. In some embodiments, an infection is serious. In some embodiments, an infection is a serious adverse event. In some embodiments, an infection is a respiratory infection.

In some embodiments, Compound 1 is administered without causing a severe adverse event. In some embodiments, Compound 1 is administered without causing a severe adverse event related to heart rate. In some embodiments, Compound 1 is administered without causing a severe adverse event related to heart rate change. In some embodiments, Compound 1 is administered without causing a severe adverse event related to elevated heart rate. In some embodiments, Compound 1 is administered without causing a severe adverse event related to bradycardia. In some embodiments, Compound 1 is administered without causing a severe adverse event related to AV block. In some embodiments, Compound 1 is administered without causing a severe adverse event related to AV conduction. In some embodiments, Compound 1 is administered without causing bradycardia. In some embodiments. Compound 1 is administered without causing AV block. In some embodiments, Compound 1 is administered without causing more than mild decrease in heart rate on first day of treatment (for example, >10 bpm). In some embodiments, Compound 1 is administered without a first-dose effect seen with other S1P receptor modulators. In some embodiments, Compound 1 is administered without a first-dose cardiovascular effect seen with other S1P receptor modulators. In some embodiments, Compound 1 is administered without symptomatic changes in heart rate. In some embodiments. Compound 1 is administered without symptomatic changes in heart rhythm. In some embodiments, Compound 1 is administered without requiring titration to avoid first-dose effect seen with other S1P receptor modulators.

In some embodiments, Compound 1 is administered without increasing a liver function test (LFT). In some embodiments. Compound 1 is administered without causing an elevated LFT. In some embodiments, Compound 1 is administered without increasing ALT. In some embodiments, Compound 1 is administered without increasing AST. In some embodiments, Compound 1 is administered without increasing ALT >3X ULN. In some embodiments, Compound 1 is administered without increasing ALT >2.5X ULN. In some embodiments, Compound 1 is administered without increasing ALT >2X ULN. In some embodiments, Compound 1 is administered without increasing ALT >1.5X ULN. In some embodiments, Compound 1 is administered without increasing AST >3X ULN. In some embodiments, Compound 1 is administered without increasing AST >2.5X ULN. In some embodiments, Compound 1 is administered without increasing AST >2X ULN. In some embodiments, Compound 1 is administered without increasing AST >1.5X ULN. In some embodiments. Compound 1 is administered without increasing bilirubin. In some embodiments, Compound 1 is administered without increasing bilirubin >3X ULN. In some embodiments, Compound 1 is administered without increasing bilirubin >2.5X ULN. In some embodiments, Compound 1 is administered without increasing bilirubin >2X ULN. In some embodiments, Compound 1 is administered without increasing bilirubin >1.5X ULN. In some embodiments, Compound 1 is administered without increasing gamma-glutamyl transferase (GGT). In some embodiments, Compound 1 is administered without increasing GGT >3X ULN. In some embodiments, Compound 1 is administered without increasing GGT >2.5X ULN. In some embodiments. Compound 1 is administered without increasing GGT >2X ULN. In some embodiments. Compound 1 is administered without increasing GGT >1.5X ULN.

In some embodiments, Compound 1 is administered without causing an abnormality in a pulmonary function test. In some embodiments, Compound 1 is administered without causing macular edema.

In some embodiments, the individual has had an inadequate response with, lost response to, been intolerant to, or demonstrated dependence on another agent for the treatment of an inflammatory bowel disease. In some embodiments, the individual has had an inadequate response with the other agent for the treatment of an inflammatory bowel disease. In some embodiments, the individual has lost response to another agent for the treatment of an inflammatory bowel disease. In some embodiments, the individual was intolerant to another agent for the treatment of an inflammatory bowel disease. In some embodiments, the individual requires continuous steroid therapy. In some embodiments, the other agent is at least one agent selected from: a tumor necrosis tumor necrosis factor (TNF) antagonist, a corticosteroid, an integrin antagonist, and immunosuppressive agent, and an aminosalicylate.

In some embodiments, the individual has had an inadequate response with, lost response to, or been intolerant to a conventional therapy. In some embodiments, the individual has had an inadequate response to conventional therapy. In some embodiments, the individual has lost response to conventional therapy. In some embodiments, the individual has been intolerant to conventional therapy. In some embodiments, the conventional therapy is selected from: at least one agent selected from: a tumor necrosis tumor necrosis factor (TNF) antagonist, a corticosteroid, an integrin antagonist, and immunosuppressive agent, and an aminosalicylate.

In some embodiments, the individual was previously administered a corticosteroid and/or an aminosalicylate. In some embodiments, the individual was previously administered a tumor necrosis tumor necrosis factor (TNF) antagonist, an integrin antagonist, and/or an immunosuppressive agent.

In some embodiments, the corticosteroid is an oral corticosteroid. In some embodiments, the TNF antagonist is a TNF-blocker. In some embodiments, the aminosalicylate is a 5-aminosalicylate. In some embodiments, the integrin antagonist is referred to as an integrin receptor antagonist. In some embodiments, the TNF antagonist is referred to as a TNF blocker. In some embodiments, the immunosuppressive agent is referred to as an immunomodulator. In some embodiments, the prior conventional therapy is referred to as prior treatment.

In some embodiments, the individual is not administered a therapeutic dose of a thiopurine. In some embodiments, the individual is not administered a therapeutic dose of azathioprine. In some embodiments, the individual is not administered a therapeutic dose of 6-mercaptopurine. In some embodiments, the individual is not administered a therapeutic dose of thioguanine (also referred to as tioguanine or 6-thioguanine).

In some embodiments, the inhibitor is a moderate inhibitor. In some embodiments, the inhibitor is a strong inhibitor. In some embodiments, the inducer is a moderate inducer. In some embodiments, the inducer is a strong inducer.

In some embodiments, caution is used when Compound 1 is co-administered with a CYP substrate. In some embodiments, caution is used when Compound 1 is co-administered with a UGT substrate. In some embodiments, caution is used when Compound 1 is co-administered with an OAT substrate. In some embodiments, caution is used when Compound 1 is co-administered with strong inhibitors. In some embodiments, the strong inhibitor is a strong CYP inhibitor. In some embodiments, the strong inhibitor is a CYP2C8. In some embodiments, caution is used when Compound 1 is co-administered with moderate inhibitors. In some embodiments, the moderate inhibitor is a moderate CYP inhibitor. In some embodiments, the moderate inhibitor is a CYP2C9 inhibitor. In some embodiments, caution is used when Compound 1 is co-administered with strong inducers. In some embodiments, the strong inhibitor is a strong CYP inducer. In some embodiments, caution is used when Compound 1 is co-administered with moderate inducers. In some embodiments, the moderate inducer is a moderate CYP inhibitor. In some embodiments, the moderate inducer is a CYP2C8 inducer. In some embodiments, the moderate inducer is a CYP2C9 inducer.

In some embodiments, the dose of Compound 1 is limited when used with a CYP substrate. In some embodiments, the dose of Compound 1 is limited when used a UGT substrate. In some embodiments, the dose of Compound 1 is limited when used with an OAT substrate. In some embodiments, the dose of Compound 1 is limited when used with strong inhibitors. In some embodiments, the dose of Compound 1 is limited to, or is limited to about, does not exceed, or does not exceed about, 0.25, 0.3, 0.4, 0.5, 0.6, 0.7, 0.75, 0.8, 0.9, 1.0, 1.1, 1.2, 1.3, 1.4, 1.5, 1.6, 1.7, 1.75, 1.8, 1.9, or 2.0 mg. In some embodiments, Compound 1 is administered at the lowest dose when used with a strong inhibitor. In some embodiments, the dose of Compound 1 is limited when used with moderate inhibitors. In some embodiments, Compound 1 is administered at the lowest dose when used with a moderate inhibitor. In some embodiments, the lowest dose is the lowest efficacious dose. In some embodiments, the lowest dose is the lowest marketed dose. In some embodiments, the lowest dose is the lowest marketed dose in the United States. In some embodiments, the lowest dose of Compound 1 is, or is about, 0.25, 0.3, 0.4, 0.5, 0.6, 0.7, 0.75, 0.8, 0.9, 1.0, 1.1, 1.2, 1.3, 1.4, 1.5, 1.6, 1.7, 1.75, 1.8, 1.9, or 2.0 mg.

In some embodiments, the dose of a co-administered compound is limited when used with Compound 1. In some embodiments, the co-administered compound is a CYP substrate. In some embodiments, the co-administered compound is a UGT substrate. In some embodiments, the dose of a co-administered compound is an OAT substrate. In some embodiments, the co-administered compound is a strong inducer. In some embodiments, the co-administered compound is a strong inhibitor. In some embodiments, the co-administered compound is a moderate inducer. In some embodiments, the co-administered compound is a moderate inhibitor. In some embodiments, the co-administered compound is administered at the lowest dose. In some embodiments, the lowest dose is the lowest efficacious dose. In some embodiments, the lowest dose is the lowest marketed dose. In some embodiments, the lowest dose is the lowest marketed dose in the United States.

In some embodiments. Compound 1 is not used with a CYP substrate. In some embodiments, Compound 1 is not used with a UGT substrate. In some embodiments. Compound 1 is not used with an OAT substrate. In some embodiments, Compound 1 is not used with strong inducers. In some embodiments, Compound 1 is not used with moderate inducers. In some embodiments, Compound 1 is not used with strong inhibitors. In some embodiments, Compound 1 is not used with moderate inhibitors.

In some embodiments, concomitant use of Compound 1 is not recommended with a CYP substrate. In some embodiments, concomitant use of Compound 1 is not recommended with a UGT substrate. In some embodiments, concomitant use of Compound 1 is not recommended with an OAT substrate. In some embodiments, concomitant use of Compound 1 is not recommended with strong inducers. In some embodiments, concomitant use of Compound 1 is not recommended with moderate inducers. In some embodiments, concomitant use of Compound 1 is not recommended with strong inhibitors. In some embodiments, concomitant use of Compound 1 is not recommended with moderate inhibitors. In some embodiments, concomitant use of Compound 1 is not recommended with a CYP2C8 inhibitor. In some embodiments, concomitant use of Compound 1 is not recommended with a CYP2C8 inducer. In some embodiments, concomitant use of Compound 1 is not recommended with a CYP2C9 inhibitor. In some embodiments, concomitant use of Compound 1 is not recommended with a CYP2C8 inducer.

Some embodiments provide a method of safely treating an individual with (R)-2-(7-(4-cyclopentyl-3-(trifluoromethyl) benzyloxy)-1,2,3,4-tetrahydrocyclopenta[b]indol-3-yl)acetic acid (Compound 1), or a pharmaceutically acceptable salt, hydrate, or solvate thereof.

Some embodiments provide a method of safely administering (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

Some embodiments provide a method of administering a daily dose of Compound 1 when an individual is concomitantly receiving a CYP substrate. OAT substrate, or UGT substrate. In some embodiments, the daily dose of Compound 1 is nor more than, or no more than about, 0.25, 0.3, 0.4, 0.5, 0.6, 0.7, 0.75, 0.8, 0.9, 1.0, 1.1, 1.2, 1.3, 1.4, 1.5, 1.6, 1.7, 1.75, 1.8, 1.9, 2.0, 2.1, 2.2, 2.25, 2.3, 2.4, 2.5, 2.6, 2.7, 2.75, 2.8, 2.9, or 3.0 mg. In some embodiments, the daily dose of Compound 1 is less than, or less than about. 0.25, 0.3, 0.4, 0.5, 0.6, 0.7, 0.75, 0.8, 0.9, 1.0, 1.1, 1.2, 1.3, 1.4, 1.5, 1.6, 1.7, 1.75, 1.8, 1.9, 2.0, 2.1, 2.2, 2.25, 2.3, 2.4, 2.5, 2.6, 2.7, 2.75, 2.8, 2.9, or 3.0 mg.

In some embodiments, the CYP substrate is a CYP2C8 substrate.

In some embodiments, the CYP substrate is a CYP2C9 substrate.

In some embodiments, the UGT substrate is a UGT1A1 substrate.

In some embodiments, the UGT substrate is a UGT1A4 substrate.

In some embodiments, the UGT substrate is a UGT1A6 substrate.

In some embodiments, the UGT substrate is a UGT1A7 substrate.

In some embodiments, the OAT substrate is an OATP1B1 substrate.

In some embodiments, the OAT substrate is an OATP1B3 substrate.

In some embodiments, the OAT substrate is an OAT1 substrate.

In some embodiments, the OAT substrate is an OAT3 substrate.

In some embodiments, the CYP2C8 inhibitor, CYP2C9 inhibitor, CYP2C8 inducer, or CYP2C9 inducer is fluconazole.

In some embodiments, the CYP2C8 inhibitor. CYP2C9 inhibitor, CYP2C8 inducer, or CYP2C9 inducer is gemfibrozil.

In some embodiments, the CYP2C8 inhibitor, CYP2C9 inhibitor, CYP2C8 inducer, or CYP2C9 inducer is rifampin.

In some embodiments, the substrate of OATP1B1 is rifampin.

In some embodiments, the substrate of OATP1B3 is rifampin.

In some embodiments, the co-administered compound is a CYP2C8 inhibitor.

In some embodiments, the co-administered compound is a CYP2C8 inducer.

In some embodiments, the co-administered compound is a CYP2C9 inhibitor.

In some embodiments, the co-administered compound is a CYP2C9 inducer.

In some embodiments, the co-administered compound is fluconazole.

In some embodiments, the co-administered compound is gemfibrozil.

In some embodiments, the co-administered compound is rifampin.

In some embodiments, less than the amount that would be administered to a patient who is not also being administered a CYP substrate, OAT substrate, UGT substrate, CYP2C8 inhibitor, CYP2C9 inhibitor, CYP2C8 inducer, CYP2C9 inducer, UGT1A1 inhibitor, or UGT1A6 inhibitor is about, at least, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90% less than the amount that would be administered to a patient who is not also being administered a CYP substrate, OAT substrate, UGT substrate, CYP2C8 inhibitor, CYP2C9 inhibitor. CYP2C8 inducer, CYP2C9 inducer, UGT1A1 inhibitor, or UGT1A6 inhibitor.

In some embodiments, less than the amount that would be administered to a patient who is not also being administered a CYP substrate, OAT substrate, UGT substrate, CYP2C8 inhibitor, CYP2C9 inhibitor, CYP2C8 inducer, CYP2C9 inducer, UGT1A1 inhibitor, or UGT1A6 inhibitor is about, at least, or at least about. 0.1, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, or 2.0 mg less than the amount that would be administered to a patient who is not also being administered a CYP substrate, OAT substrate, UGT substrate, CYP2C8 inhibitor, CYP2C9 inhibitor. CYP2C8 inducer, CYP2C9 inducer, UGT1A1 inhibitor, or UGT1A6 inhibitor.

Some embodiments provide a method of safely administering a sphingosine 1-phosphate subtype 1 ($S1P_1$) receptor modulator chosen from (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, to a patient in need thereof wherein the patient is also being administered a cytochrome P450 (CYP) inhibitor, CYP inducer, organic anion transporter (OAT) substrate. UDP-glucuronosyltransferase (UGT) enzyme inhibitor, or UDP-glucuronosyltransferase (UGT) enzyme inhibitor, comprising administering to the patient a daily dose of less than 2 mg of the $S1P_1$ modulator.

In some embodiments, the daily dose of the SIP; modulator is selected from: 1.0, 1.25, 1.5, and 1.75 mg of the $S1P_1$ modulator.

SIP receptor agonists having agonist activity on the $S1P_1$ receptor have been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007). This lymphocyte sequestration, for example in lymph nodes, is thought to be a consequence of concurrent agonist-driven functional antagonism of the SIP receptor on T-cells (whereby the ability of SIP to mobilize T-cell egress from lymph nodes is reduced) and persistent agonism of the $S1P_1$ receptor on lymph node endothelium (such that barrier function opposing transmigration of lymphocytes is increased) (Matloubian et al., *Nature*, 427:355-360, 2004; Baumruker et al., *Expert Opin. Investig. Drugs*, 16:283-289, 2007). It has been reported that agonism of the $S1P_1$ receptor alone is sufficient to achieve lymphocyte sequestration (Sanna et al., *J. Biol. Chem.*, 279:13839-13848, 2004) and that this occurs without impairment of immune responses to systemic infection (Brinkmann et al., *Transplantation*, 72:764-769, 2001; Brinkmann et al., *Transplant. Proc.*, 33:530-531, 2001).

That agonism of endothelial $S1P_1$ receptors has a broader role in promoting vascular integrity is supported by work implicating the $S1P_1$ receptor in capillary integrity in mouse skin and lung (Sanna et al., *Nat. Chem. Biol.*, 2:434-441, 2006). Vascular integrity can be compromised by inflammatory processes, for example as may derive from sepsis, major trauma and surgery so as to lead to acute lung injury or respiratory distress syndrome (Johan Groeneveld, *Vascul. Pharmacol.*, 39:247-256, 2003). An exemplary SIP receptor agonist having agonist activity on the $S1P_1$ receptor is FTY720 (fingolimod), an immunosuppressive agent that has undergone clinical trials (Martini et al., *Expert Opin. Investig. Drugs*, 16:505-518, 2007) and was recently approved by the FDA for the treatment of individuals with relapsing forms of multiple sclerosis (MS) to reduce the frequency of clinical exacerbations and to delay the accumulation of physical disability. FTY720 acts as a prodrug which is phosphorylated in vivo; the phosphorylated derivative is an agonist for $S1P_1$, $S1P_3$, $S1P_4$ and $S1P_5$ receptors (but not the $S1P_1$ receptor) (Chiba, *Pharmacology & Therapeutics*, 108: 308-319, 2005). FTY720 has been shown to rapidly and reversibly induce lymphopenia; Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007).

In clinical trials. FTY720 elicited an adverse event (i.e., transient asymptomatic bradycardia) which may be due to its agonism of the SIP; receptor (Budde et al., *J. Am. Soc. Nephrol.*, 13:1073-1083, 2002; Sanna et al., *J. Biol. Chem.*, 279: 13839-13848, 2004: Ogawa et al., *BBRC*, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007): a rat model for progressive mesangioproliferative glomerulonephritis (Martini et al., *Am. J. Physiol. Renal Physiol.*, 292:F1761-F1770, 2007); a mouse model for asthma, suggested to be primarily through the $S1P_1$ receptor on the basis of work using the $S1P_1$ receptor agonist SEW2871 (Idzko et al., *J. Clin. Invest.*, 116:2935-2944, 2006); a mouse model for airway inflammation and induction of bronchial hyperresponsiveness (Sawicka et al., *J. Immunol.*, 171:6206-6214, 2003); a mouse model for atopic dermatitis (Kohno et al., *Biol. Pharm. Bull.*, 27:1392-1396, 2004); a mouse model for ischemia-reperfusion injury (Kaudel et al., *Transplant. Proc.*, 39:499-502, 2007); a mouse model for systemic lupus erythematosus (SLE) (Okazaki et al., *J. Rheumatol.*, 29:707-716, 2002; Herzinger et al., *Am. J. Clin. Dermatol.*, 8:329-336, 2007); rat models for rheumatoid arthritis (Matsuura et al., *Int. J. Immunopharmacol.*, 22:323-331, 2000; Matsuura et al., *Inflamm. Res.*, 49:404-410, 2000); a rat model for autoimmune uveitis (Kurose et al., *Exp. Eye Res.*, 70:7-15, 2000); mouse models for type 1 diabetes (Fu et al., *Transplantation*, 73:1425-1430, 2002; Maki et al., *Transplantation*. 74:1684-1686, 2002; Yang et al., *Clinical Immunology*. 107:30-35, 2003; Maki et al., *Transplantation*, 79:1051-1055, 2005); mouse models for atherosclerosis (Nofer et al., *Circulation*, 115:501-508, 2007; Keul et al., *Arterioscler. Thromb. Vasc. Biol.*, 27:607-613, 2007); a rat model for brain inflammatory reaction following traumatic brain injury (TBI) (Zhang et al., *J. Cell. Mol. Med.*, 11:307-314, 2007); and mouse models for graft coronary artery disease and graft-versus-host disease (GVHD) (Hwang et al., *Circulation*, 100: 1322-1329, 1999; Taylor et al., *Blood*, 110:3480-3488, 2007). In vitro results suggest that FTY720 may have therapeutic efficacy for β-amyloid-related inflammatory diseases including Alzheimer's disease (Kaneider et al., *FASEB J.*, 18:309-311, 2004). KRP-203, an SIP receptor agonist having agonist activity on the $S1P_1$ receptor, has been reported to have therapeutic efficacy in a rat model for autoimmune myocarditis (Ogawa et al., *BBRC*. 361:621-628, 2007). Using the SIP; receptor agonist SEW2871, it has been shown that agonism of endothelial $S1P_1$ receptors prevents proinflammatory monocyte/endothelial interactions in type I diabetic vascular endothelium (Whetzel et al., *Circ. Res.*, 99:731-739, 2006) and protects the vasculature against TNFα-mediated monocyte/endothelial interactions (Bolick et al., *Arterioscler. Thromb. Vasc. Biol.*, 25:976-981, 2005).

Additionally. FTY720 has been reported to have therapeutic efficacy in experimental autoimmune encephalomyelitis (EAE) in rats and mice, a model for human multiple sclerosis (Brinkmann et al., *J. Biol. Chem.*, 277:21453-21457, 2002; Fujino et al., *J. Pharmacol. Exp. Ther.*, 305: 70-77, 2003; Webb et al., *J. Neuroimmunol.*, 153:108-121, 2004; Rausch et al., *J. Magn. Reson. Imaging*, 20:16-24, 2004; Kataoka et al., *Cellular & Molecular Immunology*, 2:439-448, 2005; Brinkmann et al., *Pharmacology & Therapeutics*, 115:84-105, 2007; Baumruker et al., *Expert Opin. Investig. Drugs*, 16:283-289, 2007; Balatoni et al., *Brain Research Bulletin*, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in individuals with multiple sclerosis (Kappos et al., *N. Engl. J. Med.*, 355:1124-1140, 2006; Martini et al., *Expert Opin. Investig. Drugs*. 16:505-518, 2007; Zhang et al., *Mini-Reviews in Medicinal Chemistry*. 7:845-850, 2007; Brinkmann, *Pharmacology & Therapeutics*, 115:84-105, 2007). Phase III clinical studies with FTY720 in individuals with remitting-relapsing multiple sclerosis have been reported (Brinkmann, *Pharmacology & Therapeutics*, 115:84-105, 2007; Baumruker et al., *Expert. Opin. Investig. Drugs*, 16:283-289, 2007; Dev et al., *Pharmacology and Therapeutics*, 117:77-93, 2008).

FTY720 has also been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., *Nature*, 454, 894, 2008).

FTY720 has been reported to impair migration of dendritic cells infected with *Francisella tularensis* to the mediastinal lymph node, thereby reducing the bacterial colonization of it. *Francisella tularensis* is associated with tularemia, ulceroglandular infection, respiratory infection and a typhoidal disease (E. Bar-Haim et al., PLOS Pathogens, 4(11): e1000211, published 21 Nov. 2008; info:doi/10.1371/journal.ppat. 1000211, 2008).

It has also been recently reported that a short-term high dose of FTY720 rapidly reduced ocular infiltrates in experimental autoimmune uveoretinitis. When given in the early stages of ocular inflammation. FTY720 rapidly prevented retinal damage. It was reported that FTY720 not only prevented infiltration of target organs, but also reduce existing infiltration (Raveney et al., *Arch. Ophthalmol.,* 126(10), 1390, 2008).

It has been reported that treatment with FTY720 relieved ovariectomy-induced osteoporosis in mice by reducing the number of mature osteoclasts attached to the bone surface. The data provided evidence that SIP controlled the migratory behavior of osteoclast precursors, dynamically regulating bone mineral homeostasis (Ishii et al., *Nature*, advance online publication, 8 Feb. 2009, doi: 10.1038/nature07713).

Agonism of the $S1P_1$ receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses (Miron et al., *Ann. Neurol.,* 63:61-71, 2008; Coelho et al., *J. Pharmacol. Exp. Ther.,* 323:626-635, 2007; Dev et al., *Pharmacology and Therapeutics,* 117:77-93, 2008). It also has been shown that the $S1P_1$ receptor plays a role in platelet-derived growth factor (PDGF)-induced oligodendrocyte progenitor cell mitogenesis (Jung et al., *Glia,* 55:1656-1667, 2007).

Agonism of the $S1P_1$ receptor has also been reported to mediate migration of neural stem cells toward injured areas of the central nervous system (CNS), including in a rat model of spinal cord injury (Kimura et al., *Stem Cells,* 25:115-124, 2007).

Agonism of the $S1P_1$ receptor has been implicated in the inhibition of keratinocyte proliferation (Sauer et al., *J. Biol. Chem.,* 279:38471-38479, 2004), consistent with reports that SIP inhibits keratinocyte proliferation (Kim et al., *Cell Signal,* 16:89-95, 2004). The hyperproliferation of keratinocytes at the entrance to the hair follicle, which can then become blocked, and an associated inflammation are significant pathogenetic factors of acne (Koreck et al., *Dermatology,* 206:96-105, 2003: Webster, *Cutis,* 76(2 Suppl):4-7, 2005).

FTY720 has been reported to have therapeutic efficacy in inhibiting pathologic angiogenesis, such as that as may occur in tumor development. Inhibition of angiogenesis by FTY720 is thought to involve agonism of the $S1P_1$ receptor (Oo et al., *J. Biol. Chem.,* 282:9082-9089, 2007; Schmid et al., *J. Cell Biochem.,* 101:259-270, 2007). FTY720 has been reported to have therapeutic efficacy for inhibiting primary and metastatic tumor growth in a mouse model of melanoma (LaMontagne et al., *Cancer Res.,* 66:221-231, 2006). FTY720 has been reported to have therapeutic efficacy in a mouse model for metastatic hepatocellular carcinoma (Lee et al., *Clin. Cancer Res.,* 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al., *J. Biol. Chem.,* 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, β-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506, and RAD (an mTOR inhibitor). It has been shown that, unlike the classical immunosuppressants cyclosporin A. FK506 and RAD, FTY720 has efficacy for prolonging graft survival without inducing general immunosuppression, and this difference in drug action is believed to be relevant to the synergism observed for the combination (Brinkmann et al., *Transplant Proc.,* 33:530-531, 2001; Brinkmann et al., *Transplantation,* 72:764-769, 2001).

Agonism of the $S1P_1$ receptor has been reported to have therapeutic efficacy for prolonging allograft survival in mouse and rat skin allograft models (Lima et al., *Transplant Proc.,* 36:1015-1017, 2004; Yan et al., *Bioorg. & Med. Chem. Lett.,* 16:3679-3683, 2006). FTY720 has been reported to have therapeutic efficacy for prolonging allograft survival in a rat cardiac allograft model (Suzuki et al., *Transpl. Immunol.,* 4:252-255, 1996). FTY720 has been reported to act synergistically with cyclosporin A to prolong rat skin allograft survival (Yanagawa et al., *J. Immunol.,* 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.,* 3:11-19, 2006). KRP-203, an SIP receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation,* 111:222-229, 2005). KRP-203 also has been reported to have therapeutic efficacy in combination with mycophenolate mofetil (MMF: a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant,* 25:302-209, 2006; Fujishiro et al., *J. Heart Lung Transplant,* 25:825-833, 2006). It has been reported that an agonist of the $SIP_1$ receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al., *Journal of Cellular and Molecular Medicine* 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., *J. Investigative Dermatology* (128(12). 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al., *Biological & Pharmaceutical Bulletin*, 28(4). 736-739, 2005).

In one embodiment, the present invention encompasses compounds which are agonists of the $S1P_1$ receptor having selectivity over the SIP; receptor. Using a combined chemical approach with SIP receptor null mice, Sanna et al. reported that sustained bradycardia was induced by nonselective SIP receptor immunosuppressive agonists in wild-type mice but was abolished in $S1P_3$-/- mice whereas an $S1P_1$-selective agonist did not produce bradycardia. Thus, suggesting that the SIP; receptor, and not the $S1P_1$ receptor, was responsible for bradycardia (Sanna et al., *J. Biol. Chem.*, 279:13839-13848, 2004). Therefore, an $S1P_1$ receptor agonist selective over at least the SIP; receptor has advantages over current therapies by virtue of an enhanced therapeutic window, allowing better tolerability with higher dosing and thus improving efficacy as therapy. The present invention encompasses Compound 1 (and pharmaceutically acceptable salts, hydrates, and solvates thereof) which is an agonist of the $S1P_1$ receptor and has exhibited no or substantially no bradycardia in male Sprague-Dawley® rats (see WO2010/011316. Example 9).

A phase 1 study with Compound 1 was conducted with single dosing at 0.1 mg, 0.35 mg, 1 mg, 3 mg, and 5 mg. Compound 1 was administered as the L-arginine salt. Lower doses of 0.1 mg through 3 mg were well tolerated by subjects with only minor adverse events reported, the most common of which were headache and contact dermatitis. A dose-dependent reduction in heart rate was seen in all doses >0.35 mg, however, no adverse events related to bradycardia were reported at doses lower than the 5 mg dose. Dose limiting adverse events were observed at the dose of 5 mg, with 3 (50%) subjects experiencing 4 AEs of bradycardia with first or second degree atrioventricular (AV) block, which resulted in discontinuation of dose escalation. The maximum tolerated dose in the study was 3 mg. There were no deaths or serious adverse events in the study.

There were no other clinically significant safety issues with respect to vital signs, ECGs, pulmonary function tests, ophthalmoscopy, or clinical laboratory tests with the exception of expected pharmacological effects on peripheral blood lymphocyte counts. Dosing at the 3 and 5 mg induced a dose responsive decline in the absolute number of peripheral blood B cells. T cells, NK cells, and all T cell subsets except TEM cells. Total peripheral blood lymphocyte (PBL) counts were reduced by 2-4 hours after dosing, reaching a nadir by hour & which persisted for 24 hours with recovery to baseline over the next 4 days. PBL counts were reduced by ~40% and ~55% at the 3 mg and 5 mg dose levels. TEM cells do not express CCR7 and are able to recirculate independently of SIP receptor expression. These findings are therefore consistent with the anticipated pharmacodynamic effects of SIP receptor agonists in preclinical studies and in humans (Gergely et al., *Br J Pharmacol* 167(5): 1035-1047, 2012; Brossard et al., *Br J Clin Pharmacol* 2013 Apr. 18. doi: 10.1111/bcp. 12129. [Epub ahead of print] PubMed PMID: 23594176, and Kovarik et al., *J Clin Pharmacol* 44(5):532-537, 2004.)

$S1P_1$ receptor agonists are useful to treat or prevent conditions where suppression of the immune system or agonism of the $S1P_1$ receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In one embodiment, the present invention encompasses compounds which are agonists of the $S1P_1$ receptor having good overall physical properties and biological activities and having an effectiveness that is substantially at least that of prior compounds with activity at the $S1P_1$ receptor.

$S1P_1$ receptor agonists are useful for treating or preventing conditions where suppression of the immune system or agonism of the $S1P_1$ receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the $S1P_1$ receptor is in order include diseases and disorders mediated by lymphocytes; conditions that have an underlying defect in vascular integrity; autoimmune diseases and disorders; inflammatory diseases and disorders (e.g., acute and chronic inflammatory conditions); acute or chronic rejection of cells; tissue or solid organ grafts; arthritis, including psoriatic arthritis, and rheumatoid arthritis; diabetes, including type I diabetes; demyelinating disease, including multiple sclerosis; ischemia-reperfusion injury, including renal and cardiac ischemia-reperfusion injury; inflammatory skin disease, including psoriasis, atopic dermatitis, and acne; hyperproliferative skin disease, including acne; inflammatory bowel disease, including Crohn's disease, and ulcerative colitis; systemic lupus erythematosus; asthma; uveitis; myocarditis; allergy; atherosclerosis; brain inflammation, including Alzheimer's disease, and brain inflammatory reaction following traumatic brain injury; ankylosing spondylitis; central nervous system disease, including spinal cord injury, or cerebral infarction; pathologic angiogenesis, including as may occur in primary and metastatic tumor growth; rheumatoid arthritis; diabetic retinopathy, atherosclerosis; cancer; chronic pulmonary disease; acute lung injury; acute respiratory disease syndrome; sepsis; and the like. In addition, $S1P_1$ receptor agonists are useful for treating microbial infections, and viral infections or diseases.

In some embodiments, the sphingosine 1-phosphate subtype 1 (S1P$_1$) receptor-associated disorder is selected from: a disease or disorder mediated by lymphocytes, an autoimmune disease or disorder, an inflammatory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury and acne.

In some embodiments, the S1P$_1$ receptor-associated disorder is a disease or disorder mediated by lymphocytes.

In some embodiments, the S1P$_1$ receptor-associated disorder is an autoimmune disease or disorder.

In some embodiments, the S1P$_1$ receptor-associated disorder is an inflammatory disease or disorder.

In some embodiments, the S1P$_1$ receptor-associated disorder is ankylosing spondylitis.

In some embodiments, the S1P$_1$ receptor-associated disorder is biliary cirrhosis.

In some embodiments, the S1P$_1$ receptor-associated disorder is primary biliary cholangitis.

In some embodiments, the S1P$_1$ receptor-associated disorder is cancer.

In some embodiments, the S1P$_1$ receptor-associated disorder is psoriasis.

In some embodiments, the S1P$_1$ receptor-associated disorder is erythema nodosum.

In some embodiments, the S1P$_1$ receptor-associated disorder is pyoderma gangrenosum.

In some embodiments, the S1P$_1$ receptor-associated disorder is psoriatic arthritis.

In some embodiments, the S1P$_1$ receptor-associated disorder is rheumatoid arthritis.

In some embodiments, the S1P$_1$ receptor-associated disorder is Crohn's disease.

In some embodiments, the S1P$_1$ receptor-associated disorder is transplant rejection.

In some embodiments, the S1P$_1$ receptor-associated disorder is multiple sclerosis.

In some embodiments, the S1P$_1$ receptor-associated disorder is systemic lupus erythematosus.

In some embodiments, the SIP; receptor-associated disorder is inflammatory bowel disease (IBD).

In some embodiments, the S1P$_1$ receptor-associated disorder is an active skin extra-intestinal manifestation of inflammatory bowel disease. In some embodiments, the S1P$_1$ receptor-associated disorder is an active skin extra-intestinal manifestation of ulcerative colitis. In some embodiments, the active skin extra-intestinal manifestation is psoriasis. In some embodiments, the active skin extra-intestinal manifestation is erythema nodosum. In some embodiments, the active skin extra-intestinal manifestation is pyoderma gangrenosum.

In some embodiments, the S1P$_1$ receptor-associated disorder is ulcerative colitis. In some embodiments, the S1P$_1$ receptor-associated disorder is moderately to severely active ulcerative colitis. In some embodiments, the S1P$_1$ receptor-associated disorder is moderately active ulcerative colitis. In some embodiments, the S1P$_1$ receptor-associated disorder is severely active ulcerative colitis. In some embodiments, the S1P$_1$ receptor-associated disorder is mildly to moderately active ulcerative colitis. In some embodiments, the S1P$_1$ receptor-associated disorder is mildly active ulcerative colitis.

In some embodiments, the S1P$_1$ receptor-associated disorder is type I diabetes.

In some embodiments, the SIP; receptor-associated disorder is hypertensive nephropathy.

In some embodiments, the S1P$_1$ receptor-associated disorder is glomerulosclerosis.

In some embodiments, the S1P$_1$ receptor-associated disorder is myocardial ischemia-reperfusion injury.

In some embodiments, the S1P$_1$ receptor-associated disorder is acne.

In some embodiments, the S1P$_1$ receptor-associated disorder is autoimmune hepatitis.

In some embodiments, the standard dose is in an amount equivalent to 1 mg of Compound 1.

In some embodiments, the standard dose is in an amount equivalent to 2 mg of Compound 1.

In some embodiments, the standard dose is in an amount equivalent to 3 mg of Compound 1.

In some embodiments, the standard dose of Compound 1, or a pharmaceutically acceptable salt, hydrate, or solvate thereof is administered once daily to the individual.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the Compound 1, or a pharmaceutically acceptable salt, hydrate, or solvate thereof, is selected from: Compound 1; a calcium salt of Compound 1; and an L-arginine salt of Compound 1. In some embodiments, the Compound 1, or a pharmaceutically acceptable salt, hydrate, or solvate thereof, is an L-arginine salt of Compound 1. In some embodiments, the Compound 1, or a pharmaceutically acceptable salt, hydrate, or solvate thereof, is an anhydrous, non-solvated crystalline form of an L-arginine salt of Compound 1. In some embodiments, the Compound 1, or a pharmaceutically acceptable salt, hydrate, or solvate thereof, is an anhydrous, non-solvated crystalline form of Compound 1.

In some embodiments, the individual also is administered a therapeutic dose of an oral 5-ASA compound. In some embodiments, the individual also is administered a stable dose of an oral 5-ASA compound.

In some embodiments, the individual also is administered a therapeutic dose of an oral corticosteroid therapy. In some embodiments, the individual also is administered a stable dose of an oral corticosteroid therapy. In some embodiments, the corticosteroid is prednisone, e.g., prednisone at a dose ≤10 mg/day or 20 mg/day, or an equivalent steroid. In some embodiments, the corticosteroid is budesonide, e.g., at a dose ≤9 mg/day, or an equivalent steroid.

In some embodiments, the individual also is administered a therapeutic dose of an immunosuppressive agent. In some embodiments, the individual also is administered a therapeutic dose of a thiopurine. In some embodiments, the individual also is administered a therapeutic dose of azathioprine. In some embodiments, the individual also is administered a therapeutic dose of 6-mercaptopurine. In some embodiments, the individual also is administered a therapeutic dose of thioguanine (also referred to as tioguanine or 6-thioguanine).

In some embodiments, the individual also is administered a therapeutic dose of a probiotic. In some embodiments, the individual also is administered a therapeutic dose of Culturelle. In some embodiments, the individual also is administered a therapeutic dose of *Saccharomyces boulardii*.

In some embodiments, the individual also is administered a therapeutic dose of an antidiarrheal. In some embodiments, the individual also is administered a therapeutic dose of loperamide. In some embodiments, the individual also is administered a therapeutic dose of diphenoxylate with atropine.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

Also provided are pharmaceutical compositions comprising a standard dose of Compound 1, or, a pharmaceutically acceptable salt, a hydrate or solvate thereof and, optionally, one or more pharmaceutically acceptable carriers. Also provided are pharmaceutical compositions comprising Compound 1, or, a pharmaceutically acceptable salt, a hydrate or solvate thereof, optionally, one or more pharmaceutically acceptable carriers. The carrier(s) must be "acceptable" in the sense of being compatible with the other ingredients of the formulation and not overly deleterious to the recipient thereof.

In some embodiments, Compound 1, or, a pharmaceutically acceptable salt, a hydrate or solvate thereof, is administered as a raw or pure chemical, for example as a powder in capsule formulation.

In some embodiments, Compound 1, or, a pharmaceutically acceptable salt, a hydrate or solvate thereof, is formulated as a pharmaceutical composition further comprising one or more pharmaceutically acceptable carriers.

Pharmaceutical compositions may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. The compounds described herein can be formulated into pharmaceutical compositions using techniques well known to those in the art. Suitable pharmaceutically acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

For oral administration, the pharmaceutical composition may be in the form of, for example, a tablet or capsule. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like. The term "preparation" includes the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets or capsules. Also, the unit dosage form can be a capsule or tablet itself, or it can be the appropriate number of any of these in packaged form.

Further embodiments include the embodiments disclosed in the following Examples, which is not to be construed as limiting in any way.

EXAMPLES

Example 1

Formulations composed of immediate-release, hard gelatin capsules containing an L-arginine salt of Compound 1 were prepared as shown in Table 1.

TABLE 1

| | Formulation | | | | |
|---|---|---|---|---|---|
| | 0.1 mg | 0.35 mg | 0.5 mg | 1 mg | 2 mg |
| L-arginine salt of Compound 1 (mg/capsule) | 0.14 | 0.48 | 0.69 | 1.38 | 2.76 |
| Empty capsule weight (mg)* | 38.0 | 61.0 | 61.0 | 61.0 | 61.0 |
| Total capsule target weight (mg)** | 38.14 | 61.48 | 61.69 | 62.38 | 63.76 |

*Approximate weight. Based on capsule specification
**Theoretical total weight calculated by combining fill and empty capsule weights together Example 2

Formulations composed of immediate-release tablets containing an L-arginine salt of Compound 1 were prepared as shown in Table 2.

TABLE 2

| | Tablet Strength | | | |
|---|---|---|---|---|
| | 0.5 mg | 1 mg | 2 mg | 3 mg |
| L-Arg Salt of Compound 1 | 0.69 | 1.381 | 2.762 | 4.143 |
| Mannitol Pearlitol® 100 SD | 54.81 | 54.119 | 52.738 | 51.357 |
| Microcrystalline cellulose - Avicel® | 40 | 40 | 40 | 40 |
| Sodium Starch Glycolate - Explotab® | 4 | 4 | 4 | 4 |
| Magnesium Stearate | 0.5 | 0.5 | 0.5 | 0.5 |
| Opadry® II Blue | 4 | 4 | 4 | 4 |
| Total tablet target weight | 104 | 104 | 104 | 104 |

Example 3

In Vitro Evaluation of Compound 1 as an Inhibitor of Cytochrome P450 (CYP) and UDP-Glucuronosyltransferase (UGT) Enzymes in Human Liver Microsomes Compound 1 was evaluated for potential inhibition of the cytochrome P450 (CYP) enzymes CYP1A2, CYP2B6, CYP2C8, CYP2C9, CYP2C19, CYP2D6, CYP3A4/5 (using two different marker substrates) and UDP-glucuronosyltransferase (UGT) enzymes UGT1A1, UGT1A3, UGT1A4, UGT1A6, UGT1A9, UGT2B7 and UGT2B17 in human liver microsomes, with the aim of ascertaining the potential of Compound 1 to inhibit the metabolism of concomitantly administered drugs.

To evaluate Compound 1 as a direct and metabolism-dependent inhibitor of CYP activity and as a direct inhibitor of UGT activity, human liver microsomes from a pool of 200 individuals were incubated with marker substrates in the presence or absence of Compound 1 at concentrations of 0, 1 or 10 µM. For metabolism-dependent inhibition of CYP enzymes, Compound 1 was preincubated with human liver microsomes for 30 minutes with an NADPH-regenerating system, prior to the incubation with the marker substrates. Known metabolism-dependent and/or direct inhibitors of CYP and UGT enzymes were included as positive controls, as applicable.

After 120 minutes of incubation with rCYP enzymes. Compound 1 loss was observed to the greatest extent with rCYP2C8 (up to 75%) and ranged from 12 to 36% loss with rCYP2C9, rCYP2C19 and rCYP3A4. In the HLMs without chemical inhibitors, overall loss of Compound 1 was negligible (0 to 13.0%). A selective CYP2C8 inhibitor (gemfibrozil) inhibited, by 85%, 47%, and 60%, the limited conversion of Compound 1 to two oxidative metabolites and a ketone metabolite, respectively. The limited conversion of Compound 1 to the second oxidative metabolite was also inhibited (72%) by a CYP2C9 inhibitor (tienilic acid).

Direct inhibition of CYP2C8 activity was 22% at 1 µM and ~100% at 10 µM in the presence of Compound 1. Little or no direct inhibition of CYP1A2, CYP2B6, CYP2C9, CYP2C19, CYP2D6 or CYP3A4/5 activities was observed in the presence of Compound 1 concentrations up to 10 µM. In addition, little or no evidence of metabolism-dependent inhibition of CYPs was seen.

Treatment of cultured human hepatocytes with Compound 1 was found to have no induction potential on CYP1A2 mRNA. Additionally, no induction potential for CYP2B6 and CYP3A4 was seen, based on induction criteria being a >2-fold increase in mRNA and ≥20% of the mRNA increase seen with positive control.

Compound 1 directly inhibited UGT1A1 and UGT1A6 activities by up to 28% and 48%, respectively, at the highest concentration tested (10 µM). There was no evidence of direct inhibition of UGT1A3. UGT1A4, UGT1A9, UGT2B7 or UGT2B17 as less than 8% inhibition was observed in the presence of Compound 1 concentrations up to 10 µM.

Based on the results from two approaches to CYP reaction phenotyping, CYP2C8 and CYP2C9 were established to play major roles in conversion of Compound 1 to oxidative metabolites, and CYP2C8 also plays a major role in formation of a ketone metabolite. However, the overall conversion of Compound 1 to metabolites was negligible in HLMs and there was little difference in the loss of Compound 1 seen in the presence and absence of direct-acting and metabolism-dependent selective CYP inhibitors. Direct inhibition of CYP2C8 activity was 22% at 1 µM and ~100% at 10 µM in the presence of Compound 1. However, there was little or no direct inhibition observed for any other CYPs with Compound 1. Compound 1 directly inhibited UGT1A1 and UGT1A6 activities by up to 28% and 48%, respectively, at the highest concentration tested (10 µM), but there was no evidence of direct inhibition of UGT1A3, UGT1A4, UGT1A9, UGT2B7 or UGT2B17. Compound 1 (up to 10 µM) was not a potential inducer of CYP1A2, CYP2B6, and CYP3A4/5.

Example 4

Compound 1 was evaluated as a potential substrate and/or inhibitor of human ABC transporters P-gp. BCRP and BSEP or human SLC transporters OATP1B1, OATP1B3, OAT1, OAT3, OCT1, OCT2, MATE1 and MATE2-K. P-gp and BCRP are expressed on the apical membrane of a number of tissues. P-gp and BCRP are expressed in the luminal membrane of enterocytes, endothelial cells in the brain, the brush border membrane of renal proximal tubules and the canalicular membrane of hepatocytes where they limit the intestinal absorption, blood-brain barrier penetration and facilitate excretion into the bile and urine. BSEP is mainly expressed in the canalicular membrane of hepatocytes where it facilitates excretion into the bile. OATP1B1, OATP1B3 and OCT1 are expressed on the sinusoidal membrane of hepatocytes and facilitate the accumulation of endogenous and xenobiotic compounds into hepatocytes for further metabolism or excretion into the bile. OAT1, OAT3 and OCT2 are expressed on the basolateral membrane of renal proximal tubules and facilitate the accumulation of compounds into the proximal tubule for further excretion into the urine. MATE1 and MATE2-K (multidrug and toxin extrusion proteins) are primarily expressed on the luminal (apical) membrane of the proximal tubular cells and thought to play a role in the excretion of cations and zwitterions into urine. MATE1 is also expressed in the liver on the canalicular membrane of hepatocytes and mediates the biliary excretion of cationic drugs. MATE1 and MATE2-K may function in cooperation with OCT transporters expressed on the canalicular membranes of hepatocytes and the basolateral membranes of proximal tubules to mediate excretion. Compounds that are substrates or inhibitors of the transporters may be victims or perpetrators in drug-drug interactions.

Madin-Darby canine kidney cells (MDCKII), over-expressing human permeability-glycoprotein (P-gp) and breast cancer resistance protein (BCRP), were used to evaluate Compound 1 as a substrate of P-gp and BCRP, and as an inhibitor of BCRP. A polarized cell line, derived from a human colon carcinoma (Caco 2) cells, was used to evaluate Compound 1 as an inhibitor of P-gp. Membrane vesicles expressing bile salt export pump (BSEP) were used in a vesicular transport assay to evaluate Compound 1 as an inhibitor of BSEP. Human embryonic kidney cells (HEK293) transfected with vectors containing human transporter cDNA for organic anion-transporting polypeptide 1B1 (OATP1B1), organic anion-transporting polypeptide 1B3 (OATP1B3), organic anion transporter 1 (OAT1), organic anion transporter 3 (OAT3), organic cation transporter 1 (OCT1), organic cation transporter 2 (OCT2) and control cells (HEK293 cells transfected with only vector) were used in experiments to evaluate Compound 1 as a substrate and an inhibitor of OATP1B1, OATP1B3, OAT1, OAT3, OCT1 and OCT2. HEK293 cells transfected with vectors containing renal multidrug and toxin extrusion transporters 1 and 2-K (MATE1, MATE2-K) were used for evaluating Compound 1 as an inhibitor of MATE1 and MATE2-K. Known substrates and inhibitors of ABC and SLC transporters were included as positive controls in all experiments.

There was no P-gp inhibition at 10 µM. In the presence of 100 µM Compound 1, the efflux ratio of digoxin (10 µM) across Caco-2 cells was reduced by ~50% indicating that Compound 1 is an inhibitor of P-gp with an IC50 value of ~100 µM.

In the presence of Compound 1 (10 and 100 µM), the corrected efflux ratio of prazosin (1 µM) across MDCKII-BCRP cells was reduced by more than 50%; however, inhibition potential of Compound 1 could not be determined since post-assay TEER values were below acceptance criteria and lucifer yellow Papp values were above acceptable ranges at both 10 and 100 µM. To determine an IC50, a second experiment was performed with seven concentrations of Compound 1 ranging from 0.03 to 30 µM. The resulting IC50 value was 35.7 µM.

In the presence of Compound 1 (1 and 10 µM), the ATP-dependent uptake of [3H]-taurocholic acid in BSEP-expressing vesicles was reduced by less than 50% indicating that Compound 1 is not an inhibitor of BSEP at the concentrations evaluated.

There was no OATP1B1 inhibition at 1 µM Compound 1. In the presence of 10 µM Compound 1, the uptake rate of [3H]-estradiol-17β-glucuronide (50 nM) into OATP1B1-expressing cells was reduced by ~50% indicating Compound 1 is an inhibitor of OATP1B1 with an IC50 value of ~10 µM.

In the presence of Compound 1 (1 and 10 µM), the uptake rate of [3H]-estradiol-17β-glucuronide (50 nM) into OATP1B3-expressing cells was reduced by less than 50% indicating Compound 1 is not an inhibitor of OATP1B3 at the concentrations evaluated (IC50>10 µM).

In the presence of Compound 1 (1 and 10 µM), the uptake rate of [3H]-p-aminohippurate (1 µM) into OAT1-expressing cells was reduced by less than 50% indicating Compound 1 is not an inhibitor of OAT1 at the concentrations evaluated (IC50>10 µM).

In the presence of Compound 1 (1 and 10 µM), the uptake rate of [3H]-estrone-3-sulfate (50 nM) into OAT3-expressing cells was reduced by less than 50% indicating Compound 1 is not an inhibitor at the concentrations evaluated (IC50>10 µM).

In the presence of Compound 1 (1 and 10 µM), the uptake rate of [14C]-tetraethylammonium bromide (5 µM) into OCT1-expressing cells was reduced by less than 50% indicating Compound 1 is not an inhibitor at the concentrations evaluated (IC50>10 µM).

In the presence of Compound 1 (1 and 10 µM), the uptake rate of [14C]-metformin (10 µM) into OCT2-expressing cells was not reduced indicating Compound 1 is not an inhibitor of OCT2 at the concentrations evaluated (IC50>10 µM).

The efflux ratio of Compound 1 (1 µM) across MDCKII-P-gp cells was 1.12 and increased to 3.08 in the presence of the P-gp inhibitor valspodar (10 µM). The efflux ratio of Compound 1 (10 µM) across MDCKII-P-gp cells was 3.17 and did not reduce in the presence of valspodar. These results indicate Compound 1 is not a substrate of P-gp since the efflux ratio of Compound 1 was not reduced in the presence of inhibitor. It should be noted that Compound 1 recovery was low ranging from 18 to 60% and is likely due to non-specific binding to the plate.

The efflux ratio of Compound 1 across MDCKII-BCRP cells was less than two at 1 µM, and more than two at 10 µM in the absence and presence of the BCRP inhibitor Ko143 (1 µM). Although the efflux ratio of Compound 1 at 10 µM was 7.36 and was reduced to 3.17 in the presence of Ko143 (1 µM), the efflux ratio data of Compound 1 at 1 µM indicate Compound 1 is not a substrate of BCRP. For consideration as a substrate of the BCRP transporter, the efflux ratio of Compound 1 would be appreciably higher at lower concentration (1 µM) than at higher concentration (10 µM), and the consequent inhibition effect would likely be higher at a lower concentration (1 µM). It should be noted that Compound 1 recovery was low ranging from 27 to 48% and is likely due to non-specific binding to the plate.

The uptake ratio of Compound 1 (1 and 10 µM) into OATP1B1-expressing cells was less than two in the absence and presence of the OATP1B1 inhibitor rifampin. These results show that Compound 1 is not a substrate of OATP1B1.

The uptake ratio of Compound 1 (1 and 10 µM) into OATP1B3-expressing cells was less than two in the absence and presence of the OATP1B3 inhibitor rifampin. These results show that Compound 1 is not a substrate of OATP1B3.

The uptake ratio of Compound 1 (1 and 10 µM) into OAT1-expressing cells was less than two in the absence and presence of the OAT1 inhibitor probenecid (100 µM). These results show that Compound 1 is not a substrate of OAT1.

The uptake ratio of Compound 1 (1 and 10 µM) into OAT3-expressing cells was below two in the absence and presence of the OAT3 inhibitor probenecid (100 µM). These results show that Compound 1 is not a substrate of OAT3.

The uptake ratio of Compound 1 (1 and 10 µM) into OCT1-expressing cells was below two in the absence and presence of the OCT1 inhibitor quinidine (100 µM). These results show that Compound 1 is not a substrate of OCT1.

The uptake ratio of Compound 1 (1 and 10 µM) into OCT2-expressing cells was below two in the absence and presence of the OCT2 inhibitor quinidine (300 µM). These results show that Compound 1 is not a substrate of OCT2.

TABLE 3

In Vitro Characterization of Compound 1 as a Potential Substrate for Human ABC and SLC Transporters

| Transporter | Test system | Compound 1 concentrations | Potential substrate (uptake or efflux ratio ≥2 and reduced in presence of inhibitor) |
|---|---|---|---|
| P-gp | MDCKII-P-gp cells | 1 and 10 µM | No |
| BCRP | MDCKII-BCRP cells | | No |
| OATP1B1 | HEK293 cells | | No |
| OATP1B3 | | | No |
| OAT1 | | | No |
| OAT3 | | | No |
| OCT1 | | | No |
| OCT2 | | | No |

TABLE 4

In Vitro Characterization of Compound 1 as a
Potential Inhibitor of Human ABC and SLC Transporters

| Transporter | Test system | Substrate | Compound 1 concentrations | $IC_{50}$ (μM) |
|---|---|---|---|---|
| P-gp | Caco-2 cells | Digoxin (10 μM) | 10 and 100 μM | ~100[a] |
| BCRP | MDCKII-BCRP cells | Prazosin (1 μM) | 0.03 to 30 μM | 35.7 |
| BSEP | Vesicles | [$^3$H]-Taurocholic acid (0.4 μM) | 1 and 10 μM | >10[a] |
| OATP1B1 | HEK293 cells | [$^3$H]-Estradiol-17β-glucuronide | | ~10[a] |
| OATP1B3 | | (50 nM) | | >10[a] |
| OAT1 | | [$^3$H]-p-Aminohippurate (1 μM) | | >10[a] |
| OAT3 | | [$^3$H]-Estrone-3-sulfate (50 nM) | | >10[a] |
| OCT1 | | [$^{14}$C]-Tetraethylammonium bromide (5 μM) | | >10[a] |
| OCT2 | | [$^{14}$C]-Metformin (10 uM) | | >10[a] |
| MATE1 | | | | >10[a] |
| MATE2-K | | | | >10[a] |

[a]Two test article concentrations were evaluated and <50% inhibition was observed Overall, the results of this study showed the following:

Compound 1 was not a substrate of P-gp, BCRP, OATP1B1, OATP1B3, OAT1, OAT3, OCT1 and OCT2 transporters under the conditions evaluated. Compound 1 inhibited P-gp, BCRP and OATP1B1 with $IC_{50}$ values of ~100, 35.7, and ~10 μM, respectively. Compound 1 (up to 10 M) caused less than 50% inhibition of all the other transporters examined (BSEP, OATP1B3, OAT1, OAT3, OCT1, OCT2, MATE1 and MATE2-K).

Compound 1 inhibited P-gp, BCRP and OATP1B1 with an IC50 values of ~100, 35.7 and ~10 μM, respectively.

Compound 1 (up to 10 μM) caused less than 50% inhibition of the other transporters examined (BSEP, OATP1B3, OAT1, OAT3, OCT1, OCT2, MATE1 and MATE2-K). Compound 1 was found to have no inhibition potential with an IC50>10 μM on BSEP, OATP1B3, OAT1, OAT3, OCT1, OCT2, MATE1 and MATE2-K transporters.

Example 5

Compound 1 was evaluated to assess the single dose relative oral bioavailability of 2 mg tablet and capsule formulations in the fasted state, determine the effect of food on the pharmacokinetics of the 2 mg tablet, assess potential gender differences in Compound 1 pharmacokinetics, and evaluate safety and tolerability in healthy adult subjects.

A randomized, single-dose, open-label, three-period, cross-over, phase 1 study was conducted in healthy adult subjects. A total of 14 subjects (7 males; 7 females) were randomized 1:1 into two groups, Sequence 1 and Sequence 2. Under fasted conditions in the first treatment period, the Sequence 1 group received a single 2 mg dose of the hard gelatin capsule formulation of Compound 1 (Treatment A), and the Sequence 2 group received a single 2 mg dose of the tablet formulation of Compound 1 (Treatment B). After a 7-day washout, the two groups crossed over in the second treatment period to receive the alternate treatment under fasted conditions. Following another 7-day washout, all subjects received Treatment C (a single 2 mg dose of the tablet formulation of Compound 1 under fed conditions; i.e., FDA-standard high-fat high-calorie meal) in the third treatment period. Blood samples for determination of plasma concentrations of Compound 1 were collected at prespecified time points up to 120 hours post dose. Plasma samples were analyzed for Compound 1 using a validated LC/MS/MS assay. The Compound 1 plasma concentration-time data were analyzed by noncompartmental methods in Phoenix™ WinNonlin® (Version 6.3, Pharsight Corporation) to determine plasma pharmacokinetic parameters including peak concentration ($C_{max}$), time to peak concentration ($T_{max}$), and area under the concentration-time curve from time-zero to the time of the last quantifiable concentration ($AUC_{0-t}$) or to infinity ($AUC_{inf}$). Consistent with the two one-sided test for bioequivalence, analysis of variance (ANOVA) was performed on ln-transformed $AUC_{0-t}$, $AUC_{inf}$ and $C_{max}$ values to determine geometric mean ratios (Test/Reference treatments; see Tables 3 and 4 for treatment designations) and their associated 90% confidence intervals to assess relative bioavailability and food effects. Pharmacokinetic results were also stratified by gender to evaluate any potential differences between males and females. Safety and tolerability were evaluated using physical examination, ophthalmological examination, neurological and progressive multifocal leukoencephalopathy (PML) examination, vital sign measurements (supine blood pressure, heart rate, temperature, and respiratory rate), clinical laboratory evaluations, electrocardiograms (ECGs), telemetry monitoring, tuberculosis (TB) screening, pulmonary function testing (PFT, using spirometry), and reported or observed adverse events (AEs).

No significant differences between Compound 1 mean plasma concentration-time profiles were seen for the tablet and capsule formulations under fasted conditions (FIG. 1). The 90% confidence intervals for the geometric mean ratios of Compound 1 peak ($C_{max}$) and total (AUC) plasma exposure measures, comparing tablet versus capsule formulations, were within the accepted 80% to 125% range for establishing bioequivalence (Table 5).

No significant differences between Compound 1 mean plasma concentration-time profiles were seen for the tablet formulation administered under fed versus fasted conditions (FIG. 1). The 90% confidence intervals for the geometric mean ratios of Compound 1 peak ($C_{max}$) and total (AUC) plasma exposure measures, comparing the tablet under fed versus fasted conditions, were within the accepted 80% to 125% range for establishing no food effect.

Compound 1 mean plasma concentrations and exposure parameters were only moderately higher in females compared to males across treatments.

A total of eight AEs was reported by three subjects over the course of the study and consistent with what was seen previously in healthy volunteer studies. All AEs were considered treatment emergent, with only three AEs considered related to the administration of study medication. There were no serious AEs (SAEs) or AEs that led to subject discontinuation. No clinically significant abnormalities in ECGs or physical exams were observed. There were no AEs related to clinically significant out-of-range vital signs.

Compound 1 capsule and tablet formulations were found to be bioequivalent (interchangeable). No significant differences in Compound 1 exposure for the tablet formulation administered under fasted and fed conditions were demonstrated and thus Compound 1 can be taken without regard to meals. Observed modest gender differences in PK exposure measures were considered not likely clinically meaningful. Overall, the investigational product was well-tolerated in healthy subjects when administered as a 2 mg single dose under both fed and fasted conditions.

TABLE 5

Statistical Analysis Comparing Systemic Exposure of 2 mg Tablet under Fasted Conditions (Treatment B; Test) to 2 mg Capsule under Fasted Conditions (Treatment A; Reference)

| PK Exposure Parameter | Geometric Mean[a] | | GMR (%)[b] | 90% CI[c] | |
|---|---|---|---|---|---|
| | Test | Ref | (Test/Ref) | Lower | Upper |
| $C_{max}$ | 43.49 | 44.26 | 98.25 | 91.42 | 105.59 |
| $AUC_{0-120}$ | 1551.17 | 1565.99 | 99.05 | 94.91 | 103.38 |
| $AUC_{0-t}$ | 1551.2 | 1566.1 | 99.05 | 94.90 | 103.37 |
| $AUC_{inf}$ | 1658.0 | 1703.8 | 97.31 | 92.82 | 102.02 |

[a]Geometric Mean for 2 mg tablet under Fasted Conditions (Test) and 2 mg capsule under fasted conditions (Ref) based on Least Squares Mean of log-transformed parameter values; units are ng/ml and h-ng/ml for $C_{max}$ and AUCs, respectively.
[b]Geometric Mean Ratio (%) = Geometric Mean (Test)/Geometric Mean (Ref)
[c]90% Confidence Interval

TABLE 6

Statistical Analysis Comparing Systemic Exposure of 2 mg Tablet under Fed Conditions (Treatment C; Test) and Fasted Conditions (Treatment B; Reference)

| PK Exposure Parameter | Geometric Mean[a] | | GMR (%)[b] | 90% CI[c] | |
|---|---|---|---|---|---|
| | Test | Ref | (Test/Ref) | Lower | Upper |
| $C_{max}$ | 44.35 | 43.49 | 101.97 | 95.23 | 109.20 |
| $AUC_{0-t}$ | 1691.2 | 1551.2 | 109.03 | 104.35 | 113.91 |
| $AUC_{inf}$ | 1823.6 | 1658.0 | 109.99 | 104.88 | 115.35 |

[a]Geometric Mean for 2 mg tablet under fed conditions (Test) and 2 mg tablet under fasted conditions (Ref) based on Least Squares Mean of log-transformed parameter values; units are ng/ml and hng/mL for $C_{max}$ and AUCs, respectively.
[b]Geometric Mean Ratio (%) = Geometric Mean (Test)/Geometric Mean (Ref)
[c]90% Confidence Interval

Example 6

Compound 1 (1 mg, 2 mg) is evaluated in an open-label, three-treatment, randomized, fixed sequence study to assess plasma pharmacokinetics (PK), pharmacodynamics (PD), safety, and tolerability in the presence and absence of dosing of fluconazole (a moderate inhibitor of CYP2C9), gemfibrozil (a strong inhibitor of CYP2C8), or rifampin (a moderate inducer of both CYP2C8 and CYP2C9) in healthy adult subjects.

Based on results from completed in vitro metabolism studies and a human mass balance clinical study, Compound 1 appears to be extensively metabolized (>25% overall) by oxidative (CYP2C8 and CYP2C9) and conjugation (UGT1A7, minor extent UGT1A1 and UGT1A4) pathways. Compound 1 is eliminated from the systemic circulation mainly due to metabolism and biliary/fecal excretion. Potential changes in Compound 1 pharmacokinetics are evaluated in the presence and absence of co-administered drugs that can impact one or more of these metabolism/elimination pathways-fluconazole or gemfibrozil due to the significant CYP inhibition effects, and rifampin due to the significant CYP induction effects.

The study entails one of three treatments: 1) Compound 1 (1 mg) alone and in the presence of steady state fluconazole (400 mg loading dose followed by daily oral dose 200 mg); 2) Compound 1 (1 mg) alone and in the presence of steady state gemfibrozil (600 mg BID oral dose); and 3) Compound 1 (2 mg) alone and in the presence of steady state rifampin (600 mg daily oral dose).

Each treatment consists of two periods: period 1 (administration of a single oral dose of Compound 1 alone) and period 2 (administration of Compound 1 in the presence of an inhibitor or inducer drug). Each period will be separated by 7-day washout period.

In period 1 on day 1, following an overnight fast, subjects (n=16 per treatment group) will receive a single oral dose of Compound 1 (1 mg for treatments A and B; 2 mg for treatment C) and single dose PK will be assessed over the next 7 days.

In period 2, all 16 subjects from each treatment group will be treated as follows:

Treatment A: On day 8, subjects will be administered a single dose of fluconazole (400 mg) followed by once daily dosing of fluconazole (200 mg) up to day 23. On day 12, following an overnight fast of at least 8 hours, a single dose of Compound 1 (1 mg) will be administered 30 min following daily dose of fluconazole.

Treatment B: On day 8, subjects will be administered twice daily gemfibrozil (600 mg) up to day 23. On day 12, following an overnight fast of at least 8 hours, a single dose of Compound 1 (1 mg) will be administered 30 minutes following daily dose of gemfibrozil.

Treatment C: On day 8, subjects will be administered once daily rifampin (600 mg) up to day 23. On day 15, following an overnight fast of at least 8 hours, a single dose of Compound 1 (2 mg) will be administered 30 min following daily dose of rifampin.

PK and PD profiles of Compound 1 are assessed after dose administration on day 1 (Compound 1 alone) and day 12/15 (in the presence of steady-state CYP2C8/CYP2C9 inhibitor or inducer). Measured PK parameters will include the following assessed using an analysis of covariance model for each comparison (i.e., Compound 1 alone versus the CYP2C8/CYP2C9 inhibitor or inducer):

Cmax: maximum concentration determined directly from the concentration time profile
tmax: time to reach maximum plasma concentration following drug administration determined directly from the concentration-time profile
t1/2: terminal elimination half-life calculated as: $\ln 2/\lambda z$
λz: terminal elimination rate constant determined by selection of at least 3 data points on the terminal phase of the concentration-time curve
AUC0-24: area under the concentration-time curve (AUC) zero to 24 hour calculated using the linear-log trapezoidal rule
Auc0-168: area under the concentration-time curve (AUC) zero to 168 hour calculated using the linear-log trapezoidal rule
AUC0-t
AUClast: AUC from time zero to the time of the last quantifiable concentration (tlast) calculated using the linear-log trapezoidal rule
$AUC_{0-\infty}$: AUC from time zero to the infinity calculated using the linear-log trapezoidal rule CL/F: total body clearance after oral administration Vz/F: apparent volume of distribution after oral administration based on the terminal phase MR: metabolic ratio calculated as AUC0-168(metabolite)/AUC0-168(parent)

Primary analyses evaluate the PK of Compound 1 and potential major metabolites to assess the extent of drug-drug interaction.

Other uses of the disclosed methods will become apparent to those in the art based upon, inter alia, a review of this patent document.

What is claimed is:

1. A method of treating an individual with a sphingosine 1-phosphate subtype 1 (S1P$_1$) receptor-associated disorder comprising:

administering to the individual in need thereof a pharmaceutical dosage form comprising a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, wherein the dosage form is administered under fed conditions, wherein the therapeutically effective amount is equivalent to about 0.5 to about 5.0 mg of Compound 1, wherein the pharmaceutical dosage form has a mean fed/fasted ratio of the area under the plasma concentration versus time curve of from about 0.8 to about 1.25 and a mean fed/fasted ratio of the maximum plasma concentration (Cmax) from about 0.8 to about 1.25.

2. The method of claim 1, wherein the method is non-gender specific.

3. The method of claim 1, further comprising monitoring the individual for an active infection.

4. The method of claim 3, further comprising discontinuing administration if the individual develops an active infection.

5. The method of claim 1, wherein treating comprises inducing and/or maintaining clinical response; improving endoscopic appearance of the mucosa; and/or inducing and/or maintaining clinical remission.

6. The method of claim 1, wherein the Compound 1 is administered without titration.

7. The method of claim 1, wherein said administering results in no serious adverse events.

8. The method of claim 1, wherein the S1P$_1$ receptor-associated disorder is inflammatory bowel disease.

9. The method of claim 8, wherein the inflammatory bowel disease is ulcerative colitis.

10. The method of claim 9, wherein the inflammatory bowel disease is moderately to severely active ulcerative colitis.

11. The method of claim 8, wherein the inflammatory bowel disease is Crohn's disease.

12. The method of claim 8, wherein prior to said administering the individual has a 3-component Mayo Clinic Score of at least 6.

13. The method of claim 8, wherein said administering results in an improvement of the individual's 3-component Mayo Clinic Score.

14. The method of claim 8, wherein said administering results in an improvement of the individual's 2-component Mayo Clinic Score.

15. The method of claim 8, wherein said administering results in an improvement of the individual's Total Mayo Clinic Score.

16. The method of claim 1, wherein the therapeutically effective amount is in an amount equivalent to 1 mg of Compound 1, 2 mg of Compound 1 or 3 mg of Compound 1.

17. The method of claim 1, wherein the Compound 1, or a pharmaceutically acceptable salt, hydrate, or solvate thereof, is an L-arginine salt of Compound 1.

18. The method claim 1, wherein the patient is also being administered a substrate of a membrane transporter selected from P-glycoprotein (Pop), BCRP (breast cancer resistance protein), and OATP1B1, wherein the substrate of OATP1B1 is rifampin and the daily dose of Compound 1 is selected from: 1.0, 1.25, 1.5, and 1.75 mg of Compound 1.

* * * * *